US007413887B2

(12) United States Patent
Dunn-Coleman et al.

(10) Patent No.: US 7,413,887 B2
(45) Date of Patent: Aug. 19, 2008

(54) TRICHODERMA REESEI GLUCOAMYLASE AND HOMOLOGS THEREOF

(75) Inventors: Nigel Dunn-Coleman, Palo Alto, CA (US); Paulien Neefe-Kruithof, Leiden (NL); Craig E. Pilgrim, Beloit, WI (US); Piet Van Solingen, Leiden (NL); Donald E. Ward, Palo Alto, CA (US)

(73) Assignee: Genecor International, Inc., Palo Alto, CA (US)

( * ) Notice: Subject to any disclaimer, the term of this patent is extended or adjusted under 35 U.S.C. 154(b) by 64 days.

(21) Appl. No.: 11/245,628

(22) Filed: Oct. 7, 2005

(65) Prior Publication Data

US 2006/0094080 A1 May 4, 2006

Related U.S. Application Data

(63) Continuation-in-part of application No. 11/136,244, filed on May 24, 2005, now Pat. No. 7,354,752.

(60) Provisional application No. 60/647,925, filed on Jan. 28, 2005, provisional application No. 60/575,175, filed on May 27, 2004, provisional application No. 60/605,437, filed on Aug. 30, 2004.

(51) Int. Cl.
*C12N 9/34* (2006.01)
*C12N 1/00* (2006.01)
*C12N 15/00* (2006.01)
*C12P 21/06* (2006.01)
*C07H 21/02* (2006.01)
*C07H 21/04* (2006.01)

(52) U.S. Cl. .................. 435/205; 435/69.1; 435/254.11; 435/254.6; 435/320.1; 435/484; 435/252.3; 536/23.1; 536/23.2

(58) Field of Classification Search ................ None
See application file for complete search history.

(56) References Cited

U.S. PATENT DOCUMENTS

| 4,247,637 | A | 1/1981 | Tamura et al. |
|---|---|---|---|
| 4,514,496 | A | 4/1985 | Yoshizumi et al. |
| 4,618,579 | A | 10/1986 | Dwiggins et al. |
| 4,794,175 | A | 12/1988 | Nunberg et al. |
| 4,863,864 | A | 9/1989 | Ashikari et al. |
| 5,024,941 | A | 6/1991 | Maine et al. |
| 5,246,853 | A | 9/1993 | Clarkson et al. |
| 5,475,101 | A | 12/1995 | Ward et al. |
| 5,665,585 | A | 9/1997 | Torkkeli et al. |
| 5,847,276 | A | 12/1998 | Mimken et al. |
| 6,022,725 | A | 2/2000 | Fowler et al. |
| 6,254,914 | B1 | 7/2001 | Singh et al. |
| 6,255,084 | B1 | 7/2001 | Nielsen et al. |
| 6,268,328 | B1 | 7/2001 | Mitchinson et al. |
| 6,899,910 | B2 | 5/2005 | Johnston et al. |

FOREIGN PATENT DOCUMENTS

| EP | 0 244 234 | 7/1993 |
|---|---|---|
| EP | 238 023 | 12/1993 |
| EP | 215 594 | 11/1995 |
| WO | WO 88/09795 | 12/1988 |
| WO | WO 92/06209 | 4/1992 |
| WO | WO 96/00787 | 1/1996 |
| WO | WO 02/46429 | 6/2002 |
| WO | WO 03/068976 | 8/2003 |
| WO | WO 2004/080923 | 9/2004 |
| WO | WO 2004/081193 | 9/2004 |
| WO | WO 2005/001036 | 1/2005 |
| WO | WO 2005/052148 | 6/2005 |

OTHER PUBLICATIONS

Guo et al., Protein tolerance to random amino acid change. PNAS., 2004, vol. 101: 9205-9210. Published online Jun. 14, 2004.*

Barnett et al., "Cloning and amplification of the gene encoding and extracellular beta-glucosidase from *Trichoderma reesei*: Evidence for improved rates of saccharification of cellulosic substrates," *Bio/Technology*, V.9 :9, Jun. 1991, pp. 562-567.

Chambergo et al., "Elucidation of the metabolic fate of glucose in the filamentous fungus *Trichoderma reesei* using espressed sequence tag (EST) analysis and cDNA microarrays," *J. of Biological Chemistry*, Apr. 19, 2002, V. 277 :16, pp. 13983-13988.

Database EMBL Nov. 20, 2003, "TrEST-A0518 TrEST-A *Hypocrea jecorina* cDNA clone Tr-A0518 5' similar to glucan 1,4-alpha-glucosidase (EC 3.2.1.3) precuror—*Neurospora crassa*, m RNA sequence." Retrieved from EBI accession No. EM_PRO:CF944444.

Database EMBL Nov. 20, 2003, "TrEST-A0916 TrEST-A *Hypocrea jecorina* c DNA clone Tr-A0916 5' similar to glucan 1,4-alpha-glucosidase (EC 3.2.1.3) precursor—*Neurospora crassa*, mRNA sequence." Retrieved from EBI accession No. EM_PRO:CF943925.

Database EMBL Nov. 20, 2003, "TrEST-A2623 Trest-A *Hypocrea jecorina* CDNA clone Tr-A2623 5' similar to glucan1,4-alpha-glucosidase (EC 3.2.1.3) precuror—*Neurospora crassa*, MRNA sequence." Retrieved from EBI accession No. EM_PRO:CF944284.

Database EMBL Apr. 26, 2003 "tric021xg09 T.reesei mycelial culture, Version Apr. 3 *Hypocrea jecorina* cDNA clone tric021xg09. mRNA sequence."retrived from EBI accession No. EM_PRO:CB900226.

Database EMBL Feb. 6, 2002, "TrEST-A4050 TrEST-A *Hypocrea jecorina* cDNAclone Tr-A4050 5' similar to glucoamylase, mRNA sequence." Retrieved from EBI accession No. EM_PRO:BM076396.

Fagerstrom et al., "Characterization, subsite mapping and partial bamino acid sequence of glucoamylase from the filamentous fungus *Trichoderma reesei*." Biotechnology and Applied Biochemistry Res. Lab., Alko Ltd., V.21 :2, 1995, pp. 223-231.

Fagerstrom et al., "Purification and specificity of recombinant *Hormoconis resinae* glucoamylase P and endogenous glucoamylase from *Trichoderma reesei*," Enzyme and Microbial Technology, V.16 :1, 1994, pp. 36-42.

(Continued)

*Primary Examiner*—Rebecca E. Prouty
*Assistant Examiner*—Ganapathirama Raghu
(74) *Attorney, Agent, or Firm*—Danisco A/S, Genecor Division

(57) ABSTRACT

The present invention is related to glucoamylases having at least 80% sequence identity to a *Trichoderma* glucoamylase having the sequence of SEQ ID NO: 4 and biologically functional fragments thereof. The invention is also related to DNA sequences coding for the glucoamylases, vectors and host cells incorporating the DNA sequences, enzyme compositions and methods of using the glucoamylases in various applications.

21 Claims, 29 Drawing Sheets

OTHER PUBLICATIONS

Stone et al., "Cloning and Sequence Analysis of the Glucoamylase Gene of *Neurospora Crassa*", *Current Genetics*, V.24:3, 1993, pp. 205-211.

Takashima et al., "Molecular cloning and expression of the novel fungal beta-glucosidase from *H.grisea* and *T.reesei*," *J.of Biochemistry, Japanese Biochemical Society*, V.125 :4, Jan. 1999, pp. 728-736.

*Barnett et al., "Cloning and amplification of the gene encoding an extracellular beta-glucosidase from *Trichoderma reesei*: Evidence for improved rates of saccharification of cellulosic substrates," *Bio/Technology*, V.9 :9, Jun. 1991, pp. 562-567.

*Chambergo et al., "Elucidation of the metabolic fate of glucose in the filamentous fungus *Trichoderma reesei* using espressed sequence tag (EST) analysis and cDNA microarrays," *J. of Biological Chemistry*, Apr. 19, 2002, V. 277 :16, pp. 13983-13988.

*Database EMBL Nov. 20, 2003, "TrEST-A0518 TrEST-A *Hypocrea jecorina* cDNA clone Tr-A0518 5' similar to glucan 1,4-alpha-glucosidase (EC 3.2.1.3) precuror—*Neurospora crassa*, m RNA sequence." Retrieved from EBI accession No. EM_PRO:CF944444.

*Database EMBL Nov. 20, 2003, "TrEST-A0916 TrEST-A *Hypocrea jecorina* cDNA clone Tr-A0916 5' similar to glucan 1,4-alpha-glucosidase (EC 3.2.1.3) precursor—*Neurospora crassa*, mRNA sequence." Retrieved from EBI accession No. EM_PRO:CF943925.

*Database EMBL Nov. 20, 2003, "TrEST-A2623 Trest-A *Hypocrea jecorina* CDNA clone Tr-A2623 5' similar to glucan1,4-alpha-glucosidase (EC 3.2.1.3) precuror—*Neurospora crassa*, MRNA sequence." Retrieved from EBI accession No. EM_PRO:CF944284.

*Database EMBL Apr. 26, 2003 "tric021xg09 *T.reesei* mycelial culture, Version Apr. 3 *Hypocrea jecorina* cDNA clone tric021xg09, mRNA sequence."retrived from EBI accession No. EM_PRO:CB900226.

*Database EMBL Feb. 6, 2002, "TrEST-A4050 TrEST-A *Hypocrea jecorina* cDNAclone Tr-A4050 5' similar to glucoamylase, mRNA sequence." Retrieved from EBI accession No. EM_PRO:BM076396.

*Fagerstrom et al., "Characterization, subsite mapping and partial bamino acid sequence of glucoamylase from the filamentous fungus *Trichoderma reesei*." *Biotechnology and Applied Biochemistry Res. Lab., Alko Ltd.*, V.21 :2, 1995, pp. 223-231.

*Fagerstrom et al., "Purification and specificity of recombinant *Hormoconis resinae* glucoamylase P and endogenous glucoamylase from *Trichoderma reesei*," *Enzyme and Microbial Technology*, V.16 :1, 1994, pp. 36-42.

*Stone et al., "Cloning and Sequence Analysis of the Glucoamylase Gene of *Neurospora crassa*", *Current Genetics*, V.24:3, 1993, pp. 205-211.

*Takashima et al., "Molecular cloning and expression of the novel fungal beta-glucosidase from *H.grisea* and *T.reesei*," *J.of Biochemistry, Japanese Biochemical Society*, V.125 :4, Jan. 1999, pp. 728-736.

Altschul, Stephen F. et al., "Basic Local Alignment Search Tool," *J. Mol. Biol.*, 215:403-410 (1990).

Ashikari, Toshihiko et al., "*Rhizopus* Raw-Starch-Degrading Glucoamylase : Its Cloning and Expression in Yeast," *Agric. Biol. Chem.*, vol. 50, No. 4, pp. 957-964, 1986.

Ashikari et al., "Direct fermentation of raw corn to ethanol by yest transformants containing a modified Rhizopus glucoamylase gene," *Appl. Microbiol Biotechnol*, (1989) v.32, pp. 129-133.

Bennett, J. W. et al., ed., *More Gene Manipulations in Fungi*, Academic Press, San Diego, pp. 70-76, 1991.

Bennett See Cees, Am. M. et al., "Heterologous Gene Expression in Filamentous Fungi," More Gene Manipulations in Fungi, Bennett and Lasure, ed., pp. 396-428, 1991.

Boel, E. et al., "Glucoamylases G1 and G2 from *Aspergillus niger* are synthesized from two different but closely related mRNAs, " *The EMBO Journal*, vol. 3, No. 5, pp. 1097-1102, 1984.

Boel, E. et al., "Two different types of intervening sequences in the glucoamylase gene from *Aspergillus niger*," *The EMBO Journal*, vol. 3, No. 7, pp. 1581-1585, 1984.

Brosius, "Laboratory Methods Superpolylinkers in Cloning and Expression Vectors," *DNA*, V. 8, N 10. pp. 759-777, 1989.

Campbell, Edward I. et al., << Improved transformation efficiency of *Aspergillus niger*, Current Genetics, vol. 16, pp. 53-56, 1989.

Cao, Qing-Na et al., "Penicillopepsin-JT2, a recombinant enzyme from *Penicillium janthinellum* and the contribution of a hydrogen bond in subsite $S_3$ to $k_{cat}$," *Protein Science*, vol. 9, pp. 991-1001, 2000.

Cees et al., "Heterologous Gene Expression in Filamentous Fungi," *More Gene Munipulations in Fungi*, ed. by Bennett and Lasure, Chapter 18, pp. 396-428.

Dayhoff, M. O. et al., "A Model of Evolutionary Change in Proteins," *Atlas of Protein Sequence and Structure*, vol. 5, suppl. 3, Dayhoff, M. O. ed., *Natl. Biomed. Res. Foundation, Washington, D.C.*, vol. 5, suppl. 3, pp. 345-352.

De Groot, Marcel et al., "Agrobacterium tumefaciens-mediated transformation of filamentous fungi," *Nature Biotechnology*, vol. 16, pp. 839-842, 1998.

Edman, "On the Mechanism of the Phenyl Isothiocyanate Degradation of Peptides," *Acta Chemica Scandiavica*, 10 (1956) 761-768.

Elder et al., "Glucoamylase Activity in Industrial Enzyme Preparations Using Colorimetric Enzymatic Method," Collaborative Study, *J. of AOAC Intl.*, V. 78 N. 2 (1995).

Finkelstein, David B. et al., "Biotechnology of Filamentous Fungi," Technology and Products, Butterworth-Heinemann, David Finkelstein, ed., pp. 113-156, 1992.

Goto, Masatoshi et al., "The Mechanism of Binding of Glucoamylase I from *Aspergillus awamori* var. *kawachi* to Cyclodextrins and Raw Starch," Biosci. Biotech. Biochem., vol. 58, No. 1, pp. 49-54, 1994.

Harkki, A. et al., "A Novel Fungal Expression System : Secretion of Active Calf Chymosin from the Filamentous Fungus *Trichoderma reesei*," Bio/Technology, vol. 7, pp. 596-603, Jun. 1989.

Harkki, Anu et al., "Genetic engineering of *Trichoderma* to produce strains with novel cellulase profiles," *Enzyme Microb. Technol.*, vol. 13, pp. 227-233, Mar. 1991.

Hayashida, Shinsaku et al., "Molecular Cloning of the Glucoamylase I Gene of *Aspergillus awamori* var. *kawachi* for Localization on the Raw-starch-affinity Site," *Agric. Biol. Chem.*, vol. 53, No. 4. pp. 923-929, 1989.

Houghton-Larsen et al., "Cloning and characterisation of a glucoamylase gene (GlaM) from the dimorphic zygomycete Mucor circinelloides," *Appl. Microbiol. Biotechnol.*, 2003, V. 62, pp. 210-217.

Ilmen, Marja et al., "Regulation of Cellulase Gene Expression in the Filamentous Fungus *Trichoderma reesei*," *Applied and Environmental Microbiology*, vol. 63, No. 4, pp. 1298-1306, Apr. 1997.

Innis, M. A. et al., "Expression, Glycosylation, and Secretion of an *Aspergillus* Glucoamylase by *Saccharomyces cerevisiae*," *Science*, vol. 228, pp. 21-26, 1985.

Kelly, Joan M. et al., "Transformation of *Aspergillus niger by* the *amdS* gene of *Aspergillus nidulans*," *The EMBO Journal*, vol. 4, No. 2, pp. 475-479, 1985.

Miller, Gail L., "Use of Dinitrosalicyclic Acid Reagent for Determination of Reducing Sugar," *Analytical Chemistry*, vol. 31, pp. 426-428. 1959.

Needleman, S. B. et al., "A General Method Applicable to the Search for Similarities in the Amino Acid Sequence of Two Proteins," *J. Mol. Biol*, vol. 48, pp. 443-453, 1970.

Nevalainen, K. M. Helena et al., "The Moleclar Biology of *Trichoderma* and Its Application to the Expression of Both Homologous and Heterologous Genes," *Melecular Industrial Mycology*, Leong and Berka, ed., Marcel Dekker, Inc., NY, pp. 129-148, 1992.

Nunberg, Jack H. et al., "Molecular Cloning and Characterization of the Glucoamylase Gene of *Aspergillus awamori*," *Molecular and Cellular Biology*, pp. 2306-2315, Nov. 1984.

Pearson and Lipman, "Improved tools for biological sequence comparison," *PNAS USA*, (1988), 85:2444-2448.

Penttila, Merja et al., "A versatile transformation system for the cellulolytic filamentous fungus *Trichoderma reesei*," Gene, vol. 61, pp. 155-164, 1987.

Pourquie, J. et al., "Scale Up of Cellulase Production and Utilization," *Biochemistry and Genetics of Cellulose Degradation*, Aubert, J. P. et al., ed., Academic Press, pp. 71-86, 1988.

Punt et al., "Transormation of Aspergillus based on the hygromycin B resistance marker from Escherichia coli," *Gene*, 56 (1987 pp. 117-124.

Smith et al., "Comparison of Biosequences," *Advances in Applied Mathematics*, V. 2, pp. 482-489 (1981).

Smith should be "Shpaer", "GeneAssist—Smith Waterman and Other Database Similarity Searches and Identification of Motifs," *Methods in Molecular Biology, Sequence Data Anaylsis Guidebook*, Humana Press, Inc. 70:173-187.

Thompson, The Clustal$_X$ windows interface : flexible strategies for multiple sequence alignment aided by quality analysis tools, *Nucleic Acids Research*, V. 25, N. 24, pp. 4876-4881, (1997).

Van den Hondel Should be Cees, et al., "Heterologous Gene Expression in Filamentous Fungi," *More Gene Manipulations in Fungi*, Chapter 18, pp. 396-428, 1991, Academic Press, Inc.

* cited by examiner gDNA Sequence from *Trichoderma reesei* (SEQ ID NO: 1)

```
ATGCACGTCC TGTCGACTGC GGTGCTGCTC GGCTCCGTTG CCGTTCAAAA GGTCCTGGGA
AGACCAGGAT CAAGCGGTCT GTCGACGTCA CCAAGAGGTC TGTTGACGAC TTCATCAGCA
CCGAGACGCC TATTGCACTG AACAATCTTC TTTGCAATGT TGGTCCTGAT GGATGCCGTG
CATTCGGCAC ATCAGCTGGT GCGGTGATTG CATCTCCCAG CACAATTGAC CCGGACTGTA
AGTTGGCCTT GATGAACCAT ATCATATATC GCCGAGAAGT GGACCGCGTG CTGAGACTGA
GACAGACTAT TACATGTGGA CGCGAGATAG CGCTCTTGTC TTCAAGAACC TCATCGACCG
CTTCACCGAA ACGTACGATG CGGGCCTGCA GCGCCGCATC GAGCAGTACA TTACTGCCCA
GGTCACTCTC CAGGGCCTCT CTAACCCCTC GGGCTCCCTC GCGGACGGCT CTGGTCTCGG
CGAGCCCAAG TTTGAGTTGA CCCTGAAGCC TTTCACCGGC AACTGGGGTC GACCGCAGCG
GGATGGCCCA GCTCTGCGAG CCATTGCCTT GATTGGATAC TCAAAGTGGC TCATCAACAA
CAACTATCAG TCGACTGTGT CCAACGTCAT CTGGCCTATT GTGCGCAACG ACCTCAACTA
TGTTGCCCAG TACTGGTCAG TGCTTGCTTG CTCTTGAATT ACGTCTTTGC TTGTGTGTCT
AATGCCTCCA CCACAGGAAC CAAACCGGCT TTGACCTCTG GAAGAAGTC AATGGGAGCT
CATTCTTTAC TGTTGCCAAC CAGCACCGAG GTATGAAGCA AATCCTCGAC ATTCGCTGCT
ACTGCACATG AGCATTGTTA CTGACCAGCT CTACAGCACT TGTCGAGGGC GCCACTCTTG
CTGCCACTCT TGGCCAGTCG GGAAGCGCTT ATTCATCTGT TGCTCCCCAG GTTTTGTGCT
TTCTCCAACG ATTCTGGGTG TCGTCTGGTG GATACGTCGA CTCCAACAGT ATGTCTTTTC
ACTGTTTATA TGAGATTGGC CAATACTGAT AGCTCGCCTC TAGTCAACAC AACGAGGGC
AGGACTGGCA AGGATGTCAA CTCCGTCCTG ACTTCCATCC ACACCTTCGA TCCCAACCTT
GGCTGTGACG CAGGCACCTT CCAGCCATGC AGTGACAAAG CGCTCTCCAA CCTCAAGGTT
GTTGTCGACT CCTTCCGCTC CATCTACGGC GTGAACAAGG GCATTCCTGC CGGTGCTGCC
GTCGCCATTG CCGGTATGC AGAGGATGTG TACTACAACG GCAACCCTTG GTATCTTGCT
ACATTTGCTG CTGCCGAGCA GCTGTACGAT GCCATCTACG TCTGGAAGAA GACGGGCTCC
ATCACGGTGA CCGCCACCTC CCTGGCCTTC TTCCAGGAGC TTGTTCCTGG CGTGACGGCC
GGGACCTACT CCAGCAGCTC TTCGACCTTT ACCAACATCA TCAACGCCGT CTCGACATAC
GCCGATGGCT TCCTCAGCGA GGCTGCCAAG TACGTCCCCG CCGACGGTTC GCTGGCCGAG
CAGTTTGACC GCAACAGCGG CACTCCGCTG TCTGCGCTTC ACCTGACGTG GTCGTACGCC
TCGTTCTTGA CAGCCACGGC CCGTCGGGCT GGCATCGTGC CCCCCTCGTG GCCAACAGC
AGCGCTAGCA CGATCCCCTC GACGTGCTCC GGCGCGTCCG TGGTCGGATC CTACTCGCGT
CCCACCGCCA CGTCATTCCC TCCGTCGCAG ACGCCCAAGC CTGGCGTGCC TTCCGGTACT
CCCTACACGC CCTGCCCTG CGCGACCCCA ACCTCCGTGG CCGTCACCTT CCACGAGCTC
GTGTCGACAC AGTTTGGCCA GACGGTCAAG GTGGCGGGCA ACGCCGCGGC CCTGGGCAAC
TGGAGCACGA GCGCCGCCGT GGCTCTGGAC GCCGTCAACT ATGCCGATAA CCACCCCCTG
TGGATTGGGA CGGTCAACCT CGAGGCTGGA GACGTCGTGG AGTACAAGTA CATCAATGTG
GGCCAAGATG GCTCCGTGAC CTGGGAGAGT GATCCCAACC ACACTTACAC GGTTCCTGCG
GTGGCTTGTG TGACGCAGGT TGTCAAGGAG GAACCTGGCA GTCGTAA
```

FIG. 1 cDNA Sequence from Trichoderma reesei (SEQ ID NO: 2)

```
ATGCACGTCC TGTCGACTGC GGTGCTGCTC GGCTCCGTTG CCGTTCAAAA GGTCCTGGGA
AGACCAGGAT CAAGCGGTCT GTCCGACGTC ACCAAGAGGT CTGTTGACGA CTTCATCAGC
ACCGAGACGC CTATTGCACT GAACAATCTT CTTTGCAATG TTGGTCCTGA TGGATGCCGT
GCATTCGGCA CATCAGCTGG TGCGGTGATT GCATCTCCCA GCACAATTGA CCCGGACTAC
TATTACATGT GGACGCGAGA TAGCGCTCTT GTCTTCAAGA ACCTCATCGA CCGCTTCACC
GAAACGTACG ATGCGGGCCT GCAGCGCCGC ATCGAGCAGT ACATTACTGC CAGGTCACT
CTCCAGGGCC TCTCTAACCC CTCGGGCTCC CTCGCGGACG GCTCTGGTCT CGGCGAGCCC
AAGTTTGAGT TGACCCTGAA GCCTTTCACC GGCAACTGGG GTCGACCGCA GCGGGATGGC
CCAGCTCTGC GAGCCATTGC CTTGATTGGA TACTCAAAGT GGCTCATCAA CAACAACTAT
CAGTCGACTG TGTCCAACGT CATCTGGCCT ATTGTGCGCA ACGACCTCAA CTATGTTGCC
CAGTACTGGA ACCAAACCGG CTTTGACCTC TGGGAAGAAG TCAATGGGAG CTCATTCTTT
ACTGTTGCCA ACCAGCACCG AGCACTTGTC GAGGGCGCCA CTCTTGCTGC CACTCTTGGC
CAGTCGGGAA GCGCTTATTC ATCTGTTGCT CCCCAGGTTT GTGCTTTCT CCAACGATTC
TGGGTGTCGT CTGGTGGATA CGTCGACTCC AACATCAACA CCAACGAGGG CAGGACTGGC
AAGGATGTCA ACTCCGTCCT GACTTCCATC CACACCTTCG ATCCCAACCT TGGCTGTGAC
GCAGGCACCT TCCAGCCATG CAGTGACAAA GCGCTCTCCA ACCTCAAGGT TGTTGTCGAC
TCCTTCCGCT CCATCTACGG CGTGAACAAG GGCATTCCTG CCGGTGCTGC CGTCGCCATT
GGCCGGTATG CAGAGGATGT GTACTACAAC GGCAACCCTT GGTATCTTGC TACATTTGCT
GCTGCCGAGC AGCTGTACGA TGCCATCTAC GTCTGGAAGA AGACGGGCTC CATCACGGTG
ACCGCCACCT CCCTGGCCTT CTTCCAGGAG CTTGTTCCTG GCGTGACGGC CGGGACCTAC
TCCAGCAGCT CTTCGACCTT TACCAACATC ATCAACGCCG TCTCGACATA CGCCGATGGC
TTCCTCAGCG AGGCTGCCAA GTACGTCCCC GCCGACGGTT CGCTGGCCGA GCAGTTTGAC
CGCAACAGCG GCACTCCGCT GTCTGCGCTT CACCTGACGT GGTCGTACGC CTCGTTCTTG
ACAGCCACGG CCCGTCGGGC TGGCATCGTG CCCCCCTCGT GGGCCAACAG CAGCGCTAGC
ACGATCCCCT CGACGTGCTC CGGCGCGTCC GTGGTCGGAT CCTACTCGCG TCCCACCGCC
ACGTCATTCC CTCCGTCGCA GACGCCCAAG CCTGGCGTGC CTTCCGGTAC TCCCTACACG
CCCCTGCCCT GCGCGACCCC AACCTCCGTG GCCGTCACCT TCCACGAGCT CGTGTCGACA
CAGTTTGGCC AGACGGTCAA GGTGGCGGGC AACGCCGCGG CCCTGGGCAA CTGGAGCACG
AGCGCCGCCG TGGCTCTGGA CGCCGTCAAC TATGCCGATA CCACCCCCT GTGGATTGGG
ACGGTCAACC TCGAGGCTGG AGACGTCGTG GAGTACAAGT ACATCAATGT GGGCCAAGAT
GGCTCCGTGA CCTGGGAGAG TGATCCCAAC CACACTTACA CGGTTCCTGC GGTGGCTTGT
GTGACGCAGG TTGTCAAGGA GGACACCTGG CAGTCGTAA
```

*FIG. 2*

Amino Acid Sequence of TrGA (SEQ ID NO: 3)

```
  1 MHVLSTAVLL GSVAVQKVLG RPGSSGLSDV TKRSVDDFIS TETPIALNNL
 51 LCNVGPDGCR AFGTSAGAVI ASPSTIDPDY YYMWTRDSAL VFKNLIDRFT
101 ETYDAGLQRR IEQYITAQVT LQGLSNPSGS LADGSGLGEP KFELTLKPFT
151 GNWGRPQRDG PALRAIALIG YSKWLINNNY QSTVSNVIWP IVRNDLNYVA
201 QYWNQTGFDL WEEVNGSSFF TVANQHRALV EGATLAATLG QSGSAYSSVA
251 PQVLCFLQRF WVSSGGYVDS NINTNEGRTG KDVNSVLTSI HTFDPNLGCD
301 AGTFQPCSDK ALSNLKVVVD SFRSIYGVNK GIPAGAAVAI GRYAEDVYYN
351 GNPWYLATFA AAEQLYDAIY VWKKTGSITV TATSLAFFQE LVPGVTAGTY
401 SSSSSTFTNI INAVSTYADG FLSEAAKYVP ADGSLAEQFD RNSGTPLSAL
451 HLTWSYASFL TATARRAGIV PPSWANSSAS TIPSTCSGAS VVGSYSRPTA
501 TSFPPSQTPK PGVPSGTPYT PLPCATPTSV AVTFHELVST QFGQTVKVAG
551 NAAALGNWST SAAVALDAVN YADNHPLWIG TVNLEAGDVV EYKYINVGQD
601 GSVTWESDPN HTYTVPAVAC VTQVVKEDTW QS
```

FIG. 3A

Mature Protein TrGA (SEQ ID NO: 4)

```
  1 SVDDFISTET PIALNNLLCN VGPDGCRAFG TSAGAVIASP STIDPDYYYM
 51 WTRDSALVFK NLIDRFTETY DAGLQRRIEQ YITAQVTLQG LSNPSGSLAD
101 GSGLGEPKFE LTLKPFTGNW GRPQRDGPAL RAIALIGYSK WLINNNYQST
151 VSNVIWPIVR NDLNYVAQYW NQTGFDLWEE VNGSSFFTVA NQHRALVEGA
201 TLAATLGQSG SAYSSVAPQV LCFLQRFWVS SGGYVDSNIN TNEGRTGKDV
251 NSVLTSIHTF DPNLGCDAGT FQPCSDKALS NLKVVVDSFR SIYGVNKGIP
301 AGAAVAIGRY AEDVYYNGNP WYLATFAAAE QLYDAIYVWK KTGSITVTAT
351 SLAFFQELVP GVTAGTYSSS SSTFTNIINA VSTYADGFLS EAAKYVPADG
401 SLAEQFDRNS GTPLSALHLT WSYASFLTAT ARRAGIVPPS WANSSASTIP
451 STCSGASVVG SYSRPTATSF PPSQTPKPGV PSGTPYTPLP CATPTSVAVT
501 FHELVSTQFG QTVKVAGNAA ALGNWSTSAA VALDAVNYAD NHPLWIGTVN
551 LEAGDVVEYK YINVGQDGSV TWESDPNHTY TVPAVACVTQ VVKEDTWQS
```

FIG. 3B gDNA Sequence from Hypocrea citrina var. americana,
(GA102) - 2154 bp (SEQ ID NO: 5)

```
ATGCACGTCC TGTCGACGGC TGTGTTGCTC GGCTTGGTGG CCGTTCAAAA GGTTCTGGGA
AGGCCAGGGC TGAATGGCGT ACCCGACGTC ACAAAACGGT CCGTTGACGA CTTCATCAGC
AATGAGTCTC CTATTGCACT GAACAACCTC CTGTGCAATG TCGGCCCTGA TGGATGCCGC
GCCTTTGGCG CATCGGCAGG CACTGTCGCT GCCTCGCCCA GCACAACCGA CCCAGACTGT
AAGTGTATAC GAGACAATCC ATGAGATGAG GCCCTCTACG TGTATTGCAC ACTAACACAG
ATATTGACGC GGATTACTAC ATGTGGACGC GAGACAGTGC TCTCATCTTC AAGACCGTTG
TCGACAGGTT CACCCAGAAC TACGATGCTA GCCTGCAGAA GCGCATTGAG CAGTACATTG
CTGCTCAGGC CACGCTTCAG GGGATTTCCA ACCCATCGGG CTCTCTAGCA GATGGGTCCG
GTCTCGGCGA GCCCAAGTTC GAGCTGACCC TGAATCAGTT CACCGGCCAC TGGGGCCGAC
CACAGCGGGA CGGTCCAGCT CTGCAGCCA TTGCCTTGAT CGGCTATTCG AAGTGGCTCA
TCGACAACAA CTACCAGTCG ACTGTGTCCG ACATCATCTG GCCCATTCTG CGGAATGATC
TCAACTACGT AGCGCAGTAC TGGTATGTGT TGCTTACTGT TTTGCTCCGT TGAGAATGGT
CCGTTTCTAA CCTTTAAACT GTAGGAACCA AACCGGTTTT GACTTGTGGG AGGAAGTTGA
AGGAAGCTCA TTCTTTACCG TTGCTAACCA GCACCGAGGT ACGGAACACG ACTCAGGTCA
ACTGACGAGA GGCGCTGCTA ACACGCTTCA CAGCCCTTGT CGAGGGCGCT ACGCTTGCTG
CTATCCTTGG CCAGTCGGGA AGCAGCTATT CTGCTGTTGC TCCCCAGATT CTGTGCTTCC
TCCAAAAATT TTGGGTGTCT TCCGGCGGAT ACGTGAACTC CAACAGTGCG TCTATGTGTG
CGCTCTGTGA GCTCTGATGA AGCGGATGCT AACAGTTTAT CTGTAATAGT CAACAGTGAT
ATCAACAGAA CCGGAAAGGA TGCCAACTCT CTTCTCGCCT CTATCCACAC ATTCGATCCT
AGCATTGGCT GTGACCCCGC TACCTTCCAG CCCTGCAGTG ATAAGGCCCT TTCCAACCTC
AAGTCCGTCG TCGATTCATT CCGCTCCATC TACGGCGTCA ACCAGGGCAT CTCTGCTGGC
TCTGCCGTGG CCATCGGCCG ATACTCCGAG GACGTCTACT TCAACGGAAA CCCCTGGTAC
CTGGCCACAT TGCCGCCGC CGAGCAGCTG TACGACTCCC TGTACGTGTG GAAGCAGACG
GGCTCGATCA CGGTGACGGC CATCCCTCTG GCCTTCTTCC AGGAGCTCGT GCCCGGCGTG
GCCGCCGGCA CGTACCTCAG CAGCCAGTCT ACGTTCACCA GCATCGTCAA CGCCGTCTCA
GCCTACGCGG ACGGCTTCCT AAACGAGGCG GCCAAGTACG TCCCCTCCGA TGGCTCGCTC
GCCGAGCAGT TTGACAAGAA CAACGGCACG CCTCTGTCGG CCGTGCACCT GACCTGGTCG
TATGCCTCCT TTTTGACGGC GACCGCGCGT CGAGCTGGTT CTGTGCCTCC GTCGTGGGCC
AATAGCAACG CAACCTCGAT TCCGACGGCC TGCTCTGGAA CGTCGGTGGT TGGATCATAC
TCGAGTCCCA CAGCCACGTC ATTCCCTCCC TCCCAGACGC CCAAAGTTGG CAAGCCAACG
GGCACGCCCT TCACGCCCAT TCCTGCGCC ACGCCAACCT CCGTGGCCGT CACCTTCCAC
GAGCTCCCAA CGACGCAGTT TGGCCAGACC ATCAAATTGG CTGGCAGCGC TGAGGCCCTG
GGCAACTGGA GCACCGGTGC CGCCGTGGGC CTCGACGCCG CCAACTATGC GTCCAACCAC
CCGTTGTGGT TTGGCACGCT CAACCTCCAG GCCGGCGATG TCATCGAGTA CAAGTACATC
AACGTGGGCA AGGACGGCTC CGTGACGTGG GAGAGCGACC CCAACCACAC GTACACCGTT
CCTGCGGTGG CGTGTGTCAC CGAGGTGGTC AAGGAGGACA CCTGGCAGTC GTAA
```

*FIG. 4* gDNA Sequence from Hypocrea vinosa, (GA104) - 2152 bp (SEQ ID NO: 7)

```
ATGCACGTGC TGTCGACTGC TGTGCTACTT GGCTCAGTTG CCGTCCAAAA GGTTCTGGGA
AGACCAGGAT CAAACGGTCT ATCCGGCGTC ACAAAACGAT CTGTGGATGA CTTTATCAAC
ACACAGACTC CCATTGCACT AAACAACCTT CTTTGCAATG TTGGCCCTGA TGGATGCCGT
GCCTTTGGTA CATCGGCCGG TGCCGTGATT GCATCTCCGA GCACAACTGA CCCAGACTGT
AAGTTTGACT TATACGGGCT TATCTCCTGA TATGTCAAGT TTCATATGCT AACACGAGGG
TAATTAATCA GACTACTACA TGTGGACGCG AGATAGTGCT CTTGTCTTCA AGAACATTGT
AGACCGCTTC ACTCAGCAGT ATGATGCCGG CCTGCAGCGC CGCATCGAGC AGTACATTTC
TGCCCAGGTC ACTCTTCAGG GCATCTCAAA CCCCTCTGGC TCTCTCTCGG ACGGGTCCGG
TCTTGGTGAA CCCAAGTTTG AGTTGACCTT GAGCCAGTTC ACTGGCAACT GGGGTCGCCC
GCAGCGCGAC GGCCCAGCTC TCCGAGCCAT TGCCTTGATT GGTTATTCGA AGTGGCTCAT
CAACAACAAC TACCAGTCAA CGGTGTCAAA TATCATCTGG CCCATCGTAC GGAATGACCT
CAACTATGTT GCCCAATACT GGTAAGTACA AGCTCGCCGT CTTTTCGTCT TGTTATGACT
AATTCCAACA CCTTCACTTT AGGAACCAAA CCGGTTTCGA CCTGTGGGAG GAAGTCAATG
GTAGCTCGTT CTTTACCGTT GCCAACCAGC ACCGAGGTAT GTATCAACAT CTCATGTGCA
ATTTTTAGTT GGAAATAAAC AATGCTGACG AGTTCTCCAG CTCTTGTTGA GGGCGCCACA
CTTGCTGCTA CCCTCGGCCA GTCGGGAAGC ACCTATTCCT CAGTTGCGCC TCAGATCCTG
TGCTTCCTCC AAAGATTCTG GGTGTCGGGT GGATATATTG ACTCTAATAG TAAGTCTACT
AGTACCATAT GCTTTGATGA AGGGCGATAC TAAACAGCTT GCCATAGTCA ATACCAACGA
AGGCAGGACT GGAAAAGATG CCAACTCTCT TCTCGCATCT ATCCACACGT TCGATCCTAG
CCTCGGCTGT GACGCCTCTA CCTTCCAGCC TTGCAGTGAC AAAGCTCTCT CCAACCTCAA
GGTTGTTGTA GACTCCTTCC GCTCCATCTA CGGTGTCAAC AAGGGCATTC CTGCTGGCTC
TGCTGTCGCC ATCGGCAGAT ACCCCGAAGA TGTGTACTTT AACGGAAACC CTTGGTACCT
CGCCACGTTC GCTGCTGCCG AGCAACTTTA CGACTCCGTC TATGTCTGGA AGAAGACAGG
CTCCATCACA GTGACTTCCA CTTCTTCGGC CTTCTTCCAG GAGCTCGTTC CCGGCGTCGC
AGCTGGGACT TACTCCAGCA GCCAGTCTAC CTTCACAAGC ATCATCAACG CCATCTCGAC
ATATGCTGAT GGATTCCTCA GCGAGGCTGC CAAGTACGTC CCCGCTGATG GTTCGCTCGC
CGAGCAGTTT GATCGCAACA CCGGCACACC TCTGTCAGCC GTTCACCTGA CCTGGTCTTA
CGCCTCGTTT CTCACCGCCG CGGCCCGTCG GGCTGGCGTT GTCCCCCCCT CGTGGGCCAG
CAGCGGCGCT AATACAGTTC CTTCAAGCTG CTCGGGAGCT TCTGTGGTTG GATCCTACTC
GCGTCCTACA GCCACGTCAT TCCCACCATC GCAGACCCCC AAGCCTGGCG TTCCTTCTGG
TACTCCCTTC ACTCCCATTC CCTGTGCTAC CCCGACTTCC GTTGCCGTCA CTTTCCACGA
GCTTGCCACA ACCCAGTTTG GTCAGACTAT CAAGGTCGCT GGTAGCGCTC CCGAGCTGGG
CAACTGGAGC ACGAGCGCGG CCATTGCTCT GGATGCCGTC AACTATGCCA CTAACCACCC
CTTGTGGATT GGATCGGTCA ATCTGGAAGC CGGAGATGTT ATCGAGTACA AGTACATTAA
CGTGGGCCAG GATGGTTCCG TCACCTGGGA GAGCGATCCT AACCACACCT ACACTGTTCC
TGCGGTGGCA TGTGTTACCG AGGTGGTTAA GGAGGACACC TGGCAGTCGT AA
```

FIG. 5 gDNA Sequence from Trichoderma sp., (GA105) - 2158 bp  (SEQ ID NO: 9)

```
ATGCACGTCC TGTCGACTGC GGTGCTGCTT GGCTCCGTTG CCGTTCAAAA GGTCCTGGGA
AGACCAGGAT CAAGCGGGCT ATATGACGTC ACCAAGAGAT CCGTCGACGA CTTCATCAGC
ACCGAAACTC CTATTGCACT GAACAACCTT CTCTGCAATG TTGGTCCTGA TGGATGTCGT
GCATTTGGCA CGTCAGCTGG TGCGGTGATT GCATCTCCCA GCACGACCGA CCCAGACTGT
AAGTTGAAAT TCCAGCGCTA CATCTCACAT ATCGCCGAGC AGTCGACAGC GTGCTAATAT
CGAGACAGAC TATTACATGT GGACGCGGGA TAGTGCTCTT GTCTTCAAAA ACCTTGTCGA
CCGCTTCACC GAAGAGTACG ATGCTGGCCT GCAGCGCCGC ATTGAGCAGT ACATCACTGC
CCAGGTCACT CTCCAGGGCC TCACCAACCC ATCGGGTTCC CTCTCGGACG GGTCTGGTCT
GGGCGAGCCC AAGTTTGAGT TGACCCTGCA GCCATTCACT GGCAACTGGG GTCGGCCGCA
GCGGGATGGC CCAGCTCTGC GAGCCATTGC CTTGATTGGC TATGCGAAGT GGCTTATCAA
CAACAACTAT CAGTCCACTG TGTCCAGCGT CATCTGGCCC ATTGTGCGCA ACGACCTCAA
CTACGTTGCT CAATACTGGT TAGTGACGGC TTGCCCTCGA ATCACATCTT TGCTTGTGTG
TCTAACGTCT TCACTTCAGG AACCAAACCG GCTTTGACCT CTGGGAGGAA GTCGATGGAA
GCTCATTCTT CACTGTTGCC AACCAGCACC GAGGTATGAA GCAAACCGTC CACACTCGCT
GTTACTGTAT GTGACCATTG TTACTGACCA GCTCTCCAGC ACTTGTTGAG GGTGCCACGC
TTGTTGCCAC GCTTGGCCAG TCGGGAGACA CATATTCATC CGTTGCTCCC CAAGTCTTGT
GCTTCCTTCA GCGATTCTGG GTGTCGTCCG GTGGATACAT CGACTCCAAC AGTATGTTTT
GCACTGGTCA TGAATGTTGA TAACGACAAT GGCTAATCGC TCTCCTTTAG TCAACACCAA
CGAGGGCAGG ACTGGAAAGG ATGCCAACTC GATTCTCACT TCCATCCACA CCTTTGACCC
CAATCTTGGC TGCGATGCAG GCACCTTCCA GCCATGCAGT GACAAAGCGC TCTCCAACCT
CAAGGTCGTT GTCGACTCCT TCCGCTCCAT CTACAGCTTG AACAAGGGCA TTCCCGCTGG
TGCTGCCGTC GCCATTGGCA GATATCCAGA GGATGTGTAC TTCAACGGAA ACCCTTGGTA
CCTTGCCACG TTTGCTGCTG CTGAGCAGCT GTACGATGCC GTCTACGTCT GGAAGGAGAC
GGGCTCCATC ACGGTGACCG CCACCTCCCT GGCCTTCTTC CAGGAGCTTG TTCCCGGCGT
GACAGCTGGG ACCTACTCCA GCAGCTCGTC GTCGACCTTT ACCACCATCA TCAACGCCGT
CTCGACGTAC GCCGATGGCT TCCTCAGCGA GGCTGCCAAG TACGTCCCCG CCGACGGTTC
GCTGGCAGAG CAGTTCGACC GCAACAACGG CACTGCGCTG TCCGCCCGTC ACCTGACGTG
GTCGTACGCC TCCTTCTTGA CAGCCACGGC CCGTCGTGCT GGCGTCGTGC CCCCTTCGTG
GGCAAACAGC AGCGCCAGCA CGATTCCCTC GACGTGCTCC GGCGCGTCCG TGGTCGGCTC
CTACTCGCGT CCCACAGCCA CGTCATTCCC TCCGTCGCAG ACGCCCAAGC TGGCGTTCC
GTCCGGCACT CCCTACACGC CCTGCCCTG CGCTACCCCA ACGTCCGTGG CCGTCACCTT
CCACGAGCTC GTGTCGACAC AGTTTGGCCA GACGGTCAAG GTCGCGGGCA GCGCTCAGGC
CCTGGGCAAC TGGAGCACGA GCGCCGCTGT GGCTCTGGAT GCCGTCAACT ACGCCGATAA
CCATCCCCTG TGGATCGGAA CGGTTAACCT CGAGGCCGGA GACGTTGTGG AGTACAAGTA
CATCAATGTC GGTCAGGATG GCTCCGTGAC CTGGGAGAGT GACCCCAACC ACACTTACAC
GGTTCCTGCG GTGGCTTGTG TGACGCAGGT TGTCAAGGAG GACACCTGGC AGTCGTAA
```

FIG. 6 gDNA Sequence from *Hypocrea gelatinosa*, (GA107) - 2144 bp  (SEQ ID NO: 11)

```
ATGCACGTGC TGTCGACTGC TGTGCTACTC GGCTCAGTTG CCGTCCAGAA GGTCCTGGGA
AGACCAGGAT CAAACGGCCT TTCCGGCGTC ACAAAACGAT CTGTGGATGA CTTCATCAAC
ACACAGACTC CCATTGCGCT AAACAACCTC CTTTGCAATG TTGGCCCTGA TGGATGCCGT
GCCTTTGGCA CATCGGCCGG TGCTGTGATT GCATCTCCGA GCACAACTGA CCCAGATTGT
AAGTTTGACT TATACCGGCA TATTCTTGAG ATGTCAAGTT TCACATACTA ACACGGGGGT
AATTGATCAG ACTACTACAT GTGGACGCGA GACAGTGCTC TTGTCTTCAA GAACATTGTC
GACCGTTTCA CTCAACAGTA CGATGCCGGC CTGCAGCGCC GCATCGAGCA GTACATTTCT
GCCCAGGTCA CTCTCCAGGG GCCCTCAAAC CCCTCTGGCT CTCTCTCGGA CGGGTCCGGT
CTTGGTGAAC CAAGTTTGA GCTGACTTTG AGTCAGTTCA CTGGAAACTG GGTCGTCCG
CAGCGCGATG GCCCAGCTCT TCGAGCTATT GCCTTAATAG CTATTCGAA GTGGCTCATC
AACAACAACT ACCAGTCAAC TGTATCAAGT ATCATCTGGC CCATTGTACG AAATGATCTC
AACTATGTTG CCCAGTACTG GTTAGTACCA ACTCGCTGTC TCTTCGTCTT GTTAAGACT
ATCTCTAATA CATTCACTTC AGGAACCAAA CTGGTTTCGA CCTGTGGGAG GAAGTCAATG
GTAGCTCGTT CTTTACTGTT GCCAACCAGC ATCGAGGTAT GTATCAACAA CTCATACATT
AATTGGAAAT AAAAAATGCT GACAAGTTCC TTAGCTCTTG TTGAGGGTGC CACACTTGCC
GCTACCCTCG GCCAGTCAGG AAGCACCTAT TCCTCTGTTG CTCCTCAAAT CCTGTGCTTC
CTCCAGAGAT TTTGGGTGTC GGGAGGATAC ATTGACTCCA ACAGTAAGTC TATCAGCACT
ATGCCTGGAT GAAGACCAAT ACTAAACAGC TCGTTATAGT CAACAGCAAC GATGGCAGGA
CTGGCAAAGA TGCCAACTCT CTTCTCGCAT CTATCCACAC CTTCGATCCT AGCCTGGGCT
GCGACGCCTC CACCTTCCAG CCTTGCAGTG ACAAAGCTCT CTCCAATCTC AAGGTTGTTG
TAGACTCCTT CCGCTCCATC TACGGCGTCA ACAAAGGTAT TTCTGCTGGC TCTGCTGTTG
CCATCGGCAG ATACCCCGAA GATGTGTACT TTAACGGAAA CCCCTGGTAT CTTGCCACGT
TCGCTGCTGC TGAGCAACTT TACGACTCCG TCTATGTCTG GAAGAAGACA GGCTCCATCA
CGGTGACTTC CACCTCTTTG GCCTTCTTCC AGGAGCTTGT CCCCGGTGTC GCGGCTGGAA
CTTACTCCAG CAGCCAGTCT ACCTTCACGA GCATCGTCAA CGCCGTCTCG ACATATGCTG
ATGGATTCCT CAGCGAGGCT GCCAAGTACG TCCCTGCTGA TGGTTCGCTC GCCGAGCAGT
TCGATCGAAA CACCGGAACG CCTCTGTCAG CCGTTCACCT GACCTGGTCA TACGCCTCGT
TTTTCACCGC TGCGGCCCGT CGGTCTGGCG TTGTCCCCCC ATCGTGGGCC AGCAGCGGCG
CTAACTCAAT CCCTGCAACC TGCTCCGGAG CGTCTGTGGT TGGATCCTAC TCGAGTCCTA
CAGCCACGTC ATTCCCACCA TCGCAGACCC CAAGCCTGG CGTTCCTTCT GGTACTCCCT
TCACTCCCCT TCCCTGCGCT ACCCCGACTT CCGTTGCCGT CACTTTCCAT GAGCTTGCCA
CAACCCAGTT TGGCCAGAAT ATCAAGGTCG CCGGCAGCGC TCCCGAGCTG GGCAACTGGA
GCACGAGCGC GGCCATTGCT CTGGATGCCG TCAACTATGC CACTAACCAT CCCCTGTGGA
TTGGATCGGT CAATCTGGAA GCCGGAGACG TCATTGAGTA CAAGTACATC AACGTGGGTC
AGGATGGTTC CGTCACCTGG GAGAGCGACC CCAACCACAC CTACACTGTT CCAGCGGTTG
CCTGTGTCAC TGAGGTGGTT AAGGAGGACA CCTGGCAGTC GTAA
```

FIG. 7 gDNA Sequence from *Hypocrea orientalis*, (GA108) - 2127 bp (SEQ ID NO: 13)

```
ATGCACGTCC TGTCGACTGC GGTGCTGCTC GGCTCCGTTG CCGTTCAGAA GGTCCTGGGA
AGACCAGGAT CAAGCGGTCT TTCTGACGTA ACCAAGAGAT CCGTTGACGA CTTCATCAGC
ACCGAGACCC CCATTGCACT GAACAACCTT CTCTGCAATG TTGGTCCTGA TGGATGTCGT
GCATTTGGCA CATCAGCCGG TGCGGTGATT GCATCTCCCA GCACAATTGA CCCGGACTGT
AAGTTGGATC AATACCGTTG ATCTATGTTT ACCGCATACT GAGACGGAAA CAGACTATTA
CATGTGGACG CGAGACAGCG CTCTTGTTTT CAAGAACCTC GTCGACCGCT TCACCGAAAC
GTACGATGCT GGCCTGCAGC GCCGCATTGA GCAGTACATC ACTGCCCAGG TCACTCTCCA
GGGCCTCTCC AACCCATCGG GATCCCTTAC GGACGGGTCT GGTCTGGGCG AGCCCAAGTT
TGAGCTGACC CTGCAGCCCT TCACCGGCAA CTGGGGTCGA CCGCAGCGCG ATGGCCCAGC
TCTGCGAGCC ATTGCCTTGA TTGGATACTC CAAGTGGCTC ATCAACAACA ACTATCAGTC
AACTGTGTCC AACGTCATCT GGCCGATTGT GCGCAACGAC CTCAACTACG TTGCTCAATA
CTGGTTAGTG ACACTTGCCC TCGAACTACT GCTTGCGTCT AACCTCTTCA TCGTAGGAAC
CAGACTGGCT TTGACCTGTG GGAGGAAGTG AAAGGTAGCT CGTTCTTTAC CATTGCCAAC
CAGCACCGAG GTATGAAGCA CAACGTCCAT ACTCGCCGTC ATTACTTTGA GCATTACTGA
CCACCTCTCC AGCACTTGTC GAGGGTGCTA CTCTTGCCGC TACTCTTGGC CAGTCGGGAA
GCACTTATTC ATCTGTTGCT CCCCAGATCT TGTGCTTCCT CCAACGATTC TGGGTGTCGT
CGGGCGGATA TGTCGACTCC AATAGTATGT CTTCCAAGGC TCGTATGATT GTTAAAGACA
AGTACTAACA GCTGGCCTCT AGTCAACACC AACGAGGGCA GGACTGGCAA GGATGTCAAC
TCCATCCTGA CCTCCATCCA CACCTTGGAT CCCAACCTTG GCTGTGATGC AGGCACCTTC
CAGCCATGCA GTGACAAGGC GCTCTCCAAT CTCAAGGTTG TTGTCGACTC CTTCCGCTCC
ATCTACGGTG TGAACAAGGG CATTCCTGCC GGTGCTGCCG TCGCCATTGG CCGATATGCA
GAGGATGTCT ACTTCAACGG TAACCCTTGG TATCTTGCCA CGTTTGCTGC CGCCGAACAG
CTGTACGATG CCGTCTATGT CTGGAAGAAG ACGGGCTCCA TCACGGTTAC TGCCACCTCC
CTGGCCTTCT TCCAGGAGCT TGTTCCCGGC GTGGCGGCCG GGACCTACGC CAGCAGCTCG
TCGACCTTTA CGAACATCAT CAACGCCGTC TCAACATACG CCGATGGCTT CCTTAGCGAG
GCTGCCAAGT ACGTTCCCGC CGACGGTTCG CTGGCCGAGC AGTTTGACCG CAACAGCGGC
ACTCCGCTGT CCGCCCTTCA CCTGACGTGG TCGTACGCCT CGTTCCTGAC AGCCACGGCC
CGTCGGGCTG GCATCGTGCC CCCATCGTGG GCAAACAGCA GCGCCAGCAC GATTCCCTCG
ACGTGCTCCG GCGCGTCCGT GGTCGGATCC TACTCGCGTC CCACAGCCAC GTCATTCCCT
CCGTCGCAGA CGCCCAAGCC TGGCGTTCCC TCCGGTACGC CCTACACTCC CCTGCCCTGC
GCCACTCCAA CGTCCGTGGC CGTCACCTTC CACGAGCTCG TGTCGACGCA GCTTGGCCAG
ACGGTCAAGG TCGCGGGCAA CGCTCCGGCC CTGGGCAACT GGAGCACGAG CGCCGCCGTG
GCTCTCGATG CCGTCAACTA TGCCGACAAC CACCCGCTGT GGATCGGAAC GGTTGACCTC
GAGGCTGGAG ATGTCGTCGA GTACAAGTAC ATCAATGTCG CCAGGATGG CTCCGTGACC
TGGGAGAGTG ATCCCAATCA CACTTACACG GTTCCTGCGG TGGCTTGTGT GACGCAGGTT
GTCAAGGAGG ACACCTGGCA GTCGTAA
```

*FIG. 8* gDNA Sequence from *Trichoderma konilangbra*, (GA109) - 2139 bp (SEQ ID NO: 15)

```
ATGCACGTCC TGTCGACTGC GGTGCTGCTC GGCTCCGTTG CCGTCCAGAA GGTTCTGGGA
AGACCGGGGT CAAGCGGCCT CTCCGACGTC ACCAAGAGAT CTGTCGACGA TTTCATCAGC
ACCCAGACGC CCATCGCACT GAACAACCTC CTCTGCAATG TTGGCCCTGA CGGATGCCGT
GCATTTGGCA CATCAGCTGG TGCGGTTATT GCATCGCCCA GCACAACTGA CCCAGACTGT
AAGTTGGGCT TGTACCAGTA TATCTACGAG AGTTGTACTG CATAGGTACT GATATCGATA
CAGATTATTA CATGTGGACG CGAGACAGTG CTCTTGTCTT CAAGAACCTT GTCGACCGCT
TCACTGAAAC GTACGATGCG GGCCTGCAGC GCCGCATCGA GCAGTACATT GCTGCCCAGG
TCACTCTCCA GGGCCTCACC AATCCATCTG GTTCTCTCTC AGACGGGTCT GGTCTTGGCG
AGCCCAAGTT TGAGTTAACC CTGAAGCCCT TCACTGGCAA CTGGGGTCGA CCGCAGCGGG
ATGGCCCAGC TCTGCGGGCC ATTGCCTTGA TTGGCTACTC AAAGTGGCTC ATCAACAACA
ACTATCAGTC AACCGTGTCC AGCCTCATCT GGCCTATTGT GCGCAACGAC CTCAACTATG
TTGCGCAGTA CTGGTCAGTG GTTGCTTGCT CTTGTTAACA CTTGTGTCTA ACGTCTTCAC
TTCAGGAACC AAACCGGCTT TGACCTGTGG GAGGAAGTTA ATGGAAGCTC ATTCTTTACC
ACTGCCAACC AGCACCGAGG TATGAAGCCC GACGGCTAAA CTTGCCATCG CTGTATATGA
GAATTACGGA CTAGCTCTCC AGCACTTGTT GAGGGCGCCA CCCTTGCTGC CACTCTCAGC
CAGCCGGCAA GCACTTATTC TTCTGTTGCT CCCCAAATCT TGTGCTTCCT CCAGCGATAT
TGGGTGTCGT CCGGTGGATA CGTCGACTCC AACAGTATGT CTCTTCATGC TCGTGGGTTT
TCGAGAAAGA CAATCACTAA TAGCTTGCGC CTAGTCAACA CCAACGAGGG TAGGACTGGA
AAGGATGCCA ACTCCATTCT CGCTGCTATC CACACCTTTG ATCCCAATCT TGGCCGTGAT
GCAGGCACCT TCCAGCCATG CAGCGACAAA GCTCTCTCCA ACCTCAAGGT CGTTGTCGAC
TCCTTCCGCT CCATCTACGG CGTGAACAAG GGCATTCCCG CTGGTGCTGC CGCCGCCGTT
GGCAGATATC CAGAGGACGT GTACTTCAAC GGAAACCCTT GGTACCTTGC AACTTTTGCT
GCTGCTGAGC AGTTGTACGA TGCCATCTAC GTCTGGAAGA AGACAGGCTC CATCACAGTG
ACTGCCATCT CTCTGGCCTT CTTCCAGGAG CTTGTTCCCG GTGTGGCAGC TGGGACCTAC
TCCAGCAGCC AGTCGACCTT TACGAACATC ATCAACGCCG TGTCCACTTA CGCCGATGGC
TTCATCAGCG AGGCCGCCAA GTACGTCCCC GCCGACGGTT CGCTGGCCGA GCAGTTCGAC
CGCAACAACG GCACTCCTCT GTCCGCCCTC CACCTGACGT GGTCGTACGC CTCGTTCTTG
ACAGCCACGG CCCGCCGGGC TGGCATCGTG CCCCCCTCGT GGGCAAACAG CAGCGCCAGC
TCGATTCCTT CGACATGCTC CGGCGCGTCC GTGGTCGGAT CCTATTCACG TCCCACAGCC
ACGTCATTCC CTCCCTCGCA AACGCCCAAG CCCGGCGTTC CTTCCGGTAC TCCCTACACG
CCCCTGCCCT GCGCTACCCC AGCGTCCGTG CCGTCACCT TCCACGAGCT CGTGTCGACG
CAGCTTGGCC AGACGGTCAA AGTTGCGGGC AGCGCCCCGG CCCTGGGCAA CTGGAGCACG
AGCGCCGCTG TCGCTCTGGA CGCCGTCAAC TACGCCGATA CCATCCCCT GTGGATTGGG
TCGGTCGAAC TTGAGGCTGG AGATGTCGTT GAATACAAGT ACATCAATGT GGGTCAGGAT
GGTTCCGTGA CCTGGGAGAG TGACCCCAAC CACACTTACA CGGTTCCTGC GGTGGCTTGT
GTGACGCAGG TCGTCAAGGA GGACACCTGG CAGTCGTAA
```

FIG. 9 gDNA Sequence from Trichoderma sp., (GA113) - 2088 bp (SEQ ID NO: 28)

```
ATGCATGTCT TGTCAACGGC CGTCCTGCTC GGCTCGGTTG CCGTCCAAAA GGTCCTGGGA
AGACCTGGCG CATCCGACAT TACAAAACGA GCCGTTACTG ACTTCATCAA CTCGGAAACT
CCCATTGCCC TGAACAATCT GATTTGCAAT GTTGGTCCTG ACGGATGCCG TGCTTTTGGC
ACATCGATCG GCGCTGTAGT TGCGTCGCCA AGCACAACTG ACCCAGACTG TAAGCTAGTT
TTTGCATTAT ACTTCCACTA TCGTATATAC AATCTATATA TACAGTGCGC TAACACGAAT
CTAAACAAAG ACTTTTACAT GTGGACTCGA GATAGTGCTC TTGTTTTCAA GACGCTTGTT
GATCGGTTCA CACAGAACTA CGATGCAGGC CTGCAGCGCC GCATCGAGCA GTACATTGCT
GCTCAGGTCA CTCTTCAGGG CATCTCAAAC CCATCTGGTT CCCTCTCAGA CGGGTCTGGC
CTTGGCGAGC CCAAGTTCGA GCTTACCTTG AGCCAGTTCA CTGGCAACTG GGCCGCCCG
CAGCGTGATG GTCCAGCTCT TCGAGCCATT GCCTTGATTG CTATTCAAA GTGGCTCATT
AGCAACAACT ACCAGTCGAC AGTGTCGAAC ATCATTTGGC CCATTGTGCG AAATGATCTC
AACTACGTTG CCCAGTACTG GTCAGTGATT GCTTGTTTTC TTGCCCGCTA TTCACTGGTT
CTTTGCTAAC CTTGACTTTT AGGAACCAAA CTGGATTTGA CCTGTGGGAG GAGGTCAACG
GCAGCTCATT CTTCGCTGTA GCCAACCAGC ACCGAGCACT TGTTGAGGGT GCTACCCTTG
CCACTACTCT TGGCCAGTCG GAAGCAGCT ATTCCACTGT TGCTCCTCAG ATTCTCTGCT
TCCTTCAAAA GTTCTGGTCG CCATCCGGAT ATGTCATCTC AACAGTAAG CTATCAATGC
AGACCAATTT TGTAGATGAA TGCGTATGCT AACACTAGTC GGCGCAGTCA ACAGCAACGA
CGGCAGGACT GGAAAGGATT CCAACTCCAT TCTTACATCT ATTCACACTT TCGATCCCAG
CATTGGCTGC GATGCCGCCA CTTTCCAGCC TTGCAGTGAC AAGGCTCTTT CAAACCTCAA
GGTCTACGTC GACTCCTTCC GCTCCATCTA TGGCGTCAAC TCGGGCATTC CTGCTGGCAC
TGCTGTTGCC GTTGGTAGAT ACCCAGAGGA CGTCTACTTT AACGGAAACC CCTGGTATCT
TTCTACCTTT GCTGTTGCTG AGCAGCTGTA CGACGCCCTG TATGTCTGGA AGAAGACTGG
CTCCATCACC GTCACTTCCA CCTCTCTGGC TTCTTCCAAG AGCTCGTCCC CAGCGTGACA
GCCGGAACCT ACGCCAGCAG CTCGTCTACC TTCACCAGCA TCGTCAACGC CGTATCCACC
TACGCCGATG GATTCGTCAG CGAGGCGGCC AAGTACGTCC CCTCTGATGG TTCTCTCTCC
GAGCAGTTCG ACAAGAACAC CGGCACTCCT CTCTCCGCCG TTCACCTGAC CTGGTCGTAT
GCCTCCTTCC TGACTGCCAC GACCCGTCGC GCTGGCATTG TCCCTCCTTC ATGGATTAGC
AGCGGCGCCA ACACCGTTCC CTCGTCCTGC TCCGGCACGA CAGTGGCTGG TTCCTACTCA
AGTCCCACAG CCACGTCATT CCCTCCGTCA CAGACTCCCA AGACTGCGGC TACTGGTACC
AGCTTCACTC CCATTGCCTG CGCTACCCCA ACTTCCGTGG CTGTGACCTT CCACGAGCTT
GCTACGACCG TCCCCGGCCA GACAATCAAG GTCGTTGGCA ATGCCCAGGC CCTGGGCAAC
TGGAGCACCA GCGCCGGTGT TGCCCTGAAC GCCGTCAACT GTGCTTCCAA CCACCCTCTG
TGGATCGGAC CCGTCAATCT CAAGGCCGGA GACGTCGTCG AGTACAAGTA TATCAACGTG
GGCTCAGACG GCTCCGTGAC TTGGGAGGCC GACCCCAACC ACACTTACAC TGTCCCTGCA
GTGGCCTGTG TTACCGCAGT TGTTAAGGAG GACACCTGGC AGTCGTAA
```

FIG. 10 gDNA Sequence from Trichoderma harzianum, (GA103) - 2141 bp (SEQ ID NO: 30)

```
ATGCATGTGC TGTCGACTGC TGTGCTGCTT GGCTCAGTTG CCGTCCAAAA GGTTCTGGGA
AGGCCAGGAT CGAACGGCCT GTCCGGCGTC ACAAAACGAT CCGTGGATGA CTCCATCAAC
ACACAGACTC CCATTGCACT AAACAACCTC CTTTGCAATG TTGGCCCTGA TGGGTGCCGT
GCCTTTGGTA CATCGGCCGG TGCTGTGATT GCATCTCCGA GCACAACTGA CCCAGACTGT
AAGTTTGACT TATAGCGGCA TATTCCTGAC ATGTCAAATT TCACATACTA ATACGAGGGT
AATTGATCAG ACTACTACAT GTGGACGCGA GACAGTGCTC TTGTCTTCAA GAACATTGTA
GACCGCTTCA CTGAGCAGTA TGATGCTGGC CTGCAGCGCC GCATCGAGCA GTATATTTCT
GCCCAGGTCA CTCTTCAGGG GATCTCAAAC CCCTCTGGTT CTCTCTCGGA TGGGTCTGGT
CTTGGTGAAC CAAGTTTGA GTTGACCTTG AGCCAGTTCA CTGGCAACTG GGGTCGCCCG
CAGCGCGATG GCCCAGCTCT CCGAGCCATT GCCTTGATTG CTATTCAAA GTGGCTCATC
AACAACAACT ACCAGTCAAC GGTGTCAAAC ATCATCTGGC CCATTGTGCG GAATGATCTC
AACTATGTTG CCCAGTACTG GTTAGTACAA GCTCGCTGTC TCTTCGTCTT GTTTATGACT
AATTCTAACA CCTTCACCTT AGGAATCAAA CCGGTTTCGA CCTGTGGGAG GAAGTCAATG
GTAGTTCGTT CTTTACCGTT GCCAACCAGC ACCGAGGTAT GTATCAATAT CTCATGTGTT
TTTAGTTGTC AATGCTGACG AGTCCCCCAG CTCTTGTTGA GGGCGCCACA CTTGCCGCTA
CCCTCGGCCA GTCGGAAGC ACCTATTCCT CTGTTGCTCC TCAGATCCTG TGCTTCCTCC
AAAGATTCTG GGTGTCGGGT GGATACATTG ACTCCAACAG TAAGTACACC AGCACCACAT
GCTTTGATGA AGAGCGATAC TAAACAGCTT GTCATAGTCA ACACCAACGA GGGCAGGACT
GGAAAAGATG CCAACTCTCT TCTCGCATCT ATCCACACGT TCGATCCCAG CCTTGGCTGT
GACGCCTCTA CCTTCCAGCC TTGCAGTGAC AAGGCTCTCT CCAACCTCAA GGTTGTTGTG
GACTCCTTCC GCTCCATCTA CAGTGTCAAC AAGGGCATTC CCGCTGGCGC TGCTGTTGCC
GTCGGCAGAT ACCCCGAAGA CGTGTACTTT AACGGAAACC CCTGGTATCT CGCCACGTTC
GCTGCTGCCG AGCAATTGTA CGACTCCGTC TATGTCTGGA AGAAGACAGG CTCCATCACG
GTGACTTCCA CTTCTTTGGC CTTCTTCCAG GAGCTCGTTC CCGGCGTCGC GGCTGGAACT
TACTCCAGCA GCCAGTCTAC CTTTACGAGC ATCATCAACG CCGTCTCGAC ATATGCTGAT
GGATTCCTCA GCGAGGCTGC CAAGTACGTC CCCGCTGATG GTTCGCTCGC CGAGCAGTTC
GATCGCAACA CCGGCACGCC TCTGTCAGCC GTTCACCTGA CCTGGTCGTA CGCCTCGTTT
CTCACCGCCG CGGCCCGTCG GGCTGGCGTT GTGCCCCCT CGTGGGCCAG CAGCGGCGCT
AACTCAGTCC CTTCAAGCTG CTCGGGAGCT TCTGTGGTTG GATCCTACTC GCGTCCTACA
GCCACGTCAT TCCCACCGTC GCAGACCCCC AAGCCTGGCG CTCCTTCTGG TGCTCCCTTC
ACTCCCATTC CCTGTGCTAC CCCGGCCTCC GTTGCCGTTA CCTTCCACGA GCTTGCCACA
ACCCAATTTG GCCAGACAAT CAAGGTCGCT GGTAGCGCCC CCGAGCTGGG CAACTGGAGC
ACGAGCGCGG CCATTGCTCT GGATGCCGTC AACTATGCCA CTAACCATCC CCTGTGGATT
GGATCGGTCA ATCTGGAGGC CGGAGACGTC ATCGAGTACA AGTACATCAG CGTGGGCCAG
GATGGTTCCG TCACCTGGGA GAGCGACCCC AACCACACCT ACACTGTTCC TGCGGTGGCC
TGTGTCACCG AGGTGGTTAA GGAGGACACC TGGCAGTCGT A
```

FIG. 11 gDNA Sequence from Trichoderma longibrachiatum,
(GA124) - 2131 bp (SEQ ID NO: 32)

```
ATGCACGTCC TGTCGACTGC GGTGCTGCTC GGTTCCGTTG CCGTTCAGAA GGTCCTGGGA
AGGCCAGGAT CAAGCGGTCT ATCTGACGTA ACCAAGAGAT CTGTTGACGA CTTCATCAGC
ACCGAGACTC CTATTGCACT GAACAACCTT CTCTGCAATG TTGGTCCTGA TGGATGTCGT
GCATTTGGCA CATCAGCTGG TGCGGTGATT GCATCTCCCA GCACAATTGA CCCGGACTGT
AAGTGTATCA ATACCGTTGA TCTATGTTTA TCGCATGCTG AGACGGGGAC AGACTATTAC
ATGTGGACGC GAGACAGCGC TCTTGTCTTC AAGAACCTCG TCGACCGCTT CACCGAAACG
TACGATGCTG GCCTGCAGCG CCGCATTGAG CAGTACATCA CTGCCCAGGT CACTCTCCAG
GGCCTCTCCA ACCCATCGGG TTCCCTTACG GACGGATCTG GCCTGGGCGA GCCCAAGTTT
GAGCTGACCC TGAAGCCATT CACCGGCAAC TGGGGTCGAC CGCAGCGCGA CGGCCCAGCT
CTGCGAGCCG TTGCCTTGAT TGGATACTCC AAGTGGCTCA TCAACAACAA CTATCAGTCA
ACTGTGTCCA ACGTCATCTG GCCGATTGTG CGCAACGACC TCAACTACGT TGCTCAGTAC
TGGTTAGTGA TTACTTGCTC TTGAATTACT GCTTGCATCT GACCTCTTTA TCGTAGGAAC
CAGACYGGCT TTGACCTGTG GGAGGAAGTG AATGGAAGCT CGTTCTTTAC CATGGCCAAC
CAGCACCGAG GTATGAAGCA CAACGTCTAT ACTCGCCGTC ATTACATGTG AGCATTACTG
ACCGGCTATC CAGCACTTGT CGAGGGTGCT ACTCTTGCTG CCACTCTTGG CCAGTCGGGA
AGCACTTATT CATCTGTTGC TCCCCAGATC TTGTGCTTCC TCCAACGATT CTGGGTGTCG
TCGGGCGGAT ATGTCGACTC CAACAGTATG TCTTCCACGG CTCGTATGAT TGTTGACAAT
GACAAGTACT AACAGCTCGC TTCTAGTCAA CACCAACGAG GGCAGGACTG CAAGGATGT
CAACTCCGTT CTGACTTCCA TCCACACCTT TGATCCCAAC CTTGGCTGTG ATGCAGCCAC
CTTCCAGCCA TGCAGTGACA AGGCGCTCTC CAATCTCAAG GTTGTTGTCG ACTCCTTCCG
CTCCATCTAC GGCGTGAACA AGGGCATTCC TGCCGGTGCT GCCGTCGCCA TTGGCCGATA
TGCAGAGGAT GTGTACTTCA ACGGTAACCC TTGGTATCTT GCCACGTTTG CTGCCGCCGA
ACAGCTGTAC GATGCCATCT ATGTCTGGAA GAAGACGGGC TCTATCACGG TTACTGCCAC
CTCCCTGGCC TTCTTCCAGG AGCTTGTTCC CGGCGTGGCG GCCGGGACCT ACGCCAGCAG
CTCGTCGACC TTTACGAACA TCATCAACGC CGTCTCGACA TACGCCGATG GCTTCCTCAG
CGAGGCAGCC AAGTACGTTC CCGCCGACGG TTCGCTGGCC GAGCAGTTTG ACCGCAACAG
CGGCACTCCG CTGTCCGCCC TTCACCTGAC GTGGTCGTAC GCCTCGTTCC TGACAGCCAC
GGCCCGTCGG GCTGGCATCG TGCCCCCCTC GTGGGCAAAC AGCAGCGCCA GCACGATCCC
CTCCACGTGC TCCGGCGCGT CCGTGGTCGG ATCCTACTCG CGTCCCACAG CCACGTCATT
CCCTCCGTCG CAGACGCCCA AGCCTGGCGT TCCCTCCGGT ACGCCCTACA CTCCCCTGCC
CTGCGCCACC CCAACGTCCG TGGCCGTCAC CTTCCACGAG CTCGTGTCGA CACAGTTTGG
CCAGACGGTC AAGGTCGCGG GCAACGCTCC GGCCCTCGGC AACTGGAGCG CAAGCGCCGC
CGTGGCTCTC GATGCCATCA ACTATGCCGA CAACCACCCG CTGTGGATCG AACGGTCGA
CCTCGAGGCT GGGGATGTCG TCGAGTACAA GTACATCAAT GTCGGCCAGG ATGGCTCCGT
GACCTGGGAG AGTGACCCCA ACCACACTTA CACGGTTCCT GCGGTGGCCT GTGTGACGCA
GGTTGTCAAG GAGGACACCT GGCAGTCGTA A
```

FIG. 12 gDNA Sequence from Trichoderma asperellum,
(GA127) - 2151 bp (SEQ ID NO: 34)

```
ATGCACGTCC TGTCGACTGC GGTGCTACTT GGCTCAGTTG CCGTCCAAAA GGTTCTGGGA
AGACCAGGAT CAAACGGCCT GTCCGGCGTC ACAAAACGAT CTGTGGATGA CTTTATCAAC
ACACAGACTC CCATTGCTTT AAACAACCTT CTTTGCAATG TTGGCCCTGA TGGATGCCGT
GCCTTTGGTA CATCGGCCGG TGCTGTGATT GCATCTCCGA GCACAACTGA CCCAGACTGT
AAGTTTGACC TATACTGGCA TATTCCTGAT ATGTCAAAGT TCATATACTA ACACGAGGGT
AATTAATCAG ACTACTACAT GTGGACGCGA GATAGTGCTC TTGTCTTCAA GAACATTGTC
GACCGCTTCA CTCAGCAGTA TGATGCCGGC CTGCAGCGCC GCATCGAGCA GTACATTTCT
GCCCAGGTCA CTCTTCAGGG CATCTCAAAC CCCTCTGGCT CTCTCTCGGA CGGATCCGGT
CTTGGTGAAC CAAGTTTGA GTTGACCTTG AGCCAGTTCA CTGGCAACTG GGGTCGCCCG
CAGCGCGATG GCCCAGCTCT CCGAGCCATT GCCTTGATTG GTTATTCGAA GTGGCTCATC
AACAACAACT ACCAGTCAAC GGTGTCAAAT ATCATCTGGC CCATTGTGCG GAATGACCTC
AACTATGTTG CTCAATACTG GTTAGTACAA GCTCGCTGTC TTTTCGTTCG TTTATGATTG
ATTCTAACAT CTTCACTTCA GGAACCAAAC CGGATTCGAT CTGTGGGAGG AAGTTAATGG
TAGCTCGTTC TTTACCGTTG CCAACCAGCA CCGAGGTATG TATCAACATC TCATGTGCAA
TTTTTAGTTG GAAATAAACA ATACTGACGA GTTCTCCAGC TCTTGTTGAG GGCGCCACAC
TTGCTGCCAC CCTCGGCCAG TCGGGAAGCA CCTATTCCTC AGTTGCGCCT CAGATCCTGT
GCTTCCTCCA GAGGTTCTGG GTGTCGGGTG GATACATTGA CTCCAACAGT AAGTCCACCA
GCACCATATG CTTTGATGAA GGGCGATACT AAACAGCTTG CTATAGTCAA CACCAACGAG
GGCAGGACTG GAAAAGATGC CAACTCTCTT CTCGCATCTA TCCACACGTT CGATCCTAGC
CTTGGCTGTG ACGCCTCCAC CTTCCAGCCT TGCAGTGACA AAGCCCTCTC CAACCTCAAG
GTCGTTGTAG ACTCCTTCCG CTCCATCTAC GGTGTCAACA AGGGCATTCC CGCTGGCTCT
GCTGTCGCCA TCGGCAGATA CCCCGAAGAC GTGTACTTTA ACGGAAACCC CTGGTATCTC
GCTACGTTCG CTGCTGCCGA GCAACTTTAC GACTCCGTCT ATGTCTGGAA GAAGACAGGC
TCCATCACGG TGACTTCCAC TTCTTTGGCC TTCTTCCAGG AGCTCGTTCC CGGCGTCGCG
GCTGGAACTT ACTCCAGCAG CCAGTCTACC TTCACGAGCA TCATCAACGC CGTCTCGACA
TATGCTGATG GATTCCTCAG CGAGGCTGCC AAGTACGTCC CCGCTGATGG TTCGCTCGCC
GAGCAGTTCG ATCGCAACAC CGGCACACCT CTGTCAGCCG TTCACCTGAC CTGGTCGTAC
GCCTCGTTTC TCACCGCCGC GGCCCGTCGG GCTGGCGTTG TCCCCCCCTC ATGGGCCAGC
AGCGGCGCTA ACTCAGTTCC TTCAAGCTGC TCGGGAGCTT CTGTGGTTGG ATCCTACTCG
CGTCCTACAG CCACGTCATT CCCACCATCG CAGACCCCCA AGCCTGGCGT TCCTTCTGGT
ACTCCCTTCA CTCCCATTCC CTGTGCTACC CCGACTTCCG TTGCTGTCAC TTTCCACGAG
CTTGCCACAA CGCAGTTTGG TCAGACTATC AAGGTCGCTG GTAGCGCTCC CGAGCTGGGC
AACTGGAGCA CGAGCGCGGC CATTGCTCTG GATGCCGTCA ACTATGCCAC TAACCACCCT
CTGTGGATTG GATCAGTCAG TCTGGAGGCC GGAGACGTTA TCGAGTACAA GTACATCAAC
GTGGGCCAGG ATGGTTCCGT CACCTGGGAG AGCGATCCCA ACCACACCTA CACTGTCCCT
GCGGTGGCCT GTGTCACTGA GGTGGTTAAG GAGGACACCT GGCAGTCGTA A
```

FIG. 13 gDNA Sequence from Trichoderma strictipilis, (GA128) - 2142 bp  (SEQ ID NO: 36)

```
ATGCACGTCC TGTCGACTGC GGTGCTGCTC GGCTCCGTTG CCGTTCAAAA GGTCCTGGGA
AGACCGGGAT CAAGCGGTCT ATCTGACATC ACCAAGAGAT CCGTCGACGA CTTCATCAGC
ACCCAGACTC CTATTGCACT GAACAACCTT CTCTGCAATG TTGGTCCCGA TGGATGTCGT
GCATTTGGCA CATCCGCTGG TGCGGTTATT GCATCCCCCA GCACAACTGA CCCCGACTGT
AAGTTGGAAC TGTTACCGGC ATAAACCCAC AGGATGTGTA TCGCATACTG AGATCGAGAC
AGACTATTAC ATGTGGACGC GAGACAGCGC TCTTGTCTTC AAGAACCTTG TCGACCGCTT
CACCGAAACG TACGATGCTG GCCTGCAGCG CCGCATCGAG CAGTACATTA CTGCCCAGGT
CACTCTCCAG GGCCTCACCA ACCCATCAGG TTCCCTCGCG GACGGGTCTG GCCTTGGCGA
GCCCAAGTTT GAGTTGACCC TGAGTCCTTT CACCGGCAAC TGGGGTCGAC CGCAGCGGGA
TGGCCCAGCT CTGCGAGCCA TTGCCTTGAT TGGCTATTCG AAATGGCTTA TCAACAACAA
CTATCAGTCA ACCGTGTCCA ACGTCATCTG GCCTATTGTG CGCAACGACC TCAGCTACGC
TGCTCAGTAC TGGTTAGTGA CAGCTTACCC TCGAATTACG GCTCGTGTCT AACGTCTTCA
CTACAGGAAC CAGACCGGCT TGATCTGTG GGAAGAGGTT AGCGGAAGCT CTTTTTTTAC
TGTTGCCAAC CAGCACCGAG GTATGAAGCA AAACGTCCAC ACTCACTGTC ACTGTATATG
AACGCTACTG ACCAGCTCCC CAGCTCTTGT TGAGGGTGCC ACGTTGCTG CCACGCTCGG
CCAGTCGGGA AGCACTTATT CATCTGTTGC TCCCCAAATC TTGTGCTTTC TCCAACGATT
CTGGGTGTCG TCCGGTGGAT ACGTCGACTC CAACAGTATG TCCTTCGCTG CTCATGGATT
TGGAAAGTTT CTGTTACTAA TGCCAGCTCG CCTCTAGTCA ACACGAATGA GGGTAGGACT
GGAAAGGATG TCAACTCCAT TCTCACTTCC ATCCACACCT TCGATCCCAA CCTTGGCTGT
GACGCAGGCA CCTTCCAGCC ATGCAGTGAC AAAGCCCTCT CCAACTTCAA GGTTGTTGTC
GACTCCTTCC GCTCCATCTA CGGCGTGAAC AACGGCATTC CTGCTGGTGC TGCCGTCGCC
ATTGGCAGAT ATCCAGAGGA TGTGTACTTC AACGGGAACC CTTGGTACCT TGCCACGTTT
GCTGCTGCTG AGCAGCTGTA CGACGCCATC TACGTCTGGA AGAAGACGGG CTCCATCACA
GTGACTGCCA TCTCTCTCGC CTTCTTCCAG GAGCTTGTTC CCGGCGTGAC AGCTGGGACC
TACTCCAGCA GCCAGTCGAC TTTCACCAAC ATCATCAACG CTGCCTCGAC ATACGCCGAT
GGCTTCGTCA CCGAGGCTGC CAAGTACGTT CCCACCGACG GTTCGCTGGC CGAGCAGTTC
GACCGCAACA ACGGCACTCC GCTGTCCGCC CTTCACCTGA CGTGGTCGTA CGCCTCGTTC
TTGACTGCTT CGGCCCGTCG GGCTGGCGTC GTGCCCCCCT CGTGGGCAAA CAGCAGTGCC
AGCTCGATTT CTTCGACGTG CTCCGGCGCG TCCGTGGTCG GATCCTACTC GAGTCCCACA
GCCACGTCAT TCCCTCCGTC GCAGACGCCC AAGCCCGGCG TTCCTTCCGG TACCCCCTAC
ACGCCCCTGC CCTGCGCTAC CCCAACGTCC GTGGCCGTCA CCTTCCACGA GCTCGTGTCG
ACACAGTTTG GCCAGACGGT CAAGGCCGCG GGCAGCGCTC CGGCCCTGGG CAACTGGAGC
ACGAGCGCGG CTGTCGGTCT GGACGCCGTC AACTACGCCG ATAACCACCC CCTGTGGATT
GGGACGGTCG AGCTGGAGGC TGGAGACGTC GTTGAGTACA AGTACATCAA TGTGGGTCAG
GATGGCTCCG TGACCTGGGA GAGTGACCCC AACCACACTT ACACGGTTCC TGCGGTGGCT
TGTGTGACGG AGGTCGTCAA GGAGGACACC TGGCAGTCGT AA
```

FIG. 14

1a) Putative amino acid sequence of the Hypocrea citrina var. americana (CBS976.69) glucoamylase, (GA102) having 632 AA (SEQ ID NO: 6), wherein the mature protein sequence is represented by amino acid residue positions 34 – 632 (SEQ ID NO: 17).

MHVLSTAVLL GLVAVQKVLG <u>RPGLNGVPDV</u> <u>TKR</u>SVDDFIS NESPIALNNL LCNVGPDGCR
AFGASAGTVA ASPSTTDPDY YYMWTRDSAL IFKTVVDRFT QNYDASLQKR IEQYIAAQAT
LQGISNPSGS LADGSGLGEP KFELTLNQFT GHWGRPQRDG PALRAIALIG YSKWLIDNNY
QSTVSDIIWP ILRNDLNYVA QYWNQTGFDL WEEVEGSSFF TVANQHRALV EGATLAAILG
QSGSSYSAVA PQILCFLQKF WVSSGGYVNS NINSDINRTG KDANSLLASI HTFDPSIGCD
PATFQPCSDK ALSNLKSVVD SFRSIYGVNQ GISAGSAVAI GRYSEDVYFN GNPWYLATFA
AAEQLYDSLY VWKQTGSITV TAIPLAFFQE LVPGVAAGTY LSSQSTFTSI VNAVSAYADG
FLNEAAKYVP SDGSLAEQFD KNNGTPLSAV HLTWSYASFL TATARRAGSV PPSWANSNAT
SIPTACSGTS VVGSYSSPTA TSFPPSQTPK VGKPTGTPFT PIPCATPTSV AVTFHELPTT
QFGQTIKLAG SAEALGNWST GAAVGLDAAN YASNHPLWFG TLNLQAGDVI EYKYINVGKD
GSVTWESDPN HTYTVPAVAC VTEVVKEDTW QS

FIG. 15A

1b) Mature protein sequence for GA102 (SEQ ID NO: 17)

SVDDFISNESPIALNNLLCNVGPDGCRAFGASAGTVAASPSTTDPDYYYMWTRDSALIFKTVVDRFTQNYD
ASLQKRIEQYIAAQATLQGISNPSGSLADGSGLGEPKFELTLNQFTGHWGRPQRDGPALRAIALIGYSKWL
IDNNYQSTVSDIIWPILRNDLNYVAQYWNQTGFDLWEEVEGSSFFTVANQHRALVEGATLAAILGQSGSSY
SAVAPQILCFLQKFWVSSGGYVNSNINSDINRTGKDANSLLASIHTFDPSIGCDPATFQPCSDKALSNLKS
VVDSFRSIYGVNQGISAGSAVAIGRYSEDVYFNGNPWYLATFAAAEQLYDSLYVWKQTGSITVTAIPLAFF
QELVPGVAAGTYLSSQSTFTSIVNAVSAYADGFLNEAAKYVPSDGSLAEQFDKNNGTPLSAVHLTWSYASF
LTATARRAGSVPPSWANSNATSIPTACSGTSVVGSYSSPTATSFPPSQTPKVGKPTGTPFTPIPCATPTSV
AVTFHELPTTQFGQTIKLAGSAEALGNWSTGAAVGLDAANYASNHPLWFGTLNLQAGDVIEYKYINVGKDG
SVTWESDPNHTYTVPAVACVTEVVKEDTWQS

FIG. 15B

2a) Putative amino acid sequence of the Hypocrea vinosa (CBS960.68) glucoamylase, (GA104) having 631 AA (SEQ ID NO: 8), wherein the mature protein sequence is represented by amino acid residue positions 34 – 631 (SEQ ID NO: 18).

MHVLSTAVLL GSVAVQKVLG RPGSNGLSGV TKRSVDDFIN TQTPIALNNL LCNVGPDGCR
AFGTSAGAVI ASPSTTDPDY YYMWTRDSAL VFKNIVDRFT QQYDAGLQRR IEQYISAQVT
LQGISNPSGS LSDGSGLGEP KFELTLSQFT GNWGRPQRDG PALRAIALIG YSKWLINNNY
QSTVSNIIWP IVRNDLNYVA QYWNQTGFDL WEEVNGSSFF TVANQHRALV EGATLAATLG
QSGSTYSSVA PQILCFLQRF WVSGGYIDSN INTNEGRTGK DANSLLASIH TFDPSLGCDA
STFQPCSDKA LSNLKVVVDS FRSIYGVNKG IPAGSAVAIG RYPEDVYFNG NPWYLATFAA
AEQLYDSVYV WKKTGSITVT STSSAFFQEL VPGVAAGTYS SSQSTFTSII NAISTYADGF
LSEAAKYVPA DGSLAEQFDR NTGTPLSAVH LTWSYASFLT AAARRAGVVP PSWASSGANT
VPSSCSGASV VGSYSRPTAT SFPPSQTPKP GVPSGTPFTP IPCATPTSVA VTFHELATTQ
FGQTIKVAGS APELGNWSTS AAIALDAVNY ATNHPLWIGS VNLEAGDVIE YKYINVGQDG
SVTWESDPNH TYTVPAVACV TEVVKEDTWQ S

FIG. 15C

1b) Mature protein sequence for GA104 (SEQ ID NO: 18).

SVDDFINTQTPIALNNLLCNVGPDGCRAFGTSAGAVIASPSTTDPDYYYMWTRDSALVFKNIVDRFTQQYD
AGLQRRIEQYISAQVTLQGISNPSGSLSDGSGLGEPKFELTLSQFTGNWGRPQRDGPALRAIALIGYSKWL
INNNYQSTVSNIIWPIVRNDLNYVAQYWNQTGFDLWEEVNGSSFFTVANQHRALVEGATLAATLGQSGSTY
SSVAPQILCFLQRFWVSGGYIDSNINTNEGRTGKDANSLLASIHTFDPSLGCDASTFQPCSDKALSNLKVV
VDSFRSIYGVNKGIPAGSAVAIGRYPEDVYFNGNPWYLATFAAAEQLYDSVYVWKKTGSITVTSTSSAFFQ
ELVPGVAAGTYSSSQSTFTSIINAISTYADGFLSEAAKYVPADGSLAEQFDRNTGTPLSAVHLTWSYASFL
TAAARRAGVVPPSWASSGANTVPSSCSGASVVGSYSRPTATSFPPSQTPKPGVPSGTPFTPIPCATPTSVA
VTFHELATTQFGQTIKVAGSAPELGNWSTSAAIALDAVNYATNHPLWIGSVNLEAGDVIEYKYINVGQDGS
VTWESDPNHTYTVPAVACVTEVVKEDTWQS

FIG. 15D

3a) Putative amino acid sequence of the *Trichoderma sp.* glucoamylase, (GA105) having 633 AA (SEQ ID NO: 10), wherein the mature protein sequence is represented by amino acid residue positions 34 – 633 (SEQ ID NO: 19).

MHVLSTAVLL GSVAVQKVLG RPGSSGLYDV TKRSVDDFIS TETPIALNNL LCNVGPDGCR
AFGTSAGAVI ASPSTTDPDY YYMWTRDSAL VFKNLVDRFT EEYDAGLQRR IEQYITAQVT
LQGLTNPSGS LSDGSGLGEP KFELTLQPFT GNWGRPQRDG PALRAIALIG YAKWLINNNY
QSTVSSVIWP IVRNDLNYVA QYWNQTGFDL WEEVDGSSFF TVANQHRALV EGATLVATLG
QSGDTYSSVA PQVLCFLQRF WVSSGGYIDS NINTNEGRTG KDANSILTSI HTFDPNLGCD
AGTFQPCSDK ALSNLKVVVD SFRSIYSLNK GIPAGAAVAI GRYPEDVYFN GNPWYLATFA
AAEQLYDAVY VWKETGSITV TATSLAFFQE LVPGVTAGTY SSSSSSTFTT IINAVSTYAD
GFLSEAAKYV PADGSLAEQF DRNNGTALSA RHLTWSYASF LTATARRAGV VPPSWANSSA
STIPSTCSGA SVVGSYSRPT ATSFPPSQTP KPGVPSGTPY TPLPCATPTS VAVTFHELVS
TQFGQTVKVA GSAQALGNWS TSAAVALDAV NYADNHPLWI GTVNLEAGDV VEYKYINVGQ
DGSVTWESDP NHTYTVPAVA CVTQVVKEDT WQS

FIG. 15E

3b) Mature protein sequence for GA105 (SEQ ID NO: 19).

SVDDFISTETPIALNNLLCNVGPDGCRAFGTSAGAVIASPSTTDPDYYYMWTRDSALVFKNLVDRFTEEYD
AGLQRRIEQYITAQVTLQGLTNPSGSLSDGSGLGEPKFELTLQPFTGNWGRPQRDGPALRAIALIGYAKWL
INNNYQSTVSSVIWPIVRNDLNYVAQYWNQTGFDLWEEVDGSSFFTVANQHRALVEGATLVATLGQSGDTY
SSVAPQVLCFLQRFWVSSGGYIDSNINTNEGRTGKDANSILTSIHTFDPNLGCDAGTFQPCSDKALSNLKV
VVDSFRSIYSLNKGIPAGAAVAIGRYPEDVYFNGNPWYLATFAAAEQLYDAVYVWKETGSITVTATSLAFF
QELVPGVTAGTYSSSSSSTFTTIINAVSTYADGFLSEAAKYVPADGSLAEQFDRNNGTALSARHLTWSYAS
FLTATARRAGVVPPSWANSSASTIPSTCSGASVVGSYSRPTATSFPPSQTPKPGVPSGTPYTPLPCATPTS
VAVTFHELVSTQFGQTVKVAGSAQALGNWSTSAAVALDAVNYADNHPLWIGTVNLEAGDVVEYKYINVGQD
GSVTWESDPNHTYTVPAVACVTQVVKEDTWQS

FIG. 15F

4) Putative amino acid sequence for the Hypocrea gelatinosa (CBS254.62) glucoamylase, (GA107) having 631 AA (SEQ ID NO: 12), wherein the mature protein sequence is represented by amino acid residue positions 34 – 631 (SEQ ID NO: 20).

```
MHVLSTAVLL GSVAVQKVLG RPGSNGLSGV TKRSVDDFIN TQTPIALNNL LCNVGPDGCR
AFGTSAGAVI ASPSTTDPDY YYMWTRDSAL VFKNIVDRFT QQYDAGLQRR IEQYISAQVT
LQGPSNPSGS LSDGSGLGEP KFELTLSQFT GNWGRPQRDG PALRAIALIG YSKWLINNNY
QSTVSSIIWP IVRNDLNYVA QYWNQTGFDL WEEVNGSSFF TVANQHRALV EGATLAATLG
QSGSTYSSVA PQILCFLQRF WVSGGYIDSN INSNDGRTGK DANSLLASIH TFDPSLGCDA
STFQPCSDKA LSNLKVVVDS FRSIYGVNKG ISAGSAVAIG RYPEDVYFNG NPWYLATFAA
AEQLYDSVYV WKKTGSITVT STSLAFFQEL VPGVAAGTYS SSQSTFTSIV NAVSTYADGF
LSEAAKYVPA DGSLAEQFDR NTGTPLSAVH LTWSYASFFT AAARRSGVVP PSWASSGANS
IPATCSGASV VGSYSSPTAT SFPPSQTPKP GVPSGTPFTP LPCATPTSVA VTFHELATTQ
FGQNIKVAGS APELGNWSTS AAIALDAVNY ATNHPLWIGS VNLEAGDVIE YKYINVGQDG
SVTWESDPNH TYTVPAVACV TEVVKEDTWQ S
```

FIG. 15G

4b) Mature protein sequence for GA107 (SEQ ID NO: 20).

```
SVDDFINTQTPIALNNLLCNVGPDGCRAFGTSAGAVIASPSTTDPDYYYMWTRDSALVFKNIVDRFTQQYD
AGLQRRIEQYISAQVTLQGPSNPSGSLSDGSGLGEPKFELTLSQFTGNWGRPQRDGPALRAIALIGYSKWL
INNNYQSTVSSIIWPIVRNDLNYVAQYWNQTGFDLWEEVNGSSFFTVANQHRALVEGATLAATLGQSGSTY
SSVAPQILCFLQRFWVSGGYIDSNINSNDGRTGKDANSLLASIHTFDPSLGCDASTFQPCSDKALSNLKVV
VDSFRSIYGVNKGISAGSAVAIGRYPEDVYFNGNPWYLATFAAAEQLYDSVYVWKKTGSITVTSTSLAFFQ
ELVPGVAAGTYSSSQSTFTSIVNAVSTYADGFLSEAAKYVPADGSLAEQFDRNTGTPLSAVHLTWSYASFF
TAAARRSGVVPPSWASSGANSIPATCSGASVVGSYSSPTATSFPPSQTPKPGVPSGTPFTPLPCATPTSVA
VTFHELATTQFGQNIKVAGSAPELGNWSTSAAIALDAVNYATNHPLWIGSVNLEAGDVIEYKYINVGQDG
SVTWESDPNHTYTVPAVACVTEVVKEDTWQS
```

FIG. 15H

5a) Putative amino acid sequence for the Hypocrea orientalis (ATCC90550) glucoamylase, (GA108) having 632 AA (SEQ ID NO: 14), wherein the mature protein sequence is represented by amino acid residue positions 34 – 632 (SEQ ID NO: 21).

MHVLSTAVLL GSVAVQKVLG RPGSSGLSDV TKRSVDDFIS TETPIALNNL LCNVGPDGCR
AFGTSAGAVI ASPSTIDPDY YYMWTRDSAL VFKNLVDRFT ETYDAGLQRR IEQYITAQVT
LQGLSNPSGS LTDGSGLGEP KFELTLQPFT GNWGRPQRDG PALRAIALIG YSKWLINNNY
QSTVSNVIWP IVRNDLNYVA QYWNQTGFDL WEEVKGSSFF TIANQHRALV EGATLAATLG
QSGSTYSSVA PQILCFLQRF WVSSGGYVDS NINTNEGRTG KDVNSILTSI HTLDPNLGCD
AGTFQPCSDK ALSNLKVVVD SFRSIYGVNK GIPAGAAVAI GRYAEDVYFN GNPWYLATFA
AAEQLYDAVY VWKKTGSITV TATSLAFFQE LVPGVAAGTY ASSSSTFTNI INAVSTYADG
FLSEAAKYVP ADGSLAEQFD RNSGTPLSAL HLTWSYASFL TATARRAGIV PPSWANSSAS
TIPSTCSGAS VVGSYSRPTA TSFPPSQTPK PGVPSGTPYT PLPCATPTSV AVTFHELVST
QLGQTVKVAG NAPALGNWST SAAVALDAVN YADNHPLWIG TVDLEAGDVV EYKYINVGQD
GSVTWESDPN HTYTVPAVAC VTQVVKEDTW QS

*FIG. 15I*

5b) Mature protein sequence for GA108 (SEQ ID NO: 21).

SVDDFISTETPIALNNLLCNVGPDGCRAFGTSAGAVIASPSTIDPDYYYMWTRDSALVFKNLVDRFTETYD
AGLQRRIEQYITAQVTLQGLSNPSGSLTDGSGLGEPKFELTLQPFTGNWGRPQRDGPALRAIALIGYSKWL
INNNYQSTVSNVIWPIVRNDLNYVAQYWNQTGFDLWEEVKGSSFFTIANQHRALVEGATLAATLGQSGSTY
SSVAPQILCFLQRFWVSSGGYVDSNINTNEGRTGKDVNSILTSIHTLDPNLGCDAGTFQPCSDKALSNLKV
VVDSFRSIYGVNKGIPAGAAVAIGRYAEDVYFNGNPWYLATFAAAEQLYDAVYVWKKTGSITVTATSLAFF
QELVPGVAAGTYASSSSTFTNIINAVSTYADGFLSEAAKYVPADGSLAEQFDRNSGTPLSALHLTWSYASF
LTATARRAGIVPPSWANSSASTIPSTCSGASVVGSYSRPTATSFPPSQTPKPGVPSGTPYTPLPCATPTSV
AVTFHELVSTQLGQTVKVAGNAPALGNWSTSAAVALDAVNYADNHPLWIGTVDLEAGDVVEYKYINVGQD
GSVTWESDPNHTYTVPAVACVTQVVKEDTWQS

*FIG. 15J*

6a) Putative amino acid sequence of the Trichoderma konilangbra glucoamylase, (GA109) having 632 AA (SEQ ID NO: 16), wherein the mature protein sequence is represented by amino acid residue positions 34 – 632 (SEQ ID NO: 22).

MHVLSTAVLL GSVAVQKVLG RPGSSGLSDV TKRSVDDFIS TQTPIALNNL LCNVGPDGCR
AFGTSAGAVI ASPSTTDPDY YYMWTRDSAL VFKNLVDRFT ETYDAGLQRR IEQYIAAQVT
LQGLTNPSGS LSDGSGLGEP KFELTLKPFT GNWGRPQRDG PALRAIALIG YSKWLINNNY
QSTVSSLIWP IVRNDLNYVA QYWNQTGFDL WEEVNGSSFF TTANQHRALV EGATLAATLS
QPASTYSSVA PQILCFLQRY WVSSGGYVDS NINTNEGRTG KDANSILAAI HTFDPNLGRD
AGTFQPCSDK ALSNLKVVVD SFRSIYGVNK GIPAGAAAAV GRYPEDVYFN GNPWYLATFA
AAEQLYDAIY VWKKTGSITV TAISLAFFQE LVPGVAAGTY SSSQSTFTNI INAVSTYADG
FISEAAKYVP ADGSLAEQFD RNNGTPLSAL HLTWSYASFL TATARRAGIV PPSWANSSAS
SIPSTCSGAS VVGSYSRPTA TSFPPSQTPK PGVPSGTPYT PLPCATPASV AVTFHELVST
QLGQTVKVAG SAPALGNWST SAAVALDAVN YADNHPLWIG SVELEAGDVV EYKYINVGQD
GSVTWESDPN HTYTVPAVAC VTQVVKEDTW QS

FIG. 15K

6b) Mature protein sequence for GA109 (SEQ ID NO: 22).

SVDDFISTQTPIALNNLLCNVGPDGCRAFGTSAGAVIASPSTTDPDYYYMWTRDSALVFKNLVDRFTETYD
AGLQRRIEQYIAAQVTLQGLTNPSGSLSDGSGLGEPKFELTLKPFTGNWGRPQRDGPALRAIALIGYSKWL
INNNYQSTVSSLIWPIVRNDLNYVAQYWNQTGFDLWEEVNGSSFFTTANQHRALVEGATLAATLSQPASTY
SSVAPQILCFLQRYWVSSGGYVDSNINTNEGRTGKDANSILAAIHTFDPNLGRDAGTFQPCSDKALSNLKV
VVDSFRSIYGVNKGIPAGAAAAVGRYPEDVYFNGNPWYLATFAAAEQLYDAIYVWKKTGSITVTAISLAFF
QELVPGVAAGTYSSSQSTFTNIINAVSTYADGFISEAAKYVPADGSLAEQFDRNNGTPLSALHLTWSYASF
LTATARRAGIVPPSWANSSASSIPSTCSGASVVGSYSRPTATSFPPSQTPKPGVPSGTPYTPLPCATPASV
AVTFHELVSTQLGQTVKVAGSAPALGNWSTSAAVALDAVNYADNHPLWIGSVELEAGDVVEYKYINVGQD
GSVTWESDPNHTYTVPAVACVTQVVKEDTWQS

FIG. 15L

7a) Putative amino acid sequence of the Trichoderma sp. (DAOM177690) glucoamylase, (GA113) having 627 AA (SEQ ID NO: 29), wherein the mature protein sequence is represented by amino acid residue 31 – 627 (SEQ ID NO: 43).

MHVLSTAVLL GSVAVQKVLG <u>RPGASDITKR</u> AVTDFINSET PIALNNLICN VGPDGCRAFG
TSIGAVVASP STTDPDYFYM WTRDSALVFK TLVDRFTQKY DAGLQRRIEQ YIAAQVTLQG
ISNPSGSLSD GSGLGEPKFE LTLSQFTGNW GRPQRDGPAL RAIALIGYSK WLISNNYQST
VSNIIWPIVR NDLNYVAQYW NQTGFDLWEE VNGSSFFAVA NQHRALVEGA TLATTLGQSG
SSYSTVAPQI LCFLQKFWSP SGYVISNINS NDGRTGKDSN SILTSIHTFD PSIGCDAATF
QPCSDKALSN LKVYVDSFRS IYGVNSGIPA GTAVAVGRYP EDVYFNGNPW YLSTFAVAEQ
LYDALYVWKK TGSITVTSTS LAFFQELVPS VTAGTYASSS STFTSIVNAV STYADGFVSE
AAKYVPSDGS LSEQFDKNTG TPLSAVHLTW SYASFLTATT RRAGIVPPSW ISSGANTVPS
SCSGTTVAGS YSSPTATSFP PSQTPKTAAT GTSFTPIACA TPTSVAVTFH ELATTVPGQT
IKVVGNAQAL GNWSTSAGVA LNAVNCASNH PLWIGPVNLK AGDVVEYKYI NVGSDGSVTW
EADPNHTYTV PAVACVTAVV KEDTWQS

FIG. 15M

7b) Mature protein sequence for GA113 (SEQ ID NO: 43).

AVTDFINSETPIALNNLICNVGPDGCRAFGTSIGAVVASPSTTDPDYFYMWTRDSALVFKTLVDRFTQKY
DAGLQRRIEQYIAAQVTLQGISNPSGSLSDGSGLGEPKFELTLSQFTGNWGRPQRDGPALRAIALIGYSK
WLISNNYQSTVSNIIWPIVRNDLNYVAQYWNQTGFDLWEEVNGSSFFAVANQHRALVEGATLATTLGQSG
SSYSTVAPQILCFLQKFWSPSGYVISNINSNDGRTGKDSNSILTSIHTFDPSIGCDAATFQPCSDKALSN
LKVYVDSFRSIYGVNSGIPAGTAVAVGRYPEDVYFNGNPWYLSTFAVAEQLYDALYVWKKTGSITVTSTS
LAFFQELVPSVTAGTYASSSSTFTSIVNAVSTYADGFVSEAAKYVPSDGSLSEQFDKNTGTPLSAVHLTW
SYASFLTATTRRAGIVPPSWISSGANTVPSSCSGTTVAGSYSSPTATSFPPSQTPKTAATGTSFTPIACA
TPTSVAVTFHELATTVPGQTIKVVGNAQALGNWSTSAGVALNAVNCASNHPLWIGPVNLKAGDVVEYKYI
NVGSDGSVTWEADPNHTYTVPAVACVTAVVKEDTWQS

FIG. 15N

8a) Putative amino acid sequence of the Trichoderma harzianum (CBS433.95) glucoamylase, (GA103) having 631 AA (SEQ ID NO: 31), wherein the mature protein sequence is represented by amino acid residue 34 – 631 (SEQ ID NO: 44).

MHVLSTAVLL GSVAVQKVLG RPGSNGLSGV TKRSVDDSIN TQTPIALNNL LCNVGPDGCR
AFGTSAGAVI ASPSTTDPDY YYMWTRDSAL VFKNIVDRFT EQYDAGLQRR IEQYISAQVT
LQGISNPSGS LSDGSGLGEP KFELTLSQFT GNWGRPQRDG PALRAIALIG YSKWLINNNY
QSTVSNIIWP IVRNDLNYVA QYWNQTGFDL WEEVNGSSFF TVANQHRALV EGATLAATLG
QSGSTYSSVA PQILCFLQRF WVSGGYIDSN INTNEGRTGK DANSLLASIH TFDPSLGCDA
STFQPCSDKA LSNLKVVVDS FRSIYSVNKG IPAGAAVAVG RYPEDVYFNG NPWYLATFAA
AEQLYDSVYV WKKTGSITVT STSLAFFQEL VPGVAAGTYS SSQSTFTSII NAVSTYADGF
LSEAAKYVPA DGSLAEQFDR NTGTPLSAVH LTWSYASFLT AAARRAGVVP PSWASSGANS
VPSSCSGASV VGSYSRPTAT SFPPSQTPKP GAPSGAPFTP IPCATPASVA VTFHELATTQ
FGQTIKVAGS APELGNWSTS AAIALDAVNY ATNHPLWIGS VNLEAGDVIE YKYISVGQDG
SVTWESDPNH TYTVPAVACV TEVVKEDTWQ S

FIG. 15O

8b) Mature protein sequence for GA103 (SEQ ID NO: 44).

SVDDSINTQTPIALNNLLCNVGPDGCRAFGTSAGAVIASPSTTDPDYYYMWTRDSALVFKNIVDRFTEQYD
AGLQRRIEQYISAQVTLQGISNPSGSLSDGSGLGEPKFELTLSQFTGNWGRPQRDGPALRAIALIGYSKWL
INNNYQSTVSNIIWPIVRNDLNYVAQYWNQTGFDLWEEVNGSSFFTVANQHRALVEGATLAATLGQSGSTY
SSVAPQILCFLQRFWVSGGYIDSNINTNEGRTGKDANSLLASIHTFDPSLGCDASTFQPCSDKALSNLKVV
VDSFRSIYSVNKGIPAGAAVAVGRYPEDVYFNGNPWYLATFAAAEQLYDSVYVWKKTGSITVTSTSLAFFQ
ELVPGVAAGTYSSSQSTFTSIINAVSTYADGFLSEAAKYVPADGSLAEQFDRNTGTPLSAVHLTWSYASFL
TAAARRAGVVPPSWASSGANSVPSSCSGASVVGSYSRPTATSFPPSQTPKPGAPSGAPFTPIPCATPASVA
VTFHELATTQFGQTIKVAGSAPELGNWSTSAAIALDAVNYATNHPLWIGSVNLEAGDVIEYKYISVGQDGS
VTWESDPNHTYTVPAVACVTEVVKEDTWQS

FIG. 15P

9a) Putative amino acid sequence of the Trichoderma longibrachiatum (IMI92.027) glucoamylase, (GA124) – 632 AA (SEQ ID NO: 33), wherein the mature protein sequence is represented by amino acid residue 34 – 632 (SEQ ID NO: 45).

| | | | | | |
|---|---|---|---|---|---|
| MHVLSTAVLL | GSVAVQKVLG | RPGSSGLSDV | TKRSVDDFIS | TETPIALNNL | LCNVGPDGCR |
| AFGTSAGAVI | ASPSTIDPDY | YYMWTRDSAL | VFKNLVDRFT | ETYDAGLQRR | IEQYITAQVT |
| LQGLSNPSGS | LTDGSGLGEP | KFELTLKPFT | GNWGRPQRDG | PALRAVALIG | YSKWLINNNY |
| QSTVSNVIWP | IVRNDLNYVA | QYWNQTGFDL | WEEVNGSSFF | TMANQHRALV | EGATLAATLG |
| QSGSTYSSVA | PQILCFLQRF | WVSSGGYVDS | NINTNEGRTG | KDVNSVLTSI | HTFDPNLGCD |
| AATFQPCSDK | ALSNLKVVVD | SFRSIYGVNK | GIPAGAAVAI | GRYAEDVYFN | GNPWYLATFA |
| AAEQLYDAIY | VWKKTGSITV | TATSLAFFQE | LVPGVAAGTY | ASSSSTFTNI | INAVSTYADG |
| FLSEAAKYVP | ADGSLAEQFD | RNSGTPLSAL | HLTWSYASFL | TATARRAGIV | PPSWANSSAS |
| TIPSTCSGAS | VVGSYSRPTA | TSFPPSQTPK | PGVPSGTPYT | PLPCATPTSV | AVTFHELVST |
| QFGQTVKVAG | NAPALGNWSA | SAAVALDAIN | YADNHPLWIG | TVDLEAGDVV | EYKYINVGQD |
| GSVTWESDPN | HTYTVPAVAC | VTQVVKEDTW | QS | | |

FIG. 15Q

9b) Mature protein sequence for GA124 (SEQ ID NO: 45).

SVDDFISTETPIALNNLLCNVGPDGCRAFGTSAGAVIASPSTIDPDYYYMWTRDSALVFKNLVDRFTETYD
AGLQRRIEQYITAQVTLQGLSNPSGSLTDGSGLGEPKFELTLKPFTGNWGRPQRDGPALRAVALIGYSKWL
INNNYQSTVSNVIWPIVRNDLNYVAQYWNQTGFDLWEEVNGSSFFTMANQHRALVEGATLAATLGQSGSTY
SSVAPQILCFLQRFWVSSGGYVDSNINTNEGRTGKDVNSVLTSIHTFDPNLGCDAATFQPCSDKALSNLKV
VVDSFRSIYGVNKGIPAGAAVAIGRYAEDVYFNGNPWYLATFAAAEQLYDAIYVWKKTGSITVTATSLAFF
QELVPGVAAGTYASSSSTFTNIINAVSTYADGFLSEAAKYVPADGSLAEQFDRNSGTPLSALHLTWSYASF
LTATARRAGIVPPSWANSSASTIPSTCSGASVVGSYSRPTATSFPPSQTPKPGVPSGTPYTPLPCATPTSV
AVTFHELVSTQFGQTVKVAGNAPALGNWSASAAVALDAINYADNHPLWIGTVDLEAGDVVEYKYINVGQDG
SVTWESDPNHTYTVPAVACVTQVVKEDTWQS

FIG. 15R

10a) Putative amino acid sequence of the Trichoderma asperellum (ATCC28020) glucoamylase, (GA127) - 631 AA (SEQ ID NO: 35), wherein the mature protein sequence is represented by amino acid residue positions 34 – 631 (SEQ ID NO: 46).

MHVLSTAVLL GSVAVQKVLG <u>RPGSNGLSGV TKR</u>SVDDFIN TQTPIALNNL LCNVGPDGCR
AFGTSAGAVI ASPSTTDPDY YYMWTRDSAL VFKNIVDRFT QQYDAGLQRR IEQYISAQVT
LQGISNPSGS LSDGSGLGEP KFELTLSQFT GNWGRPQRDG PALRAIALIG YSKWLINNNY
QSTVSNIIWP IVRNDLNYVA QYWNQTGFDL WEEVNGSSFF TVANQHRALV EGATLAATLG
QSGSTYSSVA PQILCFLQRF WVSGGYIDSN INTNEGRTGK DANSLLASIH TFDPSLGCDA
STFQPCSDKA LSNLKVVVDS FRSIYGVNKG IPAGSAVAIG RYPEDVYFNG NPWYLATFAA
AEQLYDSVYV WKKTGSITVT STSLAFFQEL VPGVAAGTYS SSQSTFTSII NAVSTYADGF
LSEAAKYVPA DGSLAEQFDR NTGTPLSAVH LTWSYASFLT AAARRAGVVP PSWASSGANS
VPSSCSGASV VGSYSRPTAT SFPPSQTPKP GVPSGTPFTP IPCATPTSVA VTFHELATTQ
FGQTIKVAGS APELGNWSTS AAIALDAVNY ATNHPLWIGS VSLEAGDVIE YKYINVGQDG
SVTWESDPNH TYTVPAVACV TEVVKEDTWQ S

*FIG. 15S*

10b) Mature protein sequence for GA127 (SEQ ID NO: 46).

SVDDFINTQTPIALNNLLCNVGPDGCRAFGTSAGAVIASPSTTDPDYYYMWTRDSALVFKNIVDRFTQQYD
AGLQRRIEQYISAQVTLQGISNPSGSLSDGSGLGEPKFELTLSQFTGNWGRPQRDGPALRAIALIGYSKWL
INNNYQSTVSNIIWPIVRNDLNYVAQYWNQTGFDLWEEVNGSSFFTVANQHRALVEGATLAATLGQSGSTY
SSVAPQILCFLQRFWVSGGYIDSNINTNEGRTGKDANSLLASIHTFDPSLGCDASTFQPCSDKALSNLKVV
VDSFRSIYGVNKGIPAGSAVAIGRYPEDVYFNGNPWYLATFAAAEQLYDSVYVWKKTGSITVTSTSLAFFQ
ELVPGVAAGTYSSSQSTFTSIINAVSTYADGFLSEAAKYVPADGSLAEQFDRNTGTPLSAVHLTWSYASFL
TAAARRAGVVPPSWASSGANSVPSSCSGASVVGSYSRPTATSFPPSQTPKPGVPSGTPFTPIPCATPTSVA
VTFHELATTQFGQTIKVAGSAPELGNWSTSAAIALDAVNYATNHPLWIGSVSLEAGDVIEYKYINVGQDG
SVTWESDPNHTYTVPAVACVTEVVKEDTWQS

*FIG. 15T*

11a) Putative amino acid sequence of the Trichoderma strictipilis (CBS347.93) glucoamylase, (GA128) - 632 AA (SEQ ID NO: 37), wherein the mature protein sequence is represented by amino acid residue positions 34 – 632 (SEQ ID NO: 47).

MHVLSTAVLL GSVAVQKVLG RPGSSGLSDI TKRSVDDFIS TQTPIALNNL LCNVGPDGCR
AFGTSAGAVI ASPSTTDPDY YYMWTRDSAL VFKNLVDRFT ETYDAGLQRR IEQYITAQVT
LQGLTNPSGS LADGSGLGEP KFELTLSPFT GNWGRPQRDG PALRAIALIG YSKWLINNNY
QSTVSNVIWP IVRNDLSYAA QYWNQTGFDL WEEVSGSSFF TVANQHRALV EGATLAATLG
QSGSTYSSVA PQILCFLQRF WVSSGGYVDS NINTNEGRTG KDVNSILTSI HTFDPNLGCD
AGTFQPCSDK ALSNFKVVVD SFRSIYGVNN GIPAGAAVAI GRYPEDVYFN GNPWYLATFA
AAEQLYDAIY VWKKTGSITV TAISLAFFQE LVPGVTAGTY SSSQSTFTNI INAASTYADG
FVTEAAKYVP TDGSLAEQFD RNNGTPLSAL HLTWSYASFL TASARRAGVV PPSWANSSAS
SISSTCSGAS VVGSYSSPTA TSFPPSQTPK PGVPSGTPYT PLPCATPTSV AVTFHELVST
QFGQTVKAAG SAPALGNWST SAAVGLDAVN YADNHPLWIG TVELEAGDVV EYKYINVGQD
GSVTWESDPN HTYTVPAVAC VTEVVKEDTW QS

FIG. 15U

11b) Mature protein sequence for GA128 (SEQ ID NO: 47).

SVDDFISTQTPIALNNLLCNVGPDGCRAFGTSAGAVIASPSTTDPDYYYMWTRDSALVFKNLVDRFTETYD
AGLQRRIEQYITAQVTLQGLTNPSGSLADGSGLGEPKFELTLSPFTGNWGRPQRDGPALRAIALIGYSKWL
INNNYQSTVSNVIWPIVRNDLSYAAQYWNQTGFDLWEEVSGSSFFTVANQHRALVEGATLAATLGQSGSTY
SSVAPQILCFLQRFWVSSGGYVDSNINTNEGRTGKDVNSILTSIHTFDPNLGCDAGTFQPCSDKALSNFKV
VVDSFRSIYGVNNGIPAGAAVAIGRYPEDVYFNGNPWYLATFAAAEQLYDAIYVWKKTGSITVTAISLAFF
QELVPGVTAGTYSSSQSTFTNIINAASTYADGFVTEAAKYVPTDGSLAEQFDRNNGTPLSALHLTWSYASF
LTASARRAGVVPPSWANSSASSISSTCSGASVVGSYSSPTATSFPPSQTPKPGVPSGTPYTPLPCATPTSV
AVTFHELVSTQFGQTVKAAGSAPALGNWSTSAAVGLDAVNYADNHPLWIGTVELEAGDVVEYKYINVGQDG
SVTWESDPNHTYTVPAVACVTEVVKEDTWQS

FIG. 15V

SDS-PAGE gel used for determining MW of the purified TrGa

Lane 1: GA104   Lane 5: TrGA
Lane 2: GA105   Lane 6: T. reesei host
Lane 3: GA107   Lane 7: MW Marker
Lane 4: GA109

A. Amino acid sequence of Aspergillus niger glucoamylase (SEQ ID NO: 26) including the signal sequence.

MSFRSLLALSGLVCTGLANVISKRATLDSWLSNEATVARTAILNNIGADGAWVSGADSG
IVVASPSTDNPDYFYTWTRDSGLVLKTLVDLFRNGDTSLLSTIENYISAQAIVQGISNP
SGDLSSGAGLGEPKFNVDETAYTGSWGRPQRDGPALRATAMIGFGQWLLDNGYTSTATD
IVWPLVRNDLSYVAQYWNQTGYDLWEEVNGSSFFTIAVQHRALVEGSAFATAVGSSCSW
CDSQAPEILCYLQSFWTGSFILANFDSSRSGKDANTLLGSIHTFDPEAACDDSTFQPCS
PRALANHKEVVDSFRSIYTLNDGLSDSEAVAVGRYPEDTYYNGNPWFLCTLAAAEQLYD
ALYQWDKQGSLEVTDVSLDFFKALYSDAATGTYSSSSSTYSSIVDAVKTFADGFVSIVE
THAASNGSMSEQYDKSDGEQLSARDLTWSYAALLTANNRRNSVVPASWGETSASSVPGT
CAATSAIGTYSSVTVTSWPSIVATGGTTTTATPTGSGSVTSTSKTTATASKTSTSTSST
SCTTPTAVAVTFDLTATTTYGENIYLVGSISQLGDWETSDGIALSADKYTSSDPLWYVT
VTLPAGESFEYKFIRIESDDSVEWESDPNREYTVPQACGTSTATVTDTWR

FIG. 20A

B. Amino acid sequence of Aspergillus kawachi alpha amylase (AkAA)
(SEQ ID NO: 27) including the signal sequence.

MRVSTSSIALAVSLFGKLALGLSAAEWRTQSIYFLLTDRFGRTDNSTTATCNTGDQIYC
GGSWQGIINHLDYIQGMGFTAIWISPITEQLPQDTSDGEAYHGYWQQKIYNVNSNFGTA
DDLKSLSDALHARGMYLMVDVVPNHMGYAGNGNDVDYSVFDPFDSSSYFHPYCLITDWD
NLTMVQDCWEGDTIVSLPDLNTTETAVRTIWYDWVADLVSNYSVDGLRIDSVEEVEPDF
FPGYQEAAGVYCVGEVDNGNPALDCPYQKYLDGVLNYPIYWQLLYAFESSSGSISNLYN
MIKSVASDCSDPTLLGNFIENHDNPRFASYTSDYSQAKNVLSYIFLSDGIPIVYAGEEQ
HYSGGDVPYNREATWLSGYDTSAELYTWIATTNAIRKLAISADSDYITYANDPIYTDSN
TIAMRKGTSGSQIITVLSNKGSSGSSYTLTLSGSGYTSGTKLIEAYTCTSVTVDSNGDI
PVPMASGLPRVLLPASVVDSSSLCGGSGNTTTTTAATSTSKATTSSSSSAAATTSSS
CTATSTTLPITFEELVTTTYGEEVYLSGSISQLGEWDTSDAVKLSADDYTSSNPEWSVT
VSLPVGTTFEYKFIKVDEGGSVTWESDPNREYTVPECGSGSGETVVDTWR

TRICHODERMA REESEI GLUCOAMYLASE AND HOMOLOGS THEREOF

RELATED APPLICATIONS

The present application is a continuation in part application of application Ser. No. 11/136,244 filed May 24, 2005 now U.S. Pat. No. 7,354,752, which claims priority to provisional patent application Ser. No. 60/647,925 filed Jan. 28, 2005, International Patent Application PCT/US04/041276 filed Dec. 9, 2004; International Application PCT/US04/040040, filed Nov. 30, 2004; provisional application Ser. No. 60/605,437, filed Aug. 30, 2004, now abandoned and provisional application Ser. No. 60/575,175, filed May 27, 2004, now abandoned, and claims priority to International Patent Application PCT/US05/0018212 filed May 24, 2005; which claims priority to provisional applications Ser. No. 60/647,925 filed Jan. 28, 2005, Ser. No. 60/605,437 filed Aug. 30, 2004, now abandoned and Ser. No. 60/575,175 filed May 27, 2004, now abandoned and International Application PCT/US04/040040, filed Nov. 30, 2004 the contents of which are fully incorporated herein by reference.

FIELD OF THE INVENTION

The present invention relates to new glucoamylases useful for the production of glucose and other end products from starch. The glucoamylases are suitable for use in various processes and are particularly suitable for use under conditions of conventional high temperature starch processing and under conditions of non-cook or low temperature starch processing.

BACKGROUND OF THE INVENTION

Glucoamylase enzymes ($\alpha$-1,4-glucan glucohydrolases, E.C.3.2.1.3.) are starch hydrolyzing exo-acting carbohydrases. Glucoamylases catalyze the removal of successive glucose units from the non-reducing ends of starch or related oligo and polysaccharide molecules and can hydrolyze both linear and branched glucosidic linkages of starch (amylose and amylopectin).

Glucoamylases are produced by numerous strains of bacteria, fungi, yeast and plants. Particularly interesting glucoamylases are fungal enzymes that are extracellularly produced, for example from strains of *Aspergillus* (Boel et al., (1984) *EMBO J.* 3:1097-1102; Hayashida et al (1989) *Agric. Biol. Chem.* 53:923-929; U.S. Pat. Nos. 5,024,941; 4,794,175; and WO 88/09795), *Talaromyces* (U.S. Pat. Nos. 4,247,637; 6,255,084 and 6,620,924), *Rhizopus* (Ashikari et al. (1986) *Agric. Biol. Chem.* 50:957-964; Ashikari et al. (1989) *App. Microbiol. and Biotech.* 32:129-133 and U.S. Pat. No. 4,863,864), *Humicola* (WO05/052148 and U.S. Pat. No. 4,618,579) and *Mucor*(Houghton-Larsen et al., (2003) *Appl. Microbiol. Biotechnol.,* 62: 210-217). Many of the genes, which code for these enzymes have been cloned and expressed in yeast and fungal cells.

Commercially glucoamylases are very important enzymes that have been used in a wide variety of applications requiring the hydrolysis of starch. Glucoamylases are used for the hydrolysis of starch to produce high fructose corn sweeteners, and corn sweeteners comprise over 50% of the US sweetener market. In general, starch hydrolyzing processes involve the use of alpha amylases to hydrolyze the starch to dextrins and glucoamylases to hydrolyze the dextrins to glucose. The glucose is then converted to fructose by other enzymes such as glucose isomerases. Glucose produced by glucoamylases can also be crystallized or used in fermentations to produce other end-products, such as citric acid, ascorbic acid, glutamic acid, 1,3 propanediol and others. Glucoamylases are used in alcohol production, such as beer production and sake production. Glucoamylases also find use in the production of ethanol for fuel and for consumption. Recently, glucoamylases have been used in low-temperature processes for the hydrolysis of granular (non-cooked) starch. Glucoamylases are also used in the preparation of animal feeds as feed additives or as liquid feed components for livestock animals.

Although glucoamylases have been used successfully for many years, a need still exists for new useful glucoamylases. The present invention is based upon the finding of novel glucoamylases suitable for use in various applications and particularly starch conversion processes.

SUMMARY OF THE INVENTION

The invention is directed to an isolated DNA sequence encoding a glucoamylase having at least 80% identity to SEQ ID NO: 4.

In another embodiment, the invention is directed to an enzyme having glucoamylase activity comprising the amino acid sequence of SEQ ID NO: 4 or substantially homologous sequences thereto and allelic variants and biologically functional fragments thereof.

In another embodiment, the invention is related to an isolated DNA sequence encoding a *Trichoderma reesei* glucoamylase including the native gene sequence and biologically functional fragments thereof.

In another embodiment, the invention is direct to vectors comprising a DNA sequence encoding the glucoamylases encompassed by the invention.

In another embodiment, the invention is directed to stable transformed fungal host cells, particularly *Trichoderma* and *Aspergillus* host cells and methods for the expression of the glucoamylase therefrom.

In another embodiment, the invention is directed to a culture medium including a glucoamylase encompassed by the invention and enzyme preparations obtained from the growth or culture of transformed hosts and the use of the enzyme preparations.

In another embodiment, the invention is directed to starch conversion processes using the enzyme preparations of the invention. In some embodiments, the glucoamylase will be used in a process of converting starch or partially hydrolyzed starch into a syrup containing dextrose. In other embodiments, the glucoamylase will be used in a process for producing specialty syrups. In further embodiments, the glucoamylase will be used in a fermentation to produce end products, such as alcohols and particularly ethanol.

BRIEF DESCRIPTION OF THE DRAWINGS

FIG. 1A-B shows the genomic DNA sequence (SEQ ID NO: 1) coding for the *Trichoderma reesei* glucoamylase of FIG. 3.

FIG. 2A-B shows the intronless DNA sequence (SEQ ID NO: 2) coding for the *Trichoderma reesei* glucoamylase of FIG. 3.

FIG. 3A shows the deduced amino acid sequence (SEQ ID NO: 3) of the *Trichoderma reesei* glucoamylase having 632 amino acids, wherein the signal sequence (SEQ ID NO: 38) is in bold and is represented by residue positions 1-20;

Figure 16:
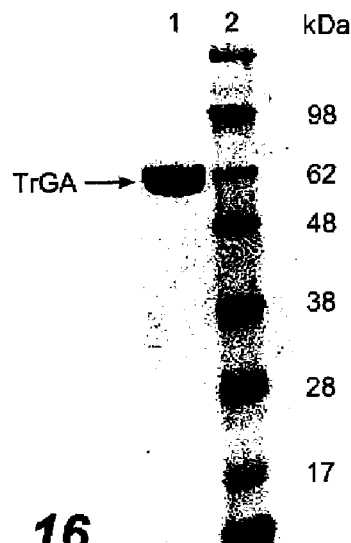

the prosequence (SEQ ID NO: 39) is in bold and underlined and represented by residue positions 21-33;

the catalytic domain (SEQ ID NO: 40) is represented by residue positions 34-486;

the linker region (SEQ ID NO: 41) is in italics and represented by residue positions 487-523; and In other embodiments, the starch binding domain is a fragment of the starch binding domain of SEQ ID NO: 4. Preferably a fragment will encompass at least 90, at least 80 or at least 70 amino acid residues of the starch binding domain of SEQ ID NO: 4.

the starch binding domain (SEQ ID NO: 42) is in italics and underlined and represented by residue positions 524-632.

The N-terminal amino acid residue of the mature protein represented by residue position 34 is serine.

FIG. 3B shows the deduced mature protein sequence (SEQ ID NO: 4) of the *Trichoderma reesei* glucoamylase of FIG. 3A. The mature protein sequence includes the catalytic domain, which is underlined (SEQ ID NO: 40), the linker region (SEQ ID NO: 41) and starch binding domain (SEQ ID NO: 42).

FIG. 4 shows the genomic DNA sequence having 2154 bp (SEQ ID NO: 5) coding for the *Hypocrea citrina* var. *americana* glucoamylase (GA102) (SEQ ID NO: 6).

FIG. 5 shows the genomic DNA sequence having 2152 bp (SEQ ID NO: 7) coding for the *Hypocrea vinosa* glucoamylase (GA104) (SEQ ID NO: 8).

FIG. 6 shows the genomic DNA sequence having 2158 bp (SEQ ID NO: 9) coding for a *Trichoderma* sp. glucoamylase (GA105) (SEQ ID NO: 10).

FIG. 7 shows the genomic DNA sequence having 2144 bp (SEQ ID NO: 11) coding for a *Hypocrea gelatinosa* glucoamylase (GA107) (SEQ ID NO: 12).

FIG. 8 shows the genomic DNA sequence having 2127 bp (SEQ ID NO: 13) coding for a *Hypocrea orientalis* glucoamylase (GA108) (SEQ ID NO: 14). 1291 FIG. 9 shows the genomic DNA sequence having 2139 bp (SEQ ID NO: 15) coding for a *Trichoderma konilangbra* glucoamylase (GA109) (SEQ ID NO: 16).

FIG. 10 shows the genomic DNA sequence having 2088 bp (SEQ ID NO: 28) coding for *Trichoderma* sp. glucoamylase (GA113) (SEQ ID NO: 29).

FIG. 11 shows the genomic DNA sequence having 2141 bp (SEQ ID NO: 30) coding for a *Trichoderma harzianum* glucoamylase (GA103) (SEQ ID NO: 31).

FIG. 12 shows the genomic DNA sequence having 2131 bp (SEQ ID NO: 32) coding for a *Trichoderma longibrachiatum* glucoamylase (GA124) (SEQ ID NO: 33).

FIG. 13 shows the genomic DNA sequence having 2151bp (SEQ ID NO: 34) coding for *Trichoderma asperellum* glucoamylase (GA127) (SEQ ID NO: 35).

FIG. 14 shows the genomic DNA sequence having 2142 bp (SEQ ID NO: 36) coding for *Trichoderma strictipilis* glucoamylase (GA128) (SEQ ID NO: 37).

FIG. 15A-I shows the putative amino acid sequences for glucoamylases encoded by the DNA sequences of SEQ ID NOs: 5, 7, 9, 11, 13, 15, 28, 30, 32, 34 and 36, which correspond to the amino acid sequences of SEQ ID NOs: 6, 8, 10, 12, 14, 16, 29, 31, 33, 35 and 37 respectively, wherein the leader peptide is in bold and the prosequence is underlined and in bold for each protein. The mature protein sequence which excludes the leader and prosequence for each protein is also represented as SEQ ID NO: 17 for (1) GA102; SEQ ID NO: 18 for (2) GA104; SEQ ID NO: 19 for (3) GA105; SEQ ID NO: 20 for (4) GA107; SEQ ID NO: 21 for (5) GA108; SEQ ID NO: 22 for (6) GA109; SEQ ID NO: 43 for (7) GA113; SEQ ID NO: 44 for (8) GA103; SEQ ID NO: 45 for (9) GA124; SEQ ID NO: 46 for (10) GA127 and SEQ ID NO: 47 for (11) GA128.

FIG. 16 illustrates the SDS-PAGE gel used for determining MW of the purified TrGA, wherein lane 1 exhibits the TrGA and lane 2 exhibits the molecular weight marker SeeBlue Plus 2 (Invitrogen).

Figure 17A:
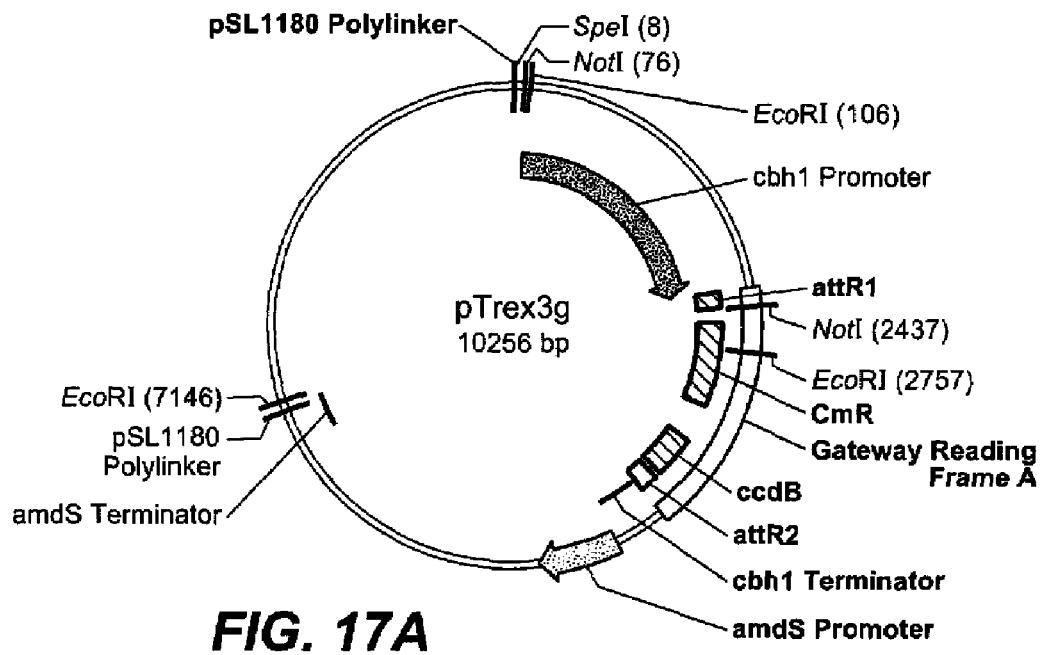

FIG. 17A is a plasmid map of *T. reesei* expression vector, pTrex3g.

Figure 17B:
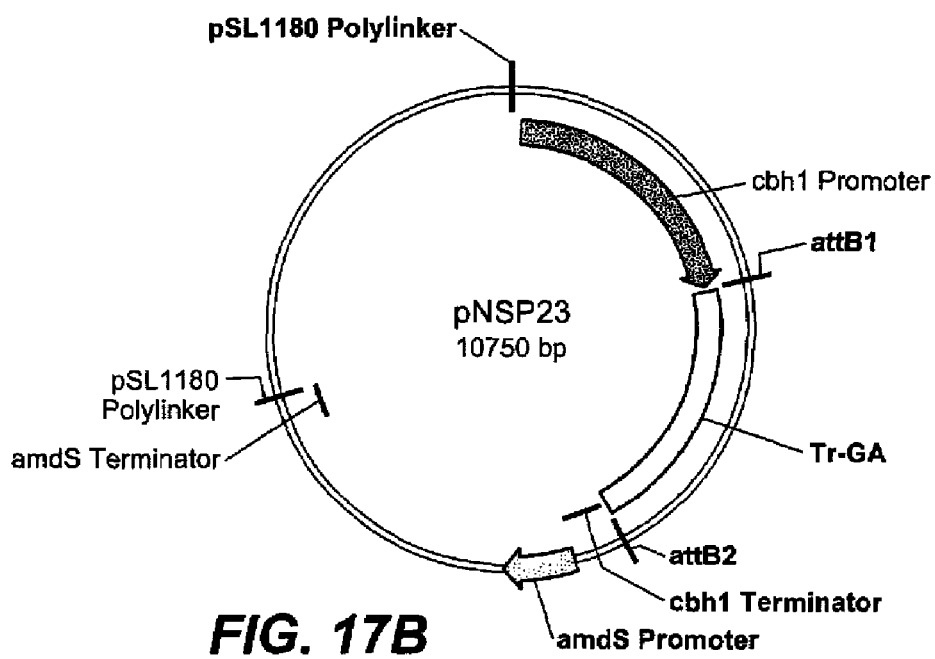

FIG. 17B is a plasmid map that includes the *T. reesei* expression vector pNSP23, wherein the TrGA gene is cloned into pTrex3g.

Figure 18A:
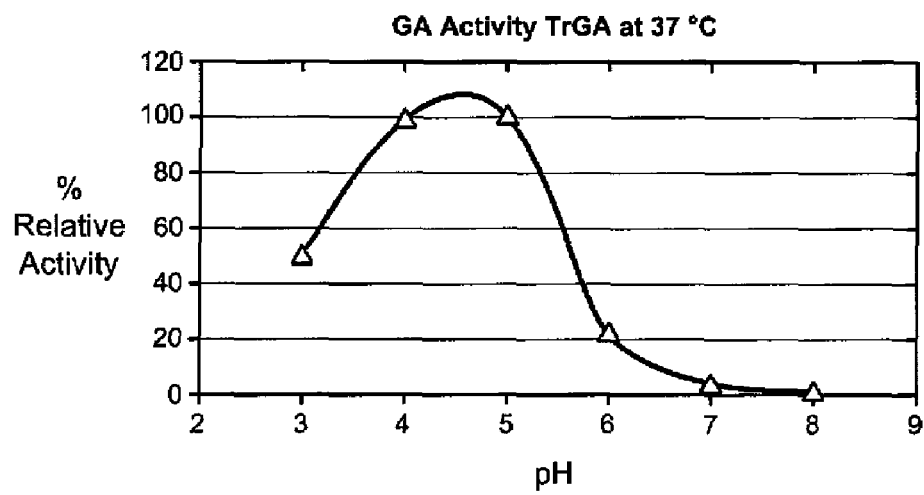
Figure 18B:
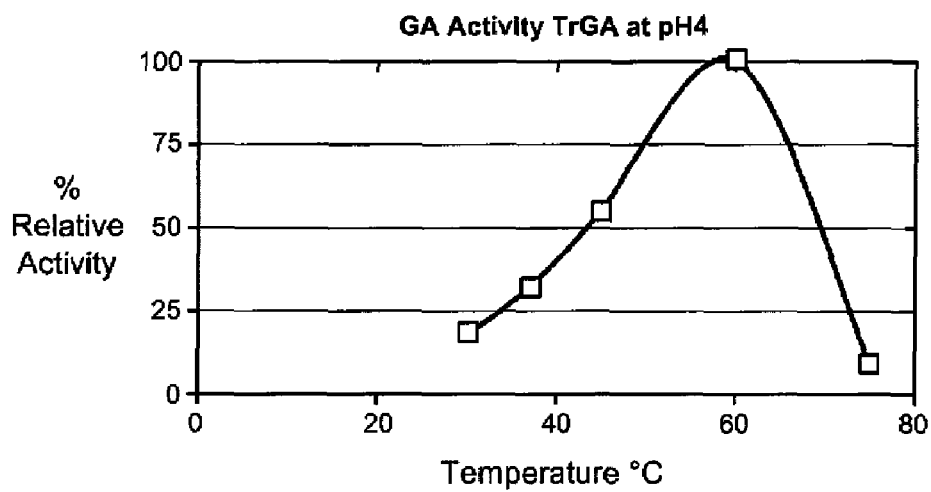

FIG. 18 shows (A) the % relative GA activity of the TrGA at 37° C. from pH 3-8 and (B) the % relative GA activity of the TrGA at pH 4.0 from 25° C. to 78° C. and reference is made to example 4.

Figure 19:
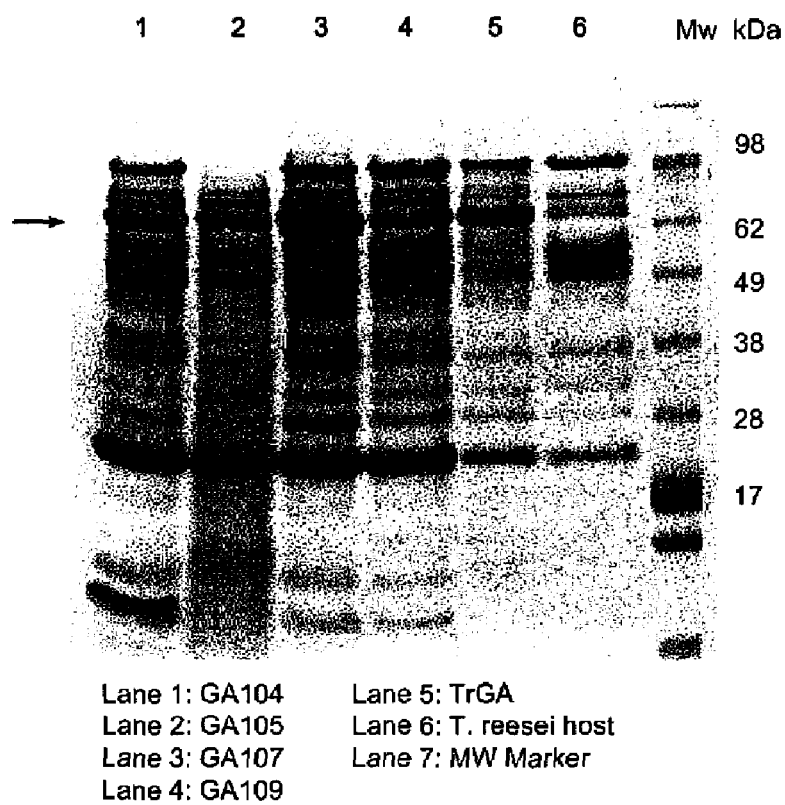

FIG. 19 illustrates the SDS-PAGE gel used for determining secretion of substantially homologous glucoamylases in the Trichoderma host strain (1A52), wherein the band at about 62 kDa represents glucoamylase and lane 1 represents GA104, lane 2 represents GA105; lane 3 represents GC107; lane 4 represents GA109; lane 5 represents TrGA; lane 6 represents a Trichoderma reesei control host strain (1A52); and lane 7 represents a standard molecular weight marker.

FIG. 20(A) illustrates the amino acid sequence (SEQ ID NO: 26) for an *Aspergillus niger* glucoamylase which includes the leader sequence. The N-terminal amino acid residue of the mature protein is represented by residue position 25, A (alanine); the linker region is underlined and the starch binding domain is in italics. (B) illustrates the amino acid sequence for an *Aspergillus kawachi* alpha amylase (SEQ ID NO: 27) which includes the leader sequence, wherein the leader sequence is in bold and underlined and is represented by amino acid residues 1-21; the linker region is underlined and the starch binding domain is in italics. The mature protein includes the catalytic domain, the linker and the starch binding domain.

DETAILED DESCRIPTION OF THE INVENTION

In some aspects, the present invention relies on routine techniques and methods used in the field of genetic engineering and molecular biology. The following resources include descriptions of general methodology useful in accordance with the invention: Sambrook et al. Eds., MOLECULE CLONING: A LABORATORY MANUAL (3$^{rd}$ Ed. 2000); Kriegler M. Ed., GENE TRANSFER AND EXPRESSION: A LABORATORY MANUAL (1990); and Ausubel et al. Eds., SHORT PROTOCOLS IN MOLECULAR BIOLOGY (5$^{th}$ Ed. 2002). Although any methods and materials similar or equivalent to those described herein can be used in the practice or testing of the invention, the preferred methods and materials are described below.

Unless defined otherwise herein all technical and scientific terms used herein have the same meaning as commonly understood by one of ordinary skill in the art to which this invention belongs. Singleton et al., et al., DICTIONARY OF MICROBIOLOGY AND MOLECULAR BIOLOGY 2$^{nd}$ Ed, John Wiley and Sons, NY (1994) and Hale and Margham, THE HARPER COLLINS DICTIONARY OF BIOLOGY (1991) Addison Wesley Pub. Co. provides one of skill with dictionaries of many of the terms used in describing this invention.

The invention will now be described in detail by way of reference only using the following definitions and examples. All patents and publications, including all sequences disclosed within such patents and publications referred to herein are expressly incorporated by reference.

The singular forms "a", "an" and "the" include the plural references unless the content clearly dictates otherwise. Thus for example, reference to a composition containing "a compound" includes a mixture of two or more compounds. It should be noted that the term "or" is generally employed in the sense including "and/or" unless the content clearly dictates otherwise.

Numeric ranges are inclusive of the numbers of the ranges.

Unless otherwise indicated, nucleic acids are written left to right 5' to 3' orientation; amino acids sequences are written left to right in amino carboxy orientation, respectively.

The headings provided herein are not limitations of the various aspects or embodiments of the invention, which can be had by reference to the specification as a whole.

Definitions

The term "glucoamylase" refers to the amyloglucosidase class of enzymes (E.C. 3.2.1.3, glucoamylase, 1,4-alpha-D-glucan glucohydrolase). These enzymes release glucosyl residues from the non-reducing ends of amylose and amylopectin molecules.

The phrase "having granular starch hydrolyzing activity" means an enzyme that is capable of hydrolyzing starch in granular form.

The phrase "Trichoderma/Hypocrea family cluster" means a member of the Family Hypocreaceae including several anamorphs as Trichoderma and Gliocladium of the Order Hypocreales, Phylum Ascomycota and reference is made to Chapter 12, Alexopoulos, C. J., et al., in INTRODUCTORY MYCOLOGY 4$^{th}$ Edition, John Wiley & Sons, NY 1996.

The terms "nucleic acid sequence" and "polynucleotide" maybe used interchangeably herein. The term encompasses genomic DNA, intronless DNA, synthetic origins or combinations thereof.

The term "intron" means an intervening DNA sequence that is transcribed but is removed from within the transcript by splicing together the coding sequences of the mature protein.

The term "isolated nucleic acid sequence" means a nucleic acid sequence, which is essentially free of other nucleic acid sequences.

The term "biologically functional fragments of a sequence" (e.g. biologically functional fragments of SEQ ID NO: 4) means a polypeptide having glucoamylase activity and one or more amino acid residues deleted from the amino and/or carboxyl terminus of the amino acid sequence.

The term "vector" means a polynucleotide sequence designed to introduce nucleic acids into one or more cell types.

The term "expression vector" means a DNA construct comprising a nucleic acid sequence, which is operably linked to a suitable control sequence capable of effecting expression of the nucleic acid sequence in a suitable host. Suitable control sequences include promoters to effect transcription, operator sequences, sequences encoding suitable ribosome binding sites on the mRNA, enhancers and/or termination sequences.

The term "promoter" means a regulatory sequence involved in binding RNA polymerase to initiate transcription of a gene.

The term "operably linked" refers to juxtaposition wherein the elopements are in an arrangement allowing them to be functionally related. For example, a promoter is operably linked to a coding sequence if it controls the transcription of the sequence.

The term "an isolated polypeptide" means a polypeptide that is essentially free of other non-glucoamylase polypeptides. An isolated polypeptide may be at least 20% pure, at least 40% pure, at least 60% pure, at least 70% pure, at least 80% pure, at least 90% pure, at least 95% pure as determined by SDS-PAGE.

The term "signal sequence" means a sequence of amino acids bound to the N-terminal portion of a protein, which facilities the secretion of the mature form of a protein outside the cell. The definition of a signal sequence is a functional one. The mature form of the extracellular protein lacks the signal sequence, which is cleaved off during the secretion process. The terms "signal sequence", signal peptide" and "leader peptide" may be used interchangeability herein. In general the signal sequence refers to the nucleotide sequence and the term leader peptide refers to the amino acid sequence.

The terms "protein" and "polypeptide" are used interchangeably herein. The conventional one-letter or three-letter code for amino acids residues is used herein.

The term "catalytic domain" refers to a structural region of a polypetide, which contains the active site for substrate hydrolysis.

The term "linker" refers to a short amino acid sequence generally having between 3 and 40 amino acids residues that covalently bind an amino acid sequence comprising a starch binding domain with an amino acid sequence comprising a catalytic domain.

The term "starch binding domain" refers to an amino acid sequence that binds preferentially to a starch substrate.

The term "allelic variants" means any of two or more alterative forms of a gene occupying the same chromosomal locus. Allelic variation arises naturally through mutation and may result in polymorphism between populations. An allelic variant of a polypeptide is a polypeptide encoded by an allelic variant of a gene.

The term "host cell" or "host strain" means a suitable host for an expression vector or DNA construct comprising a polypeptide encoding a glucoamylase encompassed by the invention. Suitable host cells are used advantageously in the recombinant production of the glucoamylases encompassed by the invention.

As used herein the term "derived from" used in connection with a polynucleotide or polypeptide means the polypeptide or polynucleotide is native to the microorganism.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in a host cell.

The term "expression" means the process by which a polypeptide is produced based on the nucleic acid sequence of a gene.

The term "over expression" means the process of expressing a polypeptide is a host cell wherein a polynucleotide has been introduced the host cell.

The term "introduced" in the context of inserting a nucleic acid sequence into a cell means transfection, transformation or transduction and includes reference to the incorporation of the nucleic acid sequence into a host cell.

The term "granular starch" refers to raw uncooked starch (e.g. granular starch that has not been subject to gelatinization).

The term "starch" refers to any material comprised of the complex polysaccharide carbohydrates of plant, comprised of amylose and amylopectin with the formula $(C_6H_{10}O_5)_x$, wherein X can be any number.

The term "gelatinization" means the solubilization of a starch molecule by cooking to form a viscous suspension. The phrase "below the temperature of gelatinization" refers to a temperature less than the temperature which starts gelatinization.

The term "culturing" refers to growing a population of microbial cells under suitable conditions in a liquid or solid medium. In one embodiment, culturing refers to fermentative bioconversion of a starch substrate to an end-product (typically in a vessel or reactor). Fermentation is the enzymatic and anaerobic breakdown of organic substances by microorganisms to produce simpler organic compounds. While fermentation occurs under anaerobic conditions it is not intended that the term be solely limited to strict anaerobic conditions as fermentation also occurs in the presence of oxygen.

The term "end-product" refers to any carbon source derived molecule product which is enzymatically converted from a starch substrate.

The term "enzymatic conversion" refers to the modification of a substrate by enzyme action.

The term "specific activity" means an enzyme unit defined as the number of moles of substrate converted to product by an enzyme preparation per unit time under specific conditions. Specific activity is expressed as units (U)/mg or protein.

The term "monosaccharide" means a monomeric unit of a polymer such as starch wherein the degree of polymerization (DP) is 1 (e.g., glucose, mannose, fructose and galactose).

The term "disaccharide" means a compound that comprises two covalently linked monosaccharide units (DP2). The term encompasses, but is not limited to such compounds as sucrose, lactose and maltose.

The term "a DP>3" means polymers with a degree of polymerization greater than 3.

The term "oligosaccharide" means a compound having 2-10 monosaccharide units joined in glycosidic linkages.

The term "polysaccharide" means a compound having multiple monosaccharide units joined in a linear or branched chain. In some embodiments the term refers to long chains with hundreds or thousands of monosaccharide units. Typical examples of polysaccharides are starch, cellulose and glycogen.

As used herein the term "dry solids content (DS or ds)" refers to the total solids of a slurry in % on a dry weight basis.

The term "milling" refers to the breakdown of cereal grains to smaller particles. In some embodiments the term is used interchangeably with grinding.

The term "dry milling" refers to the milling of dry whole grain, wherein fractions of the grain such as the germ and bran have not been purposely removed.

As used herein the terms "distillers dried grain (DDG)" and "distillers dried grain with solubles (DDGS)" refer to useful co-products of grain fermentation processes.

The term "DE" or "dextrose equivalent" is an industry standard for measuring the concentration of total reducing sugars, calculated as D-glucose on a dry weight basis. Unhydrolyzed granular starch has a DE that is essentially 0 and D-glucose has a DE of 100.

The term "sugar syrup" refers to an aqueous composition containing soluble carbohydrates. In one embodiment, the sugar syrup is a syrup containing glucose.

*Trichoderma reesei* Glucoamylase Amino Acid Sequences

A glucoamylase derived from *Trichoderma reesei* QM6a (ATCC, Accession No. 13631) has been cloned as further described in detail in Example 1. According to the invention the full length glucoamylase derived from *Trichoderma reesei* is illustrated in FIG. 3 and has an amino acid sequence of SEQ ID NO: 3. The mature protein sequence of the *Trichoderma reesei* glucoamylase, (SEQ ID NO: 4) is represented by amino acid residues 34-632 of FIG. 3.

This invention relates to an isolated enzyme having glucoamylase activity comprising the sequence shown in SEQ ID NO: 4 or an enzyme with glucoamylase activity being substantially homologous thereto.

In some embodiments, the invention is related to a glucoamylase comprising the sequence shown in SEQ ID NO: 3 or an enzyme with glucoamylase activity being substantially homologous thereto. The glucoamylase of SEQ ID NO: 3 includes the signal sequence of the glucoamylase obtained from *Trichoderma reesei*.

In some embodiments the invention is related to a polypeptide having glucoamylase activity comprising the catalytic domain of the glucoamylase of SEQ ID NO: 4, which is also represented by SEQ ID NO: 40.

In other embodiments, the invention is related to a starch binding domain having at least 90%, at least 95%, at least 97%, and at least 98% sequence identity to the starch binding domain of the glucoamylase illustrated in SEQ ID NO: 4. In some embodiments, the starch binding domain encompasses the sequence of residue position 524 to residue position 632 of SEQ ID NO: 4 and is represented by SEQ ID NO: 42.

In other embodiments, the starch binding domain is a fragment of the starch binding domain of SEQ ID NO: 4. Preferably a fragment will encompass at least 90, at least 80 or at least 70 amino acid residues of the starch binding domain of SEQ ID NO: 4.

Homology of the Protein Sequence

The homology between two glucoamylases may be determined by the degree of identity between the amino acid sequences of two protein sequences. A polypeptide or polynucleotide having a certain percent of identity with another sequence (i.e. 80%, 90%, and 95%) means that when aligned, that percent of bases or amino acid residues are the same in comparing the two sequences. This alignment and percent homology or identity can be determined by using any suitable software program known in the art. For example suitable programs are described in CURRENT PROTOCOLS IN MOLECULAR BIOLOGY (Ausubel et al., eds 1995, Chapter 19). Preferred programs include GCG Pileup program (Wisconsin Package, Version 8.1 and 10.0), FASTA, BLAST and TFASTA. Another preferred alignment program is ALIGN or ALIGN Plus (Dayhoff (1978) in ATLAS OF PROTEIN SEQUENCE AND STRUCTURE 5: Suppl. 3 (National Biomedical Research Foundation)) Further BLASTP, BLASTN and BLASTX algorithms can be used (Altschul et al., (1990) *J. Mol. Biol.* 215:403-410). Other useful methods include ClustralW (Thompson et al., (1997) *Nucleic Acid Research* 25:4876-4882) using software provide by DNASTAR (Madison Wis.). Also reference is made to Needleman et al., (1970) *J. Mol. Biol.* 48:443, Smith et al., (1981) *Adv. Appl. Math.* 2: 482, Smith et al., (1997) *Meth. Mol. Biol.* 70:173-187 and Pearson et al., (1988) *Proc. Natl. Acad. Sci.* 85:24444.

According to the invention a "substantially homologous" amino acid sequence exhibits glucoamylase activity and at least 80% identity, at least 83%, at least 85%, at least 87%, at least 90%, at least 93%, at least 95%, at least 97%, at least 98% and at least 99% identity with the sequence illustrated in SEQ ID NO: 4 or the sequence illustrated in SEQ ID NO: 3. Particularly preferred substantially homologous glucoamylase sequences are the mature protein sequences as shown in FIG. 15 and which correspond to SEQ ID NOs: 17, 18, 19, 20, 21, 22, 43, 44, 45, 46 and 47. Additionally, preferred substantially homologous glucoamylase sequences are the sequences shown in FIG. 15, which correspond to SEQ ID NOs: 6, 8, 10, 12, 14, 16, 29, 31, 33, 35 and 37 and include a leader sequence. Further substantially homologous polypeptides include allelic variations and natural mutants having glucoamylase activity.

The glucoamylases of the present invention including substantially homologous polypeptides and biologically functional fragments, have at least 20%, at least 40%, at least 50%, at least 60%, at least 70%, at least 80%, at least 90%, at least 95% and at least 100% of the glucoamylase activity of the mature protein derived from *Trichoderma reesei* having the sequence illustrated in FIG. 3 (SEQ ID NO: 4). In some preferred embodiments of the invention, the specific activity of the glucoamylases tested under essentially the same conditions will be at least 90%, at least 100%, at least 125%, at least 150%, at least 175% and also at least 200% of the specific activity of the mature protein derived from *Trichoderma reesei* having the sequence illustrated in FIG. 3 (SEQ ID NO: 4). In some embodiments, the specific activity may be measured on a soluble starch substrate and in other embodiments the specific activity may be measured on a granular starch substrate.

In some embodiments, an amino acid sequence having at least 80% sequence identity to the sequence of SEQ ID NO: 3 or SEQ ID NO: 4 will include conservative amino acid substitutions using L-amino acids, wherein one amino acid is replaced by another biologically similar amino acid. Conservative amino acid substitutions are those that preserve the general charge, hydrophobicity/hydrophilicity, and/or steric bulk of the amino acid being substituted. Non-limiting examples of conservative substitutions include those between the following groups: Gly/Ala, Val/Ile/Leu, Lys/Arg, Asn/Gln, Glu/Asp, Ser/Cys/Thr and Phe/Trp/Tyr. Other conservative substitutions can be taken from the table below.

TABLE 1

Conservative Amino Acid Replacements

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

In other embodiments, the amino acid substitutions will not be conservative substitutions.

In some embodiments, it is contemplated that a glucoamylase of the invention will be derived from a filamentous fungal strain and particularly substantially homologous sequences will be obtained from strains of the genus *Aspergillus* spp., *Rhizopus* spp., *Humicola* spp., *Fusarium* spp., *Mucor* spp., *Trichoderma* spp., and the like. In a preferred embodiment, substantially homologous sequences having glucoamylase activity will be derived from strains of the Trichoderma/Hypocrea family cluster. Some of these species include *T. stromaticum, H. citrina* var. *americana, H. citrina, H. lactea, H. hunua, T. fertile, T. tomentosum, H. vinosa, T. harzianum, T. inhamatum, T. oblongisporum, T.* cf. *aureoviride, T.* cf. *harzianum, T. fasciculatum, H. tawa, T. crassum, T. flavovirens, T. virens, T. longipilis, T. spirale, T. strictipilis, H. pilulifera, T. polysporum, T. croceum, T. minutisporum, T. hamatum, T. asperellum, T. atroviride, T koningii, T. viride, H. gelatinosa, T. strigosum, T. pubescens, H. novazelandiae, T. satumisporum, T. longibrachiatum, H. orientalis, T. citrinoviride, T. reesei, T. ghanense, T. pseudokonimgii, H. andinensis* and *H. aureoviride*. Particularly preferred strains of the genus *Trichoderma* and allied *Hypocrea* spp. include *H. citrina* var. *americana, H. citrina, H. lactea, H. vinosa, T. harzianum, T. atroviride, T. koningii, T. viride, H. gelatinosa, T. satumisporum, T. longibrachiatum, H. orientalis, T. citrinoviride, T. reesei,* and *T. konilangbra*.

Some strains of the species described above are accessible to the public from culture collections such as American Type Culture Collection (ATCC) P. O. Box 1549, Manassas, Va. 20108; Deutsche Sammlung von Mikroorganismen und Zellkulturen GmbH (DSM); Agricultural Research Service Plant Culture Collection, Northern Regional Research Center (NRRL); the Centraalbureau voor Schimmelcultures (CBS), P. O. Box 85167, 3508 AD Utrecht, The Netherlands; Plant Research Institute, Department of Agriculture, Mycology, Ottawa, (DAOM) Canada and International Mycological Institute (IMI), Genetic Resources Collection, Egham, United Kingdom.

Biologically Functional Glucoamylase Fragments

In some embodiments, the invention is related to biologically functional fragments of the glucoamylase disclosed in SEQ ID NO: 3, SEQ ID NO: 4 or substantially homologous sequences thereto. In some embodiments, the biologically functional fragment will include the catalytic domain of a glucoamylase encompassed by the invention. In other embodiments, the biologically functional fragments will include at least 400 amino acid residues, at least 425 amino acid residues, at least 450 amino acid residues, and also at least 460 amino acid residues.

In some preferred embodiments, the fragment will encompass at least a part of the amino acid sequence represented by residue positions 1 to 453 of SEQ ID NO: 4, and in other embodiments, the fragment will encompass positions 1 to 453 of SEQ ID NO: 4. In further preferred embodiments, the fragment will encompass the amino acid sequence represented by residue positions 1 to 453 of SEQ ID NO: 17; residue positions 1 to 452 of SEQ ID NO: 18; residue positions 1 to 454 of SEQ ID NO: 19; residue positions 1 to 452 of SEQ ID NO: 20; residue positions 1 to 453 of SEQ ID NO: 21; residue positions 1 to 453 of SEQ ID NO: 22; residue positions 1 to 452 of SEQ ID NO: 43; residue positions 1 to 452 of SEQ ID NO: 44; residue positions 1 to 453 of SEQ ID NO: 45; residue positions 1 to 452 of SEQ ID NO: 46; or residue positions 1 to 453 of SEQ ID NO: 47.

Biologically functional glucoamylase fragments encompassed by the invention can be generated by method known in the art.

Glucoamylases having at least 85%, at least 90%, at least 93%, at least 95%, at least 97%, at least 98% and at least 99% sequence identity to the fragment which consists of amino acid residue 1 to 453 of SEQ ID NO: 4 are also contemplated by the invention.

In other embodiments, the biologically functional fragments will include the catalytic domain and the linker sequence of the glucoamylase disclosed in SEQ ID NO: 4.

The biologically functional fragments may also comprise fused polypeptides or cleavable fused polypeptides in which another polypeptide is fused at the N- terminus and/or the C-terminus of the polypeptide. Techniques for producing fusion polypeptides are known in the art.

Cloned *Trichoderma reesei* and Substantially Homologous DNA Sequences

The invention also relates to a cloned DNA sequence coding for a polypeptide exhibiting glucoamylase activity of the invention, said DNA sequence comprising
  a) the DNA sequence illustrated in SEQ ID NO: 1;
  b) the DNA sequence illustrated in SEQ ID NO: 2;
  c) a DNA sequence encoding a glucoamylase having at least 80%, at least 83%, at least 85%, at least 87%, at least 90%, at least 93%, at least 95%, at least 97%, at least 98% and at least 99% identity with the sequence of SEQ ID NO: 3;
  d) a DNA sequence encoding a glucoamylase having at least 80%, at least 83%, at least 85%, at least 87%, at least 90%, at least 93%, at least 95%, at least 97%, at least 98% and at least 99% identity with the sequence of SEQ ID NO: 4;
  e) a DNA sequence encoding an enzyme having glucoamylase activity, wherein the enzyme has at least 95%, at least 96%, at least 97%, at least 98% and at least 99% sequence identity to any one of the sequences shown in SEQ ID NOs: 17, 18, 19, 20, 21, 22, 43, 44, 45, 46 and 47;
  f) a DNA sequence encoding a biologically functional fragment of a sequence having at least 85%, at least 90%, at least 95%, at least 96%, at least 97% and at least 98% identity to amino acid residue position 1 to 453 of the sequence shown in SEQ ID NO: 4;
  g) a DNA sequence encoding an enzyme having glucoamylase activity comprising an amino acid sequence having at least 90%, at least 95%, at least 97% and at least 98% sequence identity to any one of the following sequences
    a. amino acid residue positions 1 to 453 of SEQ ID NO: 17;
    b. amino acid residue positions 1 to 452 of SEQ ID NO: 18;
    c. amino acid residue positions 1 to 454 of SEQ ID NO: 19;
    d. amino acid residue positions 1 to 452 of SEQ ID NO: 20;
    e. amino acid residue positions 1 to 453 of SEQ ID NO: 21;
    f. amino acid residue positions 1 to 453 of SEQ ID NO: 22;
    g. amino acid residue positions 1 to 452 of SEQ ID NO: 43;
    h. amino acid residue positions 1 to 452 of SEQ ID NO: 44;
    i. amino acid residue positions 1 to 453 of SEQ ID NO: 45;
    j. amino acid residue positions 1 to 452 of SEQ ID NO: 46; and
    k. amino acid residue positions 1 to 453 of SEQ ID NO: 47.
  h) a DNA which is at least 80%, at least 85%, at least 90%, at least 93%, at least 95%, at least 97% and at least 99% identical to the sequence shown in SEQ ID NO: 1 or SEQ ID NO: 2, wherein said DNA sequence codes for an enzyme having glucoamylase activity; or
  i) a DNA sequence, which hybridizes under high stringent conditions to a nucleic acid probe corresponding to the DNA sequence of SEQ ID NO: 2 or a fragment thereof having at least 20, at least 30 at least 40, at least 50 at least 60, at least 70 at least 100, at least 150 consecutive nucleotides.

The invention additionally encompasses a cloned DNA sequence encoding an enzyme having glucoamylase activity and at least 95%, at least 96%, at least 97% at least 98% and at least 99% sequence identity to the amino acid sequences of any one of SEQ ID NOs: 6, 8, 10, 12, 14, 16, 29, 31, 33, 35, and 37.

Because of the degeneracy of the genetic code, more than one codon may be used to code for a particular amino acid. Therefore, different DNA sequences may encode a polypeptide having exactly the same amino acid sequence as the polypeptide of, for example SEQ ID NO: 4. The present invention encompasses polynucleotides, which encode the same polypeptide. DNA sequences, which encode glucoamylases encompassed by the invention may or may not include introns.

Homology of DNA sequences is determined by the degree of identity between two DNA sequences. Homology may be determined using computer programs as described above for determining protein sequence homology.

A nucleic acid is hybridizable to another nucleic acid when a single stranded form of the nucleic acid can anneal to the other nucleic acid under appropriate conditions of temperature and solution ionic strength. Hybridization and washing conditions are well known in the art for hybridization under low, medium, medium/high, high and very high stringency conditions (See., e.g. Sambrook et al., supra, particularly chapters 9 and 11). In general, hybridization involves a nucleotide probe and a homologous DNA sequence that form stable double stranded hybrids by extensive base-pairing of complementary polynucleotides (See, Chapter 8, GeneCloning, An Introduction, T. A. Brown, (1995) Chapman and Hall, London).

The filter with the probe and homologous sequence are washed in 2× sodium chloride /sodium citrate (SSC), 0.5% SDS at about 60° C. (medium stringency); 65° C. (medium/high stringency) 70° C. (high stringency) and about 75° C. (very high stringency).

Vectors

According to one embodiment of the invention, a DNA construct comprising a nucleic acid sequence encoding a glucoamylase encompassed by the invention and operably linked to a promoter sequence is assembled to transfer into a host cell. The DNA construct may be introduced into a host cell using a vector. The vector may be any vector which when introduced into a host cell is integrated into the host cell genome and is replicated. Vectors include cloning vectors, expression vectors, shuttle vectors, plasmids, phage particles, cassettes and the like. In some preferred embodiments, the vector is an expression vector that comprises regulatory sequences operably linked to the glucoamylase coding sequence.

Examples of suitable expression and/or integration vectors are provided in Sambrook et al., (1989) supra, and Ausubel (1987) supra, and van den Hondel et al. (1991) in Bennett and Lasure (Eds.) MORE GENE MANIPULATIONS IN FUNGI, Academic Press pp. 396-428 and U.S. Pat. No. 5,874,276. Reference is also made to the Fungal Genetics Stock Center Catalogue of Strains (FGSC, <www.fgsc.net>) for a list of vectors. Particularly useful vectors include vectors obtained from for examples Invitrogen and Promega. Specific vectors suitable for use in fungal host cells include vectors such as pFB6, pBR322, pUC18, pUC100, pDON™201, pDONR™221, pENTR™, pGEM®3Z and pGEM®4Z.

In some preferred embodiments, the promoter, which shows transcriptional activity in a fungal host cell may be derived from genes encoding proteins either homologous or heterologous to the host cell. The promoter may be a mutant, truncated and hybrid promoter. Preferably, the promoter is useful in a Trichoderma or Aspergillus host. Exemplary promoters include the T. reesei promoters cbh1, cbh2, egl1, egl2, eg5, xln1 and xln2. Other examples of useful promoters include promoters from A. awamori and A. niger glucoamylase genes (glaA) (See, Nunberg et al., (1984) Mol. Cell Biol. 4:2306-2315 and Boel et al., (1984) EMBO J. 3:1581-1585), Aspergillus nidulans acetamidase genes and Rhizomucor miehei lipase genes.

In one embodiment, the promoter is one that is native to the host cell. For example, when T. reesei is the host, the promoter is a native T. reesei promoter.

In another embodiment, the promoter is one that is heterologous to the fungal host cell.

In a preferred embodiment, the promoter is T. reesei cbh1, which is an inducible promoter and has been deposited in GenBank under Accession No. D86235.

An "inducible promoter" is a promoter that is active under environmental or developmental regulation. In some embodiments, the DNA construct includes nucleic acids coding for a signal sequence that is an amino acid sequence linked to the amino terminus of the polypeptide which directs the encoded polypeptide into the cell's secretory pathway. The 5' end of the coding sequence of the nucleic acid sequence may naturally include a signal peptide coding region which is naturally linked in translation reading frame with the segment of the glucoamylase coding sequence which encodes the secreted glucoamylase or the 5' end of the coding sequence of the nucleic acid sequence may include a signal peptide which is foreign to the coding sequence. In some preferred embodiments, the DNA construct includes a signal sequence that is naturally associated with the glucoamylase gene to be expressed. Effective signal sequences may include the signal sequences obtained from glucoamylases of other filamentous fungal cells, such as from Humicola, Aspergillus, and Rhizopus.

In preferred embodiments, the nucleic acid of the DNA construct codes for a signal sequence having at least 95%, at least 96%, at least 97%, at least 98% and at least 99% sequence identity to the signal sequence depicted in FIG. 3.

In additional embodiments, a DNA construct or vector comprising a signal sequence and a promoter sequence to be introduced into a fungal host cell are derived from the same source. For example, in some embodiments, the signal sequence is the cbh1 signal sequence which is operably linked to a cbh1 promoter. In other preferred embodiments the native glucoamylase signal sequence of a Trichoderma/Hypocrea family cluster member will be used.

In some embodiments, the expression vector also includes a termination sequence. Any terminator sequence functional in the host cell may be used in the present invention. In one embodiment, the termination sequence and the promoter sequence are derived from the same source. In another embodiment, the termination sequence is homologous to the host cell. A particularly suitable terminator sequence is cbh1 derived from a Trichoderma strain and particularly T. reesei. Other useful fungal terminators include the terminator from A. niger or A. awamori glucoamylase genes (Nunberg et al. (1984) supra, and Boel et al., (1984) supra), Aspergillus nidulans anthranilate synthase genes, Aspergillus oryzae TAKA amylase genes, or A. nidulans trpC (Punt et al., (1987) Gene 56:117-124).

In some embodiments, an expression vector includes a selectable marker. Examples of preferred selectable markers include ones which confer antimicrobial resistance (e.g., hygromycin and phleomycin). Nutritional selective markers also find use in the present invention including those markers known in the art as amdS, argB and pyr4. Markers useful in vector systems for transformation of Trichoderma are known in the art (See, e.g., Finkelstein, chapter 6 in BIOTECHNOLOGY OF FILAMENTOUS FUNGI, Finkelstein et al. Eds. Butterworth-Heinemann, Boston, Mass. (1992), Chap. 6; and Kinghorn et al. (1992) APPLIED MOLECULAR GENETICS OF FILAMENTOUS FUNGI, Blackie Academic and Professional, Chapman and Hall, London). In a preferred embodiment, the selective marker is the amdS gene, which encodes the enzyme acetamidase, allowing transformed cells to grow on acetamide as a nitrogen source. The use of A. nidulans amdS gene as a selective marker is described in Kelley et al., (1985) EMBO J. 4:475-479 and Penttilä et al., (1987) Gene 61:155-164.

Methods used to ligate the DNA construct comprising a nucleic acid sequence encoding a glucoamylase, a promoter, a terminator and other sequences and to insert them into a suitable vector are well known in the art. Linking is generally accomplished by ligation at convenient restriction sites. If such sites do not exist, synthetic oligonucleotide linkers are used in accordance with conventional practice. (See, Sambrook (1989) supra, and Bennett and Lasure, MORE GENE MANIPULATIONS IN FUNGI, Academic Press, San Diego (1991) pp 70-76.). Additionally, vectors can be constructed using known recombination techniques (e.g., Invitrogen Life Technologies, Gateway Technology).

Host Cells

The present invention also relates to host cells comprising a nucleic acid sequence encoding a glucoamylase of the invention, which are used in the production of the glucoamylases of the invention. Preferred host cells according to the invention are filamentous fungal cells, and the term host cell includes both the cells, progeny of the cells and protoplasts created from the cells of a filamentous fungal strains.

The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic. In the present invention, the filamentous fungal parent cell may be a cell of a species of, but not limited to, Trichoderma, (e.g., Trichoderma reesei, the asexual morph of Hypocrea jecorina, T. longibrachiatum, Trichoderma viride,

*Trichoderma koningii, Trichoderma harzianum*); *Penicillium* sp., *Humicola* sp. (e.g., *H. insolens, H. lanuginosa* and *H. grisea*); *Chrysosporium* sp. (e.g., *C. lucknowense*), *Gliocladium* sp.,*Aspergillus* sp. (e.g.,*A. oryzae, A. niger, A. nidulans,* and *A. awamori*), *Fusarium* sp.,(e.g. *F. graminum* and *F. venenatum*), *Neurospora* sp., *Hypocrea* sp., *Mucor*, and *Emericella* sp. (See also, Innis et al., (1985) Sci. 228:21-26). The term "*Trichoderma*" or "*Trichoderma* sp." refer to any fungal genus previously or currently classified as *Trichoderma*. In some embodiments, the host cell will be a genetically engineered host cell wherein native genes have been inactivated, for example by deletion. Where it is desired to obtain a fungal host cell having one or more inactivated genes known methods may be used (e.g. methods disclosed in U.S. Pat. Nos. 5,246,853, 5,475,101 and WO92/06209). Gene inactivation may be accomplished by complete or partial deletion, by insertional inactivation or by any other means which renders a gene nonfunctional for its intended purpose (such that the gene is prevented from expression of a functional protein). Any gene from a *Trichoderma* sp. or other filamentous fungal host, which has been cloned can be deleted. In some preferred embodiments, when the host cell is a *Trichoderma* cell and particularly a *T. reesei* host cells the cbh1, cbh2, egl1 and egl2 genes will be inactivated and preferably deleted. Particualrly preferred *Trichoderma reesei* host cells having quad-deleted proteins are set forth and described in U.S. Pat. No. 5,847,276 and WO 05/001036.

Transformation of Host Cells

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (See, e.g., Ausubel et al., (1987), supra, chapter 9; and Sambrook (1989) supra, and Campbell et al., (1989) *Curr. Genet.* 16:53-56). The expression of heterologous protein in *Trichoderma* is described in U.S. Pat. Nos. 6,022,725; 6,268,328; Harkki et al. (1991); *Enzyme Microb. Technol.* 13:227-233; Harkki et al., (1989) *Bio Technol.* 7:596-603; EP 244,234; EP 215,594; and Nevalainen et al., "*The Molecular Biology of Trichoderma and its Application to the Expression of Both Homologous and Heterologous Genes*", in MOLECULAR INDUSTRIAL MYCOLOGY, Eds. Leong and Berka, Marcel Dekker Inc., NY (1992) pp. 129-148). Reference is also made to Cao et al., (2000) *Sci.* 9:991-1001 and EP 238 023 for transformation of *Aspergillus* strains and WO96/00787 for transformation of *Fusarium* strains.

Preferably, genetically stable transformants are constructed with vector systems whereby the nucleic acid encoding the glucoamylase is stably integrated into a host strain chromosome. Transformants are then purified by known techniques. In one nonlimiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium (i.e., $NH_4(SO_4)_2$ (5 mg/mL) as a nitrogen source), harvesting spores from this culture medium and determining the percentage of these spores which subsequently germinate and grow on selective medium containing 10 mM acetamide as a sole nitrogen source. Alternatively, other methods known in the art may be used to select transformants.

In one specific embodiment, the preparation of *Trichoderma* sp. for transformation involves the preparation of protoplasts from fungal mycelia (See, Campbell et al., (1989) *Curr. Genet.* 16:53-56). Also agrobacterium tumefaciens-mediated transformation of filamentous fungi is known (See, de Groot et al., (1998) *Nat. Biotechnol.* 16:839-842).

In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium. Uptake of DNA into the host *Trichoderma* sp. strain is dependent upon the calcium ion concentration. Generally, between about 10 mM $CaCl_2$ and 50 mM $CaCl_2$ is used in an uptake solution. Reference is also made to U.S. Pat. Nos. 6,022,725 and 6,268,328 for transformation procedures used with filamentous fungal hosts.

The present invention relates to methods of recombinantly producing the glucoamylase comprising expressing a polynucleotide encoding a glucoamylase of the invention in a filamentous fungal host cell and cultivating the host cell under conditions suitable for production of the glucoamylase and optionally recovering the glucoamylase.

In the expression and production methods of the present invention the fungal cells are cultured under suitable conditions in shake flask cultivation, small scale or large scale fermentations (including continuous, batch and fed batch fermentations) in laboratory or industrial fermentors, with suitable medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth) find use in the present invention. Preferred culture conditions for a given filamentous fungus are known in the art and may be found in the scientific literature and/or from the source of the fungi such as the American Type Culture Collection and Fungal Genetics Stock Center. In cases where a glucoamylase coding sequence is under the control of an inducible promoter, the inducing agent (e.g., a sugar, metal salt or antimicrobial), is added to the medium at a concentration effective to induce glucoamylase expression.

In some embodiments, in order to evaluate the expression of a glucoamylase by a cell line that has been transformed with a polynucleotide encoding a glucoamylase encompassed by the invention, assays are carried out at the protein level, the RNA level and/or by use of functional bioassays particular to glucoamylase activity and/or production. Some of these assays include Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of a glucoamylase may be measured in a sample directly, for example, by assays directly measuring reducing sugars such as glucose in the culture medium and by assays for measuring glucoamylase activity, expression and/or production. In particular glucoamylase activity may be assayed by the 3,5-dinitrosalicylic acid (DNS) method (See, Goto et al., (1994) Biosci. Biotechnol. Biochem. 58:49-54). In additional embodiments, protein expression, is evaluated by immunological methods, such as immunohistochemical staining of cells, tissue sections or immunoassay of tissue culture medium, (e.g., by Western blot or ELISA). Such immunoassays can be used to qualitatively and quantitatively evaluate expression of a glucoamylase. The details of such methods are known to those of skill in the art and many reagents for practicing such methods are commercially available.

The glucoamylases of the present invention may be recovered or purified from culture media by a variety of procedures known in the art including centrifugation, filtration, extraction, precipitation and the like.

Uses and Compositions

The present invention is also directed to compositions comprising glucoamylases of the invention and methods of using the glucoamylases in industrial and commercial applications. Nonlimiting examples, which include the use of glucoamylases encompassed by the invention in industrial and commercial applications are briefly described below.

The glucoamylases may be used in starch hydrolyzing and saccharifying compositions, cleaning and detergent compositions (e.g., laundry detergents, dish washing detergents, and hard surface cleaning compositions), and in animal feed compositions. Further the glucoamylases may be used in baking applications, such as bread and cake production, brewing, healthcare, textile, environmental waste conversion processes, biopulp processing, and biomass conversion applications.

In particular, the glucoamylases may be used for starch conversion processes, and particularly in the production of dextrose for fructose syrups, specialty sugars and in alcohol and other end-product (e.g. organic acid, ascorbic acid, and amino acids) production from fermentation of starch containing substrates (G.M.A van Beynum et al., Eds. (1985) STARCH CONVERSION TECHNOLOGY, Marcel Dekker Inc. NY). Dextrins produced using glucoamylase compositions of the invention may result in glucose yields of at least 80%, at least 85%, at least 90% and at least 95%. Production of alcohol from the fermentation of starch substrates using glucoamylases encompassed by the invention may include the production of fuel alcohol or portable alcohol.

In one preferred embodiment, the glucoamylases of the invention will find use in the hydrolysis of starch from various plant-based substrates, which are used for alcohol production. In some preferred embodiments, the plant-based substrates will include corn, wheat, barley, rye, milo, rice, sugar cane and combinations thereof. In some embodiments, the plant-based substrate will be fractionated plant material, for example a cereal grain such as corn, which is fractionated into components such as fiber, germ, protein and starch (endosperm) (U.S. Pat. Nos. 6,254,914 and 6,899,910). Methods of alcohol fermentations are described in THE ALCOHOL TEXTBOOK, A REFERENCE FOR THE BEVERAGE, FUEL AND INDUSTRIAL ALCOHOL INDUSTRIES, $3^{rd}$ Ed., Eds K. A. Jacques et al., 1999, Nottingham University Press, UK. In certain preferred embodiments, the alcohol will be ethanol. In particular, alcohol fermentation production processes are characterized as wet milling or dry milling processes. In some embodiments, the glucoamylase will be used in a wet milling fermentation process and in other embodiments the glucoamylase will find use in a dry milling process.

Dry grain milling involves a number of basic steps, which generally include: grinding, cooking, liquefaction, saccharification, fermentation and separation of liquid and solids to produce alcohol and other co-products. Plant material and particularly whole cereal grains, such as corn, wheat or rye are ground. In some cases the grain may be first fractionated into component parts. The ground plant material may be milled to obtain a coarse or fine particle. The ground plant material is mixed with liquid in a slurry tank. The slurry is subjected to high temperatures in a jet cooker along with liquefying enzymes (e.g. alpha amylases) to solubles and hydrolyze the starch in the cereal to dextrins. The mixture is cooled down and further treated with saccharifying enzymes, such as glucoamylases encompassed by the instant invention, to produce glucose. The mash containing glucose is then fermented for approximately 24 to 120 hours in the presence of fermentation microorganisms, such as ethanol producing microorganism and particularly yeast (*Saccharomyces* spp). The solids in the mash are separated from the liquid phase and alcohol such as ethanol and useful co-products such as distillers' grains are obtained.

In some embodiments, the saccharification step and fermentation step are combined and the process is referred to as simultaneous saccharification and fermentation or simultaneous saccharification, yeast propagation and fermentation.

In other embodiments, the cooking step or exposure of the starch containing substrate to temperatures above the gelatinization temperate of the starch in the substrate may be eliminated. These fermentation processes in some embodiments include milling of a cereal grain or fractionated grain and combining the ground cereal grain with liquid to form a slurry which is then mixed in a single vessel with a glucoamylase according to the invention and optionally other enzymes such as but not limited to alpha amylases, other glucoamylases and enzymes having granular starch hydrolyzing activity and yeast to produce ethanol and other co-products (U.S. Pat. No. 4,514,496, WO 04/081193 and WO 04/080923).

In some embodiments, the invention pertains to a method of saccharifying a liquid starch solution, which comprises an enzymatic saccharification step using a glucoamylase of the invention.

In some embodiments, an enzyme composition including a glucoamylase encompassed by the invention and obtained in culture media or recovered and purified from the culture medium will be optionally used in combination with any one or combination of the following enzymes—alpha amylases, proteases, pullulanases, isoamylases, cellulases, hemicellulases, xylanases, cyclodextrin glycotransferases, lipases, phytases, laccases, oxidases, esterases, cutinases, xylanases, granular starch hydrolyzing enzyme and other glucoamylases.

In some particularly preferred compositions the glucoamylases of the invention will be combined with alpha amylases, such as fungal alpha amylases (e.g. *Aspergillus* sp.) or bacterial alpha amylases (e.g. *Bacillus* sp. such as *B. stearothermophilus*, *B. amyloliquefaciens* and *B. licheniformis*) and variants thereof. In some embodiments the alpha amylase will be an alpha amylase having at least 90%, 93%, 95%, 96%, 97%, 98% and 99% sequence identity to the mature protein sequence of SEQ ID NO: 27. Commercially available alpha amylases contemplated for use in the compositions of the invention are known and include GZYME G997, SPEZYME FRED, SPEZYME EHTYL (Genencor International Inc.) and TERMAMYL 120-L and SUPRA (Novozymes, Biotech.).

In other particularly preferred embodiments, the glucoamylases of the invention will be combined with other glucoamylases. In some embodiments, the glucoamylases of the invention will be combined with one or more glucoamylases derived from strains of *Aspergillus* or variants thereof, such as *A. oryzae, A. niger* (e.g., the mature protein sequence of FIG. 20(A), *A. kawachi,* and *A. awamori;* glucoamylases derived from strains of *Humicola* or variants thereof, particualrly *H. grisea,* such as the glucoamylase having at least 90%, 93%, 95%, 96%, 97%, 98% and 99% sequence identity to SEQ ID NO: 3 disclosed in WO 05/052148; glucoamylases derived from strains of *Talaromyces* or variants thereof, particularly *T. emersonii;* and glucoamylases derived from strains of *Athelia* and particularly *A. rolfsii.*

Material and Methods

In the disclosure and experimental section which follows, the following abbreviations apply:

TrGA (a *Trichoderma reesei* glucoamylase composition, the mature protein having the amino acid sequence of SEQ ID NO: 4); AkAA (an *Aspergillus kawachi* alpha amylase composition having the mature protein of sequence SEQ ID NO: 27); AnGA (DISTILLASE comprising an *Aspergillus niger* GA (Genencor International Inc.,)); GA (glucoamylase); GAU (glucoamylase unit); MU (alpha amylase unit); wt % (weight percent); ° C. (degrees Centigrade); rpm (revolutions per minute); $H_2O$ (water); $dH_2O$ (deionized water); $dIH_2O$ (deionized water, Milli-Q filtration); aa or AA (amino acid); bp (base pair); kb (kilobase pair); kD or kDa (kilodaltons); g or gm (grams); μg (micrograms); mg (milligrams); μL (microliters); ml and mL (milliliters); mm (millimeters); μm (micrometer); M (molar); mM (millimolar); μM (micromolar); U (units); V (volts); MW (molecular weight); sec (seconds); min(sy (minute/minutes); hr(s) (hour/hours); DO (dissolved oxygen); and EtOH (ethanol).

The following assays and methods are used in the examples provided below:

1) GA Assay—Glucoamylase assay: Glucoamylase activity was measure using a well-known assay which is based on the ability of glucoamylase to catalyze the hydrolysis of p-nitrophenyl-alpha-D-glucopyranoside (pNPG) to glucose and p-nitrophenol. At an alkaline pH, the nitrophenol forms a yellow color that is proportional to glucoamylase activity and is monitored at 400nm and compared against an enzyme standard measured as a GAU (Elder, M. T. and Montgomery R. S., Glucoamylase activity in industrial enzyme preparations using calorimetric enzymatic method, Journal of AOAC International, vol. 78(2), 1995).

One GAU is defined as the amount of enzyme that will produce 1 gm of reducing sugar calculated as glucose per hour from a soluble starch substrate (4% ds) at pH 4.2 and 60° C.

2) Primers and PCR Protocol for Amplification of Genes from *Trichoderma/Hypocrea* Strains:

| Trichoderma/Hypocrea GA - gene | Primer | Gene Specific Sequence | SEQ ID NO: |
|---|---|---|---|
| Trichoderma reesei | NSP231F | ATGCCCGCCTTCGC CATGGACC | 23 |
| | NSP232R | TTACGACTGCCAGG TGTCCTCC | 24 |
| | NSP233F | ATGCACGTCCTGTC GACTGCGG | 25 |

| Component | μl |
|---|---|
| Forward primer (10 μM) | 1 |
| Reverse primer (10 μM) | 1 |
| Template genomic DNA | 5 |
| dNTP (10 mM) | 1 |
| HiFi Buffer | 5 |
| $MgSO_4$ (50 mM) | 2 |
| DNA polymerase- Platinum Taq Polymerase High Fidelity (Invitrogen, cat. No. 11304-029) | 0.5 |
| Milli-Q water, sterile | 34.5 |

With respect to the PCR program, initial denaturation was 2 min, at 94° C. for 1 cycle; denaturation 30 sec, at 94° C., annealing for 30 sec, at 55° C. and extension for 2 min at 68° C. for 30 cycles and a final extension step of 7 min at 68° C.

3) Ethanol and Carbohydrate Determinations

Ethanol and carbohydrate composition of the samples were determined using the HPLC method as described herein:

a) a 1.5 mL Eppendorf centrifuge tube was filled with fermentor beer and cooled on ice for 10 min;
b) the sample tube was centrifuged for 1 min in Eppendorf table top centrifuge;
c) a 0.5 mL sample of the supernatant was transferred to a test tube containing 0.05 mL of Kill solution (1.1N $H_2SO_4$) and allowed to stand for 5 min;
d) 5.0 mL of water is added to the test tube sample and then filtered into a HPLC vial through 0.45 μm Nylon Syringe Filter; and
e) run on HPLC.

HPLC Conditions:

a) Ethanol System: Column: Phenomenex Rezex Organic Acid Column (RHM-Monosaccharide) #00H 0132-KO (Equivalent to Bio-Rad 87H); Column Temperature: 60° C.; Mobile Phase: 0.01 N $H_2SO_4$; Flow Rate: 0.6 mL/min; Detector: RI; and b) Injection Volume: 20 μL.

c) Carbohydrate System: Column: Phenomenex Rezex Carbohydrate (RCM-Monosaccharide) #00H-0130-KO (Equivalent to Bio-Rad 87H); Column Temperature: 70° C.; Mobile Phase: Nanopure DI $H_2O$; Flow Rate: 0.8 mL/min; Detector: RI; Injection Volume: 10 μL (3% DS Material)

The column separates based on the molecular weight of the saccharides, which are designated as DP-1 (monosaccharides); DP-2 (disaccharides); DP-3 (trisaccharides) and DP>3 (oligosaccharide sugars having a degree of polymerization greater than 3).

4) Residual starch iodine test: A sample of the beer (fermentation broth) was centrifuged in 2 ml plastic centrifuge tubes. The supernatant was decanted and the tube containing the pellet was placed in an ice bath. Several drops of 0.025N iodine solution (0.1N iodine from VWR Cat. No. VW3207-1 diluted 4×) was added to the pellet and mixed. A positive (+) starch shows a range of color from blue to purple and the intensity of color is directly proportional to the concentration of starch. A negative result (−) remains yellowish.

5) Determination of total starch content: The enzyme-enzyme starch liquefaction and saccharification process (dual enzyme method) was used to determine the total starch content. In a typical analysis, 2 g of the dry sample was taken in a 100 ml Kohlraucsh flask and 45 ml of MOPS buffer, pH 7.0 was added. The slurry was well stirred for 30 min. SPEZYME FRED (1:50 diluted in water), 1.0 ml was added and heated to boiling for 3-5 min. The flask was placed in an autoclave maintained at 121° C. for 15 min. After autoclaving the flask was placed in a water bath at 95° C and 1 ml of 1:50 dilutes SPEZYME FRED was added and incubated for 45 min. The pH was adjusted to pH 4.2 and the temperature was reduced to 60° C. This was followed by addition of 20 ml acetate buffer, pH 4.2. Saccharification was carried out by adding 1.0 ml of 1:100 diluted OPTIDEX L-400 (Glucoamylase from Genencor International Inc.) and the incubation was continued for 18 hr at 60° C. The enzyme reaction was terminated by heating at 95° C. for 10 min. The total sugar composition was determined by HPLC analysis using glucose as a standard. The soluble starch hydrolysate from water extraction of a sample at room temperature without enzymatic treatment was subtracted from the total sugar.

6) Total protein analysis: The total nitrogen (N) in the sample preparations was determined using the Kjeldhal method (American Assoc. Cereal Chemists (AACC), (1983), Methods 22B60 8th Ed. St Paul, Minn.). Protein content was calculated by 6.25× total N.

EXAMPLES

The following examples are provided in order to demonstrate and further illustrate certain preferred embodiments and aspect of the present invention and are not to be construed as limiting the scope thereof.

Example 1

Isolation and Cloning of the TrGA

Chromosomal DNA of *Trichoderma reesei* QM6a was isolated from mycelial mass of a liquid culture in Potato Dextrose Broth (Difco™ Cat. No. 254920) using the BIO101 Fast Prep® System according to the method described by the supplier (Qbiogene). The DNA was purified using a Quick Spin column (Qiagen art No. 28106). The glucoamylase gene was isolated using primers with GA-specific sequences, NSP232R (SEQ ID NO: 24) and NSP233F (SEQ ID NO: 25) designed according to the predicted nucleotide sequence in the Trichoderma reesei genome database of Department of Energy (DOE) Joint Genome Institute. The primers were flanked at the 5'-end by Gateway® attB sequences (Invitrogen). *T. reesei* QM6a chromosomal DNA was used as template.

The PCR mix contained the following components: Forward primer (10 μM) 4 μL; Reverse primer (10 μM) 4 μL; template DNA (500 ng/μL) 1 μL; dNTPmix (10 mM) 2 μL; 10×Cx buffer 10 μL and PfuTurbo® Cx Hotstart DNA polymerase 0.5 μL (Stratagen Cat. No. 600410). Deionized water was added up to a total volume of 100 μL.

The PCR protocol was as follows: Initial denaturation for 30 sec. at 98° C., denaturation, annealing and extension in 30 cycles of 10 sec at 98° C.; 30 sec at 68° C.; 45 sec at 72° C., respectively, and a final extension step of 10 min at 72° C.

The PCR fragments were analyzed by electrophoresis in 1% agarose. Fragments of the expected size were isolated using the Gel-Extraction Purification Kit (Qiagene Cat. no. 28706). The PCR fragments were cloned into the Gateway® Entry vector pDONR201 and transformed into *E. coli* DH5alpha Max Efficiency cells (Invitrogen Cat. No. 18258012). The nucleotide sequence of the inserted DNA was determined, from which the genomic DNA sequence of the TrGA gene was deduced (FIG. 1 (SEQ ID NO: 1)).

Example 2

Transformation of *T. reesei* and Fermentation/Expression of the TrGA

Vector DNA containing the correct GA gene sequence was recombined into the *T. reesei* expression vector pTrex3g (FIG. 17).

The vector pTrex3g is based on the *E. coli* vector pSL1180 (Pharmacia Inc., Piscataway, N.J.) which is a pUC118 phagemid based vector (Brosius, J. (1989), *DNA* 8:759) with an extended multiple cloning site containing 64 hexamer restriction enzyme recognition sequences. It was designed as a Gateway destination vector (Hartley et al., (2000) *Genome Research* 10:1788-1795) to allow insertion using Gateway technology (Invitrogen) of any desired open reading frame between the promoter and terminator regions of the *T. reesei* cbh1 gene. It also contains the *Aspergillus nidulans* amdS gene for use as a selective marker in transformation of *T. reesei*. The details of the pTrex3g vector are as follows (FIG. 17A). The vector is 10.3 kb in size. Inserted into the polylinker region of pSL1180 are the following segments of DNA: a) A 2.2 bp segment of DNA from the promoter region of the *T. reesei* cbh1 gene; b) the 1.7 kb Gateway reading frame A cassette acquired from Invitrogen that includes the attR1 and attR2 recombination sites at either end flanking the chloramphenicol resistance gene (CmR) and the ccclB gene; c) a 336 bp segment of DNA from the terminator region of the *T. reesei* cbh1 gene; and d) a 2.7 kb fragment of DNA containing the *Aspergillus nidulans* amdS gene with its native promoter and terminator regions.

The expression vector containing the *T. reesei* GA gene, pNSP23 (FIG. 17) was transformed into a *T. reesei* host strain derived from RL-P37 (IA52) and having various gene deletions (Δcbh1, Δcbh2, Δeg1, Δeg2) using particle bombardment by the PDS-1000/Helium System (BioRad Cat. No. 165-02257). The protocol is outlined below, and reference is also made to examples 6 and 11 of WO 05/001036.

A suspension of spores (approximately $5 \times 10^8$ spores/ml) from a quad deleted strain of *T. reesei* was prepared. 100 ul-200 ul of spore suspension was spread onto the center of plates of Minimal Medium (MM) acetamide medium. (MM acetamide medium had the following compositions: 0.6 g/L acetamide; 1.68 g/LCsCl; 20 g/L glucose; 20 g/L $KH_2PO_4$; 0.6 g/L $CaCl_2$ $2H_2O$; 1 ml/L 1000× trace elements solution; 20 g/L Noble agar; and pH 5.5. 1000× trace elements solution contained 5.0 g/L $FeSO_4$ $7H_2O$; 1.6 g/L $MnSO_4$; 1.4 g/L $ZnSO_4$ $7H_2O$ and 1.0 g/L $CoCl_2$ $6H_2O$. The spore suspension was allowed to dry on the surface of the MM acetamide medium.

Transformation followed the manufacturers instruction. Briefly, 60 mg of M10 tungsten particles were placed in a microcentrifuge tube. 1 mL of ethanol was added and allowed to stand for 15 seconds. The particles were centrifuged at 15,000 rpm for 15 seconds. The ethanol was removed and the particles were washed three times with sterile dH$_2$O before 250 uL of 50% (v/v) sterile glycerol was added. 25 ul of tungsten particle suspension was placed into a microtrifuge tube. While continuously vortexing, the following were added: 5 ul (100-200 ng/ul) of plasmid DNA, 25 ul of 2.5M CaCl$_2$ and 10 ul of 0.1M spermidine. The particles were centrifuged for 3 seconds. The supernatant was removed and the particles were washed with 200 ul of 100% ethanol and centrifuged for 3 seconds. The supernatant was removed, 24 uL 100% ethanol was added and mixed by pipetting, then 8 ul aliquots of particles were removed and placed onto the center of macrocarrier disks that were held in a desiccator. Once the tungsten/DNA solution had dried the macrocarrier disk was placed in the bombardment chamber along with the plate of MM acetamide with spores and the bombardment process was performed according to the manufacturers instructions. After bombardment of the plated spores with the tungsten/DNA particles, the plates were incubated at 30° C. Transformed colonies were transferred to fresh plates of MM acetamide medium and incubated at 30° C.

Example 3

Demonstration of GA Activity from the Expressed TrGA in Transformed Cells

After 5 days of growth on MM acetamide plates transformants displaying stable morphology were inoculated into 250 ml shake flasks containing 30 ml of Proflo medium. (Proflo medium contained: 30 g/L α-lactose; 6.5 g/L (NH$_4$)$_2$SO$_4$; 2 g/L KH$_2$PO$_4$; 0.3 g/L MgSO$_4$ 7H$_2$O; 0.2 g/L CaCl$_2$; 1 ml/L 1000× trace element salt solution; 2 ml/L 10% Tween 80; 22.5 g/L ProFlo cottonseed flour (Traders protein, Memphis, Tenn.); 0.72 g/L CaCO$_3$. After two days growth at 28 C and 140 rpm, 10% of the Proflo culture was transferred to a 250 ml shake flask containing 30 ml of Lactose Defined Media. The composition of the Lactose defined Media was as follows 5 g/L (NH$_4$)$_2$SO$_4$; 33 g/L PIPPS buffers; 9 g/L casamino acids; 4.5 g/L KH$_2$PO$_4$; 1.0 g/L MgSO$_4$ 7H$_2$O; 5 ml/L Mazu DF60-P antifoam (Mazur Chemicals, IL); 1000× trace element solution; pH 5.5; 40 ml/L of 40% (w/v) lactose solution was added to the medium after sterilization. The Lactose Defined medium shake flasks were incubated at 28° C., 140 rpm for 4-5 days.

Mycelium was removed by centrifugation and the supernatant was analyzed for total protein (BCA Protein Assay Kit, Pierce Cat. No. 23225) and GA activity using pNPG as substrate (Sigma N-1377).

Samples of the culture supernatant were mixed with appropriate volume of 2× sample loading buffer with reducing agent and the protein profile was determined by sodium dodecyl sulfate-polyacrylamide gel electrophoresis (SDS-PAGE) using NuPAGE® Novex 10% Bis-Tris Gel with MES SDS Running Buffer. The gels were stained with SimplyBlue™ SafeStain (Invitrogen, Carlsbad, Calif., USA).

On SDS-PAGE analysis a protein band that was not observed in supernatant from a quad delete strain was observed in the supernatant of some transformants with the pTrex3g vector containing the glucoamylase open reading frame (FIG. 16). This new protein band had an apparent molecular weight of approximately 64 kDa. This result confirms that TrGA is secreted into the medium.

Example 4

Biochemical Characterization of the GA Gene Product

GA producing transformants were grown at 4-L scale. The culture filtrate was concentrated using an ultra filtration unit with a nominal molecular weight limit of 10,000 Da (Pall Omega Centramate OSO10c10). The crude enzyme preparation was purified by a 2-step procedure using an ÄKTA explorer 100 FPLC System (Amersham Biosciences). A HiPrep 16/10 FF Q-Sepharose column (Amersham BioSciences Cat. No. 17-5190-01) was equilibrated with 25 mM Tris pH 8.0 and the protein was eluted from the column with 100 mM NaCl in 25 mM Tris pH 8.0. A second affinity chromatography step was performed using Cbind 200 resin (Novagen Cat. No. 701212-3) and 50 mM Tris pH 7.0 containing 500 mM NaCl as elution buffer (FIG. 16). The N-terminus of the gene product (Ser-Val-Asp-Asp-Phe-Ile) (SEQ ID NO: 38) was determined by Edman degradation (Edman, P. (1956) *Acta Chem Scand* 10:761-768).

The pH and temperature profiles of the glucoamylase activity of the gene product were determined using 4-nitrophenyl-α-D-glucopyranoside as substrate (Elder, M. T. and Montgomery R. S., Glucoamylase activity in industrial enzyme preparations using colorimetric enzymatic method; Collaborative study Journal of AOAC International, vol. 78(2), 1995) (FIG. 18).

Example 5

Isolation/cloning of Glucoamylase Homologs from Strains in the Trichoderma/Hypocrea Family Cluster Chromosomal DNA preparations of the strains (GA102)—*Hypocrea citrina* var. *americana* (CBS976.69); (GA104)—*Hypocrea vinosa* (CBS960.68); (GA105)—*Trichoderma* sp; (GA107)—*Hypocrea gelatinosa* (CBS254.62); GA108—*Hypocrea orientalis* (ATCC 90550); (GA109)—*Trichoderma konilangbra*; (GA103)—*Trichoderma harzianum* (CBS433.95); (GA113)—*Trichoderma* sp.; (GA124)—*Trichoderma longibrachiatum*; (GA127)—*Trichoderma asperellum* (ATCC 28020); and (GA128)—*Trichoderma strictipilis* (CBS 347.93) were isolated as described in example 1. Full-length GA genes were cloned as described in example 1 using the TrGA-gene specific primers NSP231 F (SEQ ID NO: 23) and NSP232R (SEQ ID NO: 24). The nucleotide sequences of the strains are disclosed in FIG. 4 for GA102 (SEQ ID NO: 5); FIG. 5 for GA104 (SEQ ID NO: 7); FIG. 6 for GA105 (SEQ ID NO: 9); FIG. 7 for GA107 (SEQ ID NO: 11); FIG. 8 for GA108 (SEQ ID NO: 13); FIG. 9 for GA109 (SEQ ID NO: 15); FIG. 10 for GA113 (SEQ ID NO: 28); FIG. 11 for GA103 (SEQ ID NO: 30); FIG. 12 for GA124 (SEQ ID NO: 32); FIG. 13 for GA127 (SEQ ID NO: 34) and FIG. 14 for GA128 (SEQ ID NO: 36). The corresponding amino acid sequences are illustrated in FIG. 15. Table 2 sets forth the percent identity of the amino acid sequences of the mature protein of *T. reesei* glucoamylase (FIG. 3B, SEQ ID NO: 4) with the glucoamylase homologs from the Hypocrea/Trichoderma cluster.

TABLE 2

% Identity of GA homologs from the Hypocrea/Trichoderma cluster

|  | GA102 | GA103 | GA104 | GA105 | GA107 | GA108 | GA109 | GA113 | GA124 | GA127 | GA128 | TrGA |
|---|---|---|---|---|---|---|---|---|---|---|---|---|
| GA102 | 100 | 86 | 86 | 84 | 87 | 84 | 84 | 83 | 84 | 87 | 85 | 84 |
| GA103 |  | 100 | 98 | 90 | 96 | 90 | 91 | 86 | 90 | 98 | 90 | 90 |
| GA104 |  |  | 100 | 91 | 97 | 91 | 90 | 86 | 91 | 99 | 90 | 91 |
| GA105 |  |  |  | 100 | 90 | 95 | 93 | 83 | 94 | 91 | 94 | 95 |
| GA107 |  |  |  |  | 100 | 90 | 90 | 86 | 90 | 98 | 90 | 90 |
| GA108 |  |  |  |  |  | 100 | 94 | 84 | 98 | 91 | 94 | 97 |
| GA109 |  |  |  |  |  |  | 100 | 83 | 94 | 91 | 94 | 94 |
| GA113 |  |  |  |  |  |  |  | 100 | 84 | 86 | 83 | 84 |
| GA124 |  |  |  |  |  |  |  |  | 100 | 91 | 94 | 98 |
| GA127 |  |  |  |  |  |  |  |  |  | 100 | 91 | 91 |
| GA128 |  |  |  |  |  |  |  |  |  |  | 100 | 94 |
| TrGA |  |  |  |  |  |  |  |  |  |  |  | 100 |

*T. reesei* strains over-expressing GA were obtained as described in example 2. Crude enzyme preparations were obtained as described in example 3 and FIG. 19 illustrates the gels obtained for some of the homologs. Table 3 sets forth the glucoamylase activity of some of the homologs.

TABLE 3

| Strain | Gene from: | Total protein mg/mL | U GA/mL | Specific Activity |
|---|---|---|---|---|
| GA104 | *H. vinosa* | 2.76 | 37 | 13 |
| GA105 | *T. sp.* | 2.77 | 26 | 9 |
| GA107 | *H. gelatinosa* | 3.61 | 178 | 49 |
| GA109 | *T. konilangbra* | 2.22 | 10 | 5 |
| TrGA | *T. reesei* | 3.89 | 91 | 23 |
| Host Control | *T. reesei* | 0.7 | 3 | 4 |

Example 6

Glucose Production using TrGA

A 32% DS slurry of Cargill bag starch was made up with reverse osmosis water. The pH of the slurry was adjusted to pH 5.8. The slurry was filtered through a 100-mesh screen and dosed at 4.0 AAU/g ds using SPEZYME® ETHYL, (Genencor International, Inc.) The slurry was then jetted at 107.3° C. for 5 min (primary liquefaction). Enzyme activity is determined by the rate of starch hydrolysis, as reflected in the rate of decrease in iodine-staining capacity. One AAU unit of bacterial alpha amylase activity is the amount of enzyme required to hydrolyze 10 mg of starch per minute under specified conditions. After primary liquefaction, the liquefact was collected and placed in a 95° C. water bath for 120 min (Secondary liquefaction). Samples were taken at 30, 60, 90 and 120 min and checked for DE by using the standard Schoorls reducing sugar method from the Corn Refiners Association. The liquefact was aliquoted in 100-g quantities into screw cap jars, the pH was adjusted to pH 4.5 and equilibrated to 60° C. for 15 minutes prior to dosing. The TrGA enzyme was diluted so as to add 0.2 mls of diluted enzyme to the jar at 0.22 GAU/g ds. After dosing, the liquefact was aliquoted into 7 screw cap tubes, each containing approximately 10 mls of material and returned to the designated temperature. Tubes were removed at selected time intervals (18, 24, 30, 42, 50 and 55 hours) and analyzed by HPLC Carbohydrate System: Column: Phenomenex Rezex Carbohydrate (RCM-Monosaccharide) #00H-0130-KO (Equivalent to Bio-Rad 87H); Column Temperature: 70° C.; Mobile Phase: Nanopure DI $H_2O$; Flow Rate: 0.8 mL/min; Detector: RI; Injection Volume: 10 uL (3% DS material) for sugar composition.

TABLE 4

Production of Glucose from cornstarch using TrGA

| Treatment (hrs) | % DP1 | % DP2 | % DP3 | % DP > 3 |
|---|---|---|---|---|
| 18 | 80.66 | 2.60 | 0.66 | 16.08 |
| 24 | 84.25 | 2.31 | 0.46 | 12.98 |
| 30 | 86.26 | 2.66 | 0.47 | 10.61 |
| 42 | 88.85 | 3.05 | 0.40 | 7.69 |
| 50 | 89.93 | 3.26 | 0.42 | 6.39 |
| 55 | 90.64 | 3.36 | 0.37 | 5.62 |

Example 7

Ethanol Production using TrGA in a Simultaneous Saccharification and Fermentation (SSF) Process A sample of corn mash liquefact from a local ethanol producer was obtained and diluted to 29% DS using thin stillage. The pH of the slurry was adjusted to pH 4.3 using 6 N sulfuric acid. A 300 g aliquot of the mash was placed into a 31° C. water bath and allowed to equilibrate. TrGA was added to the sample (0.4 GAU/g ds, which is equal to 1.08 kg/MT ds). After enzyme addition, 1 ml of a 15 g in 45 ml DI water solution of Red Star Red yeast (Lesaffre yeast Corp. Milwaukee, Wis.) was added to each sample. Samples were taken at 18, 26, 41 and 53 hours and analyzed by HPLC Column: Phenomenex Rezex organic Acid Column (RHM-Monosaccharide) #00H-0132-KO (Equivalent to Bio-Rad 87H); Column Temperature: 60° C.; Mobile Phase: 0.01 $NH_2SO_4$; Flow Rate: 0.6 mL/min; Detector: RI; Injection Volume: 20 uL.

TABLE 5

Production of Ethanol by TrGA (0.4 GAU/g) in a SSF Process

| Sample (hrs) | % w/v DP > 3 | % w/v DP-3 | % w/v DP-2 | % w/v DP-1 | % w/v Lactic Acid | % w/v Glycerol | % v/v EtOH |
|---|---|---|---|---|---|---|---|
| 18 | 6.38 | 0.61 | 3.42 | 2.69 | 0.31 | 0.97 | 7.44 |
| 26 | 4.39 | 0.76 | 1.02 | 1.81 | 0.30 | 1.12 | 10.68 |

TABLE 5-continued

Production of Ethanol by TrGA (0.4 GAU/g) in a SSF Process

| Sample (hrs) | % w/v DP > 3 | % w/v DP-3 | % w/v DP-2 | % w/v DP-1 | % w/v Lactic Acid | % w/v Glycerol | % v/v EtOH |
|---|---|---|---|---|---|---|---|
| 41 | 1.62 | 0.47 | 0.35 | 0.77 | 0.31 | 1.27 | 13.65 |
| 53 | 1.03 | 0.37 | 0.36 | 0.16 | 0.32 | 1.32 | 14.46 |

Example 8

A Non-cook Process for Ethanol Production using TrGA

In general a 33% slurry of corn flour (Azure Standard Farms) was prepared in DI $H_2O$ to which 400 ppm urea was added. The pH was adjusted to 4.5. Fermentations were conducted in 125 ml flasks containing 100 g mash and various treatments of GAU/g TrGA. A 20% slurry of Fali dry yeast in water was prepared and mixed with a 32° C. water bath one hour prior to inoculating the fermenters by adding 0.2 ml of the yeast slurry. The flasks were placed in a 32° C. water bath and the mash mix gently. During the fermentations samples were removed for HPLC analysis. The fermentations were terminated after 72 hours. Production of compounds including sugars, lactic acid, glycerol and ethanol at various sampling intervals is shown below in various tables. The mash was dried at 60° C. to obtain the DDGS, and the starch content of the DDGS was determined by the dual enzyme method.

A. All conditions were as described above: the treatment included 1.2 GAU/g TrGA.

TABLE 6

Ethanol Production

| Treatment | Hrs | % W/V DP > 3 | % W/V DP-3 | % W/V DP-2 | % W/V DP-1 | % W/V Lactic | % W/V Glycerol | % V/V EtOH |
|---|---|---|---|---|---|---|---|---|
| TrGA | 17 | 0.68 | 0.05 | 0.04 | 0.00 | 0.04 | 0.41 | 4.70 |
| TrGA | 24 | 0.67 | 0.06 | 0.05 | 0.02 | 0.04 | 0.42 | 5.44 |
| TrGA | 41 | 0.65 | 0.07 | 0.00 | 0.00 | 0.05 | 0.44 | 6.78 |
| TrGA | 48 | 0.59 | 0.08 | 0.08 | 0.00 | 0.07 | 0.43 | 7.77 |

TABLE 6-continued

Ethanol Production

| Treatment | Hrs | % W/V DP > 3 | % W/V DP-3 | % W/V DP-2 | % W/V DP-1 | % W/V Lactic | % W/V Glycerol | % V/V EtOH |
|---|---|---|---|---|---|---|---|---|
| TrGA | 64 | 0.61 | 0.08 | 0.00 | 0.00 | 0.15 | 0.43 | 8.42 |
| TrGA | 72 | 0.60 | 0.08 | 0.07 | 0.01 | 0.17 | 0.43 | 8.59 |

B. All conditions were as described above: the treatments included 0.75 GAU/g GA107 and 0.75GAU/g GA104

TABLE 7

Ethanol Production

| GA | hrs | % w/v DP > 3 | % w/v DP-3 | % w/v DP-2 | % w/v DP-1 | % w/v Lactic | % w/v Glycerol | % v/v ETOH |
|---|---|---|---|---|---|---|---|---|
|  |  | 1.11 | 0.10 | 0.29 | 1.06 | 0.00 | 0.15 | 0.00 |
| 104 | 13 | 0.84 | 0.00 | 0.01 | 0.01 | 0.00 | 0.43 | 5.03 |
| 107 | 13 | 0.77 | 0.00 | 0.00 | 0.00 | 0.00 | 0.42 | 4.16 |
| 104 | 21 | 0.94 | 0.14 | 0.03 | 0.00 | 0.00 | 0.46 | 6.90 |
| 107 | 21 | 0.88 | 0.10 | 0.03 | 0.01 | 0.00 | 0.43 | 5.24 |
| 104 | 35 | 0.94 | 0.18 | 0.13 | 0.02 | 0.02 | 0.49 | 9.02 |
| 107 | 35 | 0.87 | 0.11 | 0.02 | 0.01 | 0.04 | 0.44 | 6.53 |
| 104 | 54 | 0.91 | 0.14 | 0.00 | 0.00 | 0.00 | 0.51 | 10.93 |
| 107 | 54 | 0.89 | 0.13 | 0.00 | 0.00 | 0.30 | 0.45 | 7.58 |
| 104 | 62 | 0.87 | 0.12 | 0.00 | 0.00 | 0.00 | 0.53 | 11.49 |
| 107 | 62 | 0.88 | 0.14 | 0.00 | 0.00 | 0.39 | 0.46 | 7.74 |
| 104 | 72 | 0.94 | 0.14 | 0.16 | 0.00 | 0.00 | 0.53 | 12.22 |
| 107 | 72 | 0.88 | 0.14 | 0.05 | 0.01 | 0.42 | 0.47 | 7.82 |

C. All conditions were as described above: the treatments included a) *A. niger* GA 0.75 GAU/g+2.25 SSU AkAA and b) TrGA 0.75 GAU/g+2.25 SSU AkAA. The residual starch for AnGA+AkAA treatment was determined to be 5.26% and the residual starch for TrGA+AkAA treatment was determined to be 8.71%.

The measurement of alpha amylase activity for AkAA is based on the degree of hydrolysis of soluble potato starch substrate (4% ds) by an aliquot of the enzyme sample at pH 4.5, 50° C. The reducing sugar content is measured using the DNS method as described in Miller, G. L. (1959) *Anal. Chem.* 31:426-428. One unit of the enzyme activity (SSU, soluble starch unit) is equivalent to the reducing power of 1 mg of glucose released per minute at the specific incubation conditions.

TABLE 8

Ethanol Production

| Treatment | Hours | % W/V DP > 3 | % W/V DP-3 | % W/V DP-2 | % W/V DP-1 | % W/V Lactic | % W/V Glycerol | % V/V Ethanol |
|---|---|---|---|---|---|---|---|---|
| AnGA + AkAA | 15 | 0.81 | 0.00 | 0.04 | 0.13 | 0.04 | 0.63 | 8.22 |
| TrGA + AkAA | 15 | 0.94 | 0.00 | 0.04 | 0.03 | 0.04 | 0.68 | 8.35 |
| AnGA + AkAA | 26.5 | 0.94 | 0.06 | 0.04 | 0.08 | 0.06 | 0.89 | 12.59 |
| TrGA + AkAA | 26.5 | 1.00 | 0.08 | 0.08 | 0.00 | 0.06 | 0.83 | 11.81 |

TABLE 8-continued

| | | Ethanol Production | | | | | | |
|---|---|---|---|---|---|---|---|---|
| Treatment | Hours | % W/V DP > 3 | % W/V DP-3 | % W/V DP-2 | % W/V DP-1 | % W/V Lactic | % W/V Glycerol | % V/V Ethanol |
| AnGA + AkAA | 40 | 0.65 | 0.10 | 0.08 | 0.05 | 0.06 | 0.94 | 14.37 |
| TrGA + AkAA | 40 | 0.73 | 0.10 | 0.14 | 0.00 | 0.05 | 0.91 | 13.80 |
| AnGA + AkAA | 49 | 0.93 | 0.07 | 0.06 | 0.05 | 0.05 | 1.08 | 17.05 |
| TrGA + AkAA | 49 | 0.98 | 0.08 | 0.14 | 0.00 | 0.04 | 0.97 | 15.52 |
| AnGA + AkAA | 70 | 0.82 | 0.04 | 0.04 | 0.27 | 0.00 | 1.07 | 17.59 |
| TrGA + AkAA | 70 | 0.95 | 0.08 | 0.04 | 0.00 | 0.00 | 1.01 | 17.17 |

D. All conditions were as described above: the treatments included a) TrGA 0.695 GAU/g+2.25 SSU AkAA and b) TrGA 0.695 GAU/g+2.25 SSU AKAA+2 ASPU/g Pullulanase. One acid stable pullulanase unit (ASPU) is defined as the amount of enzyme which liberates one equivalent reducing potential as glucose per minute from pullulan at pH 4.5 and a temperature of 60° C.

TABLE 9

| | | Ethanol production | | | | | | | |
|---|---|---|---|---|---|---|---|---|---|
| Treatment | Hours | % W/V DP > 3 | % W/V DP-3 | % W/V DP-2 | % W/V DP-1 | % W/V Lactic | % W/V Glycerol | % V/V Ethanol | DDGS % starch |
| TrGA | 15 | 0.92 | 0.05 | 0.05 | 0.04 | 0.03 | 0.60 | 7.69 | |
| TrGA + Pullulanase | 15 | 0.91 | 0.05 | 0.04 | 0.04 | 0.03 | 0.60 | 8.00 | |
| TrGA | 24 | 0.94 | 0.08 | 0.09 | 0.05 | 0.04 | 0.72 | 10.46 | |
| TrGA + Pullulanase | 24 | 0.91 | 0.12 | 0.10 | 0.05 | 0.04 | 0.73 | 10.93 | |
| TrGA | 41 | 0.91 | 0.10 | 0.17 | 0.05 | 0.04 | 0.86 | 13.89 | |
| TrGA + Pullulanase | 41 | 0.92 | 0.13 | 0.16 | 0.04 | 0.05 | 0.87 | 14.33 | |
| TrGA | 47 | 0.87 | 0.10 | 0.20 | 0.05 | 0.04 | 0.90 | 14.51 | |
| TrGA + Pullulanase | 47 | 0.94 | 0.13 | 0.19 | 0.04 | 0.03 | 0.91 | 15.32 | |
| TrGA | 70 | 0.92 | 0.11 | 0.06 | 0.03 | 0.00 | 0.98 | 17.27 | 18.5 |
| TrGA + Pullulanase | 70 | 0.95 | 0.11 | 0.05 | 0.02 | 0.00 | 0.98 | 17.77 | 16.4 |

E. All conditions were as described above: the treatments included TrGA 0.695 GAU/g and the following AkAA treatments: a) 3 SSU AkAA; b) 10 SSU AkAA and c) 30 SSU AkAA.

TABLE 10

| Treatment (AkAA) | Hours | % w/v DP > 3 | % w/v DP-3 | % w/v DP-2 | % w/v DP-1 | % w/v Lactic | % w/v Glycerol | % v/v Ethanol | % starch DDGS |
|---|---|---|---|---|---|---|---|---|---|
| 3 SSU | 17 | 0.77 | 0.05 | 0.00 | 0.00 | 0.04 | 0.59 | 8.31 | |
| 10 SSU | 17 | 0.76 | 0.04 | 0.03 | 0.00 | 0.03 | 0.62 | 8.85 | |
| 30 SSU | 17 | 0.78 | 0.04 | 0.05 | 0.00 | 0.03 | 0.06 | 9.54 | |
| 3 SSU | 30 | 0.74 | 0.07 | 0.05 | 0.00 | 0.05 | 0.73 | 11.35 | |
| 10 SSU | 30 | 0.78 | 0.06 | 0.05 | 0.00 | 0.05 | 0.81 | 12.62 | |
| 30 SSU | 30 | 0.85 | 0.71 | 0.05 | 0.03 | 0.05 | 0.84 | 13.91 | |
| 3 SSU | 41 | 0.70 | 0.08 | 0.02 | 0.02 | 0.05 | 0.90 | 13.96 | |
| 10 SSU | 41 | 0.69 | 0.08 | 0.02 | 0.03 | 0.05 | 0.91 | 15.02 | |
| 30 SSU | 41 | 0.68 | 0.07 | 0.03 | 0.07 | 0.05 | 0.92 | 15.83 | |
| 3 SSU | 51 | 0.73 | 0.09 | 0.09 | 0.04 | 0.05 | 0.98 | 15.38 | |
| 10 SSU | 51 | 0.74 | 0.09 | 0.05 | 0.05 | 0.04 | 0.99 | 16.57 | |
| 30 SSU | 51 | 0.73 | 0.08 | 0.04 | 0.03 | 0.04 | 0.96 | 16.53 | |
| 3 SSU | 70 | 0.70 | 0.09 | 0.02 | 0.02 | 0.02 | 1.04 | 17.09 | 15.8 |
| 10 SSU | 70 | 0.72 | 0.08 | 0.02 | 0.03 | 0.04 | 1.04 | 17.35 | 10.7 |
| 30 SSU | 70 | 0.71 | 0.08 | 0.02 | 0.07 | 0.03 | 1.01 | 17.42 | 9.6 |

What is claimed is:

1. An isolated DNA sequence encoding an enzyme having glucoamylase activity, wherein the enzyme has an amino acid sequence that has at least 90% sequence identity with the glucoamylase of SEQ ID NO: 4.

2. The isolated DNA sequence of claim 1, wherein the enzyme has an amino acid sequence that has at least 95% sequence identity with the glucoamylase of SEQ ID NO: 4.

3. The isolated DNA sequence of claim 2, wherein the enzyme has an amino acid sequence that has at least 99% sequence identity with the glucoamylase of SEQ ID NO: 4.

4. The isolated DNA sequence of claim 1 wherein the DNA sequence is SEQ ID NO: 1.

5. The isolated DNA sequence of claim 1 wherein the DNA sequence is SEQ ID NO: 2.

6. The isolated DNA sequence of claim 1, wherein the enzyme is obtained from a filamentous fungus.

7. The isolated DNA sequence of claim 6, wherein the filamentous fungus is a *Trichoderma* or *Hypocrea*.

8. The isolated DNA sequence of claim 7, wherein the filamentous fungus is a strain of *Trichoderma reesei*.

9. A vector comprising the DNA of claim 1.

10. An isolated host cell transformed with the vector of claim 9.

11. The host cell of claim 10, wherein the host cell is obtained from a strain of a filamentous fungus.

12. The host cell of claim 11, wherein the filamentous fungal strain is *Trichoderma*.

13. The host cell of claim 12, wherein the *Trichoderma* is *T. reesei*.

14. A culture medium from the fermentation of a filamentous fungal host cell transformed with a nucleic acid sequence coding for a polypeptide having glucoamylase activity and at least 90% sequence identity to SEQ ID NO: 4.

15. The culture medium of claim 14, wherein the filamentous fungal host cell is a *Trichoderma* cell.

16. A method of recombinantly producing a glucoamylase, comprising the step of expressing a polynucleotide encoding a polypeptide having glucoamylase activity in a filamentous fungal host cell, wherein the polynucleotide comprises the isolated DNA sequence of claim 1, and producing said glucoamylase.

17. The method according to claim 16, wherein the polypeptide further comprises a sequence that encodes a signal peptide.

18. The method according to claim 17, wherein the signal peptide comprises an amino acid sequence which has at least 95% sequence identity to the sequence shown in positions 1 to 20 of SEQ ID NO: 3.

19. The method according to claim 16, wherein the filamentous fungal host cell is a *Trichoderma* cell.

20. The method according to claim 19, wherein the *Trichoderma* host is *T. reesei*.

21. The method according to claim 16, further comprising recovering the produced glucoamylase.

* * * * *

SEQUENCE LISTING

<160> NUMBER OF SEQ ID NOS: 47

<210> SEQ ID NO 1
<211> LENGTH: 2147
<212> TYPE: DNA
<213> ORGANISM: Trichoderma reesei

<400> SEQUENCE: 1

| | | | | | |
|---|---|---|---|---|---:|
| atgcacgtcc | tgtcgactgc | ggtgctgctc | ggctccgttg | ccgttcaaaa | ggtcctggga | 60 |
| agaccaggat | caagcggtct | gtcgacgtca | ccaagaggtc | tgttgacgac | ttcatcagca | 120 |
| ccgagacgcc | tattgcactg | aacaatcttc | tttgcaatgt | tggtcctgat | ggatgccgtg | 180 |
| cattcggcac | atcagctggt | gcggtgattg | catctcccag | cacaattgac | ccggactgta | 240 |
| agttggcctt | gatgaaccat | atcatatatc | gccgagaagt | ggaccgcgtg | ctgagactga | 300 |
| gacagactat | tacatgtgga | cgcgagatag | cgctcttgtc | ttcaagaacc | tcatcgaccg | 360 |
| cttcaccgaa | acgtacgatg | cgggcctgca | gcgccgcatc | gagcagtaca | ttactgccca | 420 |
| ggtcactctc | cagggcctct | ctaaccccctc | gggctcccctc | gcggacggct | ctggtctcgg | 480 |
| cgagcccaag | tttgagttga | ccctgaagcc | tttcaccggc | aactggggtc | gaccgcagcg | 540 |
| ggatggccca | gctctgcgag | ccattgcctt | gattggatac | tcaaagtggc | tcatcaacaa | 600 |
| caactatcag | tcgactgtgt | ccaacgtcat | ctggcctatt | gtgcgcaacg | acctcaacta | 660 |
| tgttgcccag | tactggtcag | tgcttgcttg | ctcttgaatt | acgtctttgc | ttgtgtgtct | 720 |
| aatgcctcca | ccacaggaac | caaaccggct | ttgacctctg | ggaagaagtc | aatgggagct | 780 |
| cattctttac | tgttgccaac | cagcaccgag | gtatgaagca | atcctcgac | attcgctgct | 840 |
| actgcacatg | agcattgtta | ctgaccagct | ctacagcact | tgtcgagggc | gccactcttg | 900 |
| ctgccactct | tggccagtcg | ggaagcgctt | attcatctgt | tgctccccag | gttttgtgct | 960 |
| ttctccaacg | attctgggtg | tcgtctggtg | gatacgtcga | ctccaacagt | atgtctttc | 1020 |
| actgtttata | tgagattggc | caatactgat | agctcgcctc | tagtcaacac | caacgagggc | 1080 |
| aggactggca | aggatgtcaa | ctccgtcctg | acttccatcc | acaccttcga | tcccaaccctt | 1140 |
| ggctgtgacg | caggcacctt | ccagccatgc | agtgacaaag | cgctctccaa | cctcaaggtt | 1200 |
| gttgtcgact | ccttccgctc | catctacggc | gtgaacaagg | gcattcctgc | cggtgctgcc | 1260 |
| gtcgccattg | gccggtatgc | agaggatgtg | tactacaacg | gcaacccttg | gtatcttgct | 1320 |
| acatttgctg | ctgccgagca | gctgtacgat | gccatctacg | tctggaagaa | gacgggctcc | 1380 |
| atcacggtga | ccgccaccctc | cctggccttc | ttccaggagc | ttgttcctgg | cgtgacggcc | 1440 |
| gggacctact | ccagcagctc | ttcgaccttt | accaacatca | tcaacgccgt | ctcgacatac | 1500 |
| gccgatggct | tcctcagcga | ggctgccaag | tacgtccccg | ccgacggttc | gctggccgag | 1560 |
| cagtttgacc | gcaacagcgg | cactccgctg | tctgcgcttc | acctgacgtg | gtcgtacgcc | 1620 |
| tcgttcttga | cagccacggc | ccgtcgggct | ggcatcgtgc | cccctcgtg | ggccaacagc | 1680 |
| agcgctagca | cgatcccctc | gacgtgctcc | ggcgcgtccg | tggtcggatc | ctactcgcgt | 1740 |
| cccaccgcca | cgtcattccc | tccgtcgcag | acgcccaagc | ctggcgtgcc | ttccggtact | 1800 |
| ccctacacgc | ccctgccctg | cgcgacccca | acctccgtgg | ccgtcacctt | ccacgagctc | 1860 |
| gtgtcgacac | agtttggcca | gacggtcaag | gtggcgggca | acgccgcggc | cctgggcaac | 1920 |
| tggagcacga | gcgccgccgt | ggctctggac | gccgtcaact | atgccgataa | ccaccccctg | 1980 |
| tggattggga | cggtcaacct | cgaggctgga | gacgtcgtgg | agtacaagta | catcaatgtg | 2040 |

```
ggccaagatg ctccgtgac ctgggagagt gatcccaacc acacttacac ggttcctgcg    2100
gtggcttgtg tgacgcaggt tgtcaaggag gaacctggca gtcgtaa                 2147

<210> SEQ ID NO 2
<211> LENGTH: 1899
<212> TYPE: DNA
<213> ORGANISM: Trichoderma reesei

<400> SEQUENCE: 2
atgcacgtcc tgtcgactgc ggtgctgctc ggctccgttg ccgttcaaaa ggtcctggga      60
agaccaggat caagcggtct gtccgacgtc accaagaggt ctgttgacga cttcatcagc    120
accgagacgc ctattgcact gaacaatctt ctttgcaatg ttggtcctga tggatgccgt    180
gcattcggca catcagctgg tgcggtgatt gcatctccca gcacaattga cccggactac    240
tattacatgt ggacgcgaga tagcgctctt gtcttcaaga acctcatcga ccgcttcacc    300
gaaacgtacg atgcgggcct gcagcgccgc atcgagcagt acattactgc ccaggtcact    360
ctccagggcc tctctaaccc ctcgggctcc ctcgcggacg gctctggtct cggcgagccc    420
aagtttgagt tgaccctgaa gcctttcacc ggcaactggg gtcgaccgca gcgggatggc    480
ccagctctgc gagccattgc cttgattgga tactcaaagt ggctcatcaa caacaactat    540
cagtcgactg tgtccaacgt catctggcct attgtgcgca acgacctcaa ctatgttgcc    600
cagtactgga accaaaccgg ctttgacctc tgggaagaag tcaatgggag ctcattcttt    660
actgttgcca ccagcaccg agcacttgtc gagggcgcca ctcttgctgc cactcttggc    720
cagtcgggaa gcgcttattc atctgttgct ccccaggttt tgtgctttct ccaacgattc    780
tgggtgtcgt ctggtggata cgtcgactcc aacatcaaca ccaacgaggg caggactggc    840
aaggatgtca actccgtcct gacttccatc cacaccttcg atcccaacct ggctgtgac     900 gcaggcacct tccagccatg cagtgacaaa gcgctctcca acctcaaggt tgttgtcgac    960
tccttccgct ccatctacgg cgtgaacaag ggcattcctg ccggtgctgc cgtcgccatt   1020
ggccggtatg cagaggatgt gtactacaac ggcaacccct tggtatcttg cacatttgct   1080
gctgccgagc agctgtacga tgccatctac gtctggaaga gacgggctc catcacggtg   1140 accgccacct cctggccttt cttccaggag cttgttcctg gcgtgacggc cgggacctac   1200
tccagcagct cttcgacctt taccaacatc atcaacgccg tctcgacata cgccgatggc   1260
ttcctcagca ggctgccaa gtacgtcccc gccgacggtt cgctggccga gcagtttgac   1320
cgcaacagcg gcactccgct gtctgcgctt cacctgacgt ggtcgtacgc ctcgttcttg   1380
acagccacgg cccgtcgggc tggcatcgtg ccccccctcgt gggccaacag cagcgctagc   1440
acgatcccct cgacgtgctc cggcgcgtcc gtggtcggat cctactcgcg tcccaccgcc   1500
acgtcattcc ctccgtcgca gacgcccaag cctggcgtgc cttccggtac tcctacacg   1560 cccctgccct gcgcgacccc aacctccgtg gccgtcacct tccacgagct cgtgtcgaca   1620
cagtttggcc agacggtcaa ggtggcgggc aacgccgcgg ccctgggcaa ctggagcacg   1680
agcgccgccg tggctctgga cgccgtcaac tatgccgata ccaccccct gtggattggg   1740 acggtcaacc tcgaggctgg agacgtcgtg gagtacaagt acatcaatgt gggccaagat   1800
ggctccgtga cctgggagag tgatcccaac cacacttaca cggttcctgc ggtggcttgt   1860
gtgacgcagg ttgtcaagga ggacacctgg cagtcgtaa                          1899

<210> SEQ ID NO 3
```

<211> LENGTH: 632
<212> TYPE: PRT
<213> ORGANISM: Trichoderma reesei

<400> SEQUENCE: 3

```
Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Ile Asp Pro Asp Tyr
65                  70                  75                  80

Tyr Tyr Met Trp Thr Arg Asp Ser Ala Leu Val Phe Lys Asn Leu Ile
                85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
        115                 120                 125

Gly Ser Leu Ala Asp Gly Ser Gly Leu Gly Glu Pro Lys Phe Glu Leu
    130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Asn Gly Ser Ser Phe Phe Thr Val Ala Asn
    210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
                245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Val Leu Thr
        275                 280                 285

Ser Ile His Thr Phe Asp Pro Asn Leu Gly Cys Asp Ala Gly Thr Phe
    290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
                325                 330                 335

Ala Val Ala Ile Gly Arg Tyr Ala Glu Asp Val Tyr Tyr Asn Gly Asn
            340                 345                 350

Pro Trp Tyr Leu Ala Thr Phe Ala Ala Ala Glu Gln Leu Tyr Asp Ala
        355                 360                 365

Ile Tyr Val Trp Lys Lys Thr Gly Ser Ile Thr Val Thr Ala Thr Ser
    370                 375                 380

Leu Ala Phe Phe Gln Glu Leu Val Pro Gly Val Thr Ala Gly Thr Tyr
```

-continued

```
                385                 390                 395                 400
Ser Ser Ser Ser Ser Thr Phe Thr Asn Ile Ile Asn Ala Val Ser Thr
                    405                 410                 415

Tyr Ala Asp Gly Phe Leu Ser Glu Ala Ala Lys Tyr Val Pro Ala Asp
                420                 425                 430

Gly Ser Leu Ala Glu Gln Phe Asp Arg Asn Ser Gly Thr Pro Leu Ser
                435                 440                 445

Ala Leu His Leu Thr Trp Ser Tyr Ala Ser Phe Leu Thr Ala Thr Ala
            450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
                    485                 490                 495

Arg Pro Thr Ala Thr Ser Phe Pro Pro Ser Gln Thr Pro Lys Pro Gly
                500                 505                 510

Val Pro Ser Gly Thr Pro Tyr Thr Pro Leu Pro Cys Ala Thr Pro Thr
                515                 520                 525

Ser Val Ala Val Thr Phe His Glu Leu Val Ser Thr Gln Phe Gly Gln
            530                 535                 540

Thr Val Lys Val Ala Gly Asn Ala Ala Ala Leu Gly Asn Trp Ser Thr
545                 550                 555                 560

Ser Ala Ala Val Ala Leu Asp Ala Val Asn Tyr Ala Asp Asn His Pro
                    565                 570                 575

Leu Trp Ile Gly Thr Val Asn Leu Glu Ala Gly Asp Val Val Glu Tyr
                580                 585                 590

Lys Tyr Ile Asn Val Gly Gln Asp Gly Ser Val Thr Trp Glu Ser Asp
                595                 600                 605

Pro Asn His Thr Tyr Thr Val Pro Ala Val Ala Cys Val Thr Gln Val
            610                 615                 620

Val Lys Glu Asp Thr Trp Gln Ser
625                 630

<210> SEQ ID NO 4
<211> LENGTH: 599
<212> TYPE: PRT
<213> ORGANISM: Trichoderma reesei

<400> SEQUENCE: 4

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Ile Asp Pro Asp Tyr Tyr
            35                  40                  45

Tyr Met Trp Thr Arg Asp Ser Ala Leu Val Phe Lys Asn Leu Ile Asp
        50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125
```

-continued

```
Ala Leu Arg Ala Ile Ala Leu Ile Gly Tyr Ser Lys Trp Leu Ile Asn
        130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Asp Ser
        275                 280                 285

Phe Arg Ser Ile Tyr Gly Val Asn Lys Gly Ile Pro Ala Gly Ala Ala
    290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
        355                 360                 365

Ser Ser Ser Ser Thr Phe Thr Asn Ile Ile Asn Ala Val Ser Thr Tyr
    370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
        435                 440                 445

Ile Pro Ser Thr Cys Ser Gly Ala Ser Val Val Gly Ser Tyr Ser Arg
    450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
                485                 490                 495

Val Ala Val Thr Phe His Glu Leu Val Ser Thr Gln Phe Gly Gln Thr
            500                 505                 510

Val Lys Val Ala Gly Asn Ala Ala Ala Leu Gly Asn Trp Ser Thr Ser
        515                 520                 525

Ala Ala Val Ala Leu Asp Ala Val Asn Tyr Ala Asp Asn His Pro Leu
    530                 535                 540

Trp Ile Gly Thr Val Asn Leu Glu Ala Gly Asp Val Val Glu Tyr Lys
```

```
                545            550            555            560
Tyr Ile Asn Val Gly Gln Asp Gly Ser Val Thr Trp Glu Ser Asp Pro
            565                570                575
Asn His Thr Tyr Thr Val Pro Ala Val Ala Cys Val Thr Gln Val Val
        580                585                590
Lys Glu Asp Thr Trp Gln Ser
    595

<210> SEQ ID NO 5
<211> LENGTH: 2154
<212> TYPE: DNA
<213> ORGANISM: Hypocrea citrina var. americana

<400> SEQUENCE: 5
atgcacgtcc tgtcgacggc tgtgttgctc ggcttggtgg ccgttcaaaa ggttctggga      60
aggccagggc tgaatggcgt acccgacgtc acaaaacggt ccgttgacga cttcatcagc     120
aatgagtctc ctattgcact gaacaacctc ctgtgcaatg tcggccctga tggatgccgc     180
gcctttggcg catcggcagg cactgtcgct gcctcgccca gcacaaccga cccagactgt     240
aagtgtatac gagacaatcc atgagatgag gccctctacg tgtattgcac actaacacag     300
atattgacgc ggattactac atgtggacgc gagacagtgc tctcatcttc aagaccgttg     360
tcgacaggtt cacccagaac tacgatgcta gcctgcagaa gcgcattgag cagtacattg     420
ctgctcaggc cacgcttcag gggatttcca acccatcggg ctctctagca gatgggtccg     480
gtctcggcga gcccaagttc gagctgaccc tgaatcagtt caccggccac tggggccgac     540
cacagcggga cggtccagct ctgcgagcca ttgccttgat cggctattcg aagtggctca     600
tcgacaacaa ctaccagtcg actgtgtccg acatcatctg gcccattctg cggaatgatc     660
tcaactacgt agcgcagtac tggtatgtgt tgcttactgt tttgctccgt tgagaatggt     720
ccgtttctaa cctttaaaact gtaggaacca aaccggtttt gacttgtggg aggaagttga     780
aggaagctca ttctttaccg ttgctaacca gcaccgaggt acggaacacg actcaggtca     840
actgacgaga ggcgctgcta acacgcttca gcccttgt cgagggcgct acgcttgctg     900
ctatccttgg ccagtcggga agcagctatt ctgctgttgc tccccagatt ctgtgcttcc     960
tccaaaaatt tgggtgtct tccggcggat acgtgaactc caacagtgcg tctatgtgtg    1020
cgctctgtga gctctgatga agcggatgct aacagtttat ctgtaatagt caacagtgat    1080
atcaacagaa ccggaaagga tgccaactct cttctcgcct ctatccacac attcgatcct    1140
agcattggct gtgaccccgc taccttccag ccctgcagtg ataaggccct tccaacctc     1200
aagtccgtcg tcgattcatt ccgctccatc tacggcgtca accagggcat ctctgctggc    1260
tctgccgtgg ccatcggccg atactccgag gacgtctact caacggaaa ccctggtac     1320
ctggccacat tgccgccgc cgagcagctg tacgactccc tgtacgtgtg aagcagacg     1380
ggctcgatca cggtgacggc catccctctg gccttcttcc aggagctcgt gccgggcgtg    1440
gccgccggca cgtacctcag cagccagtct acgttcacca gcatcgtcaa cgccgtctca    1500
gcctacgcgg acggcttcct aaacgaggcg gccaagtacg tcccctccga tggctcgctc    1560
gccgagcagt tgacaagaa caacggcacg cctctgtcgg ccgtgcacct gacctggtcg    1620
tatgcctcct ttttgacggc gaccgcgcgt cgagctggtt ctgtgcctcc gtcgtgggcc    1680
aatagcaacg caacctcgat tccgacggcc tgctctggaa cgtcggtggt tggatcatac    1740
tcgagtccca cagccacgtc attccctccc tcccagacgc ccaaagttgg caagccaacg    1800
```

-continued

```
ggcacgccct tcacgcccat tccctgcgcc acgccaacct ccgtggccgt caccttccac    1860
gagctcccaa cgacgcagtt tggccagacc atcaaattgg ctggcagcgc tgaggccctg    1920
ggcaactgga gcaccggtgc cgccgtgggc ctcgacgccg ccaactatgc gtccaaccac    1980
ccgttgtggt ttggcacgct caacctccag gccggcgatg tcatcgagta caagtacatc    2040
aacgtgggca aggacggctc cgtgacgtgg gagagcgacc ccaaccacac gtacaccgtt    2100
cctgcggtgg cgtgtgtcac cgaggtggtc aaggaggaca cctggcagtc gtaa          2154
```

<210> SEQ ID NO 6
<211> LENGTH: 632
<212> TYPE: PRT
<213> ORGANISM: Hypocrea citrina var. americana

<400> SEQUENCE: 6

```
Met His Val Leu Ser Thr Ala Val Leu Leu Gly Leu Val Ala Val Gln
1               5                   10                  15

Lys Val Leu Gly Arg Pro Gly Leu Asn Gly Val Pro Asp Val Thr Lys
            20                  25                  30

Arg Ser Val Asp Asp Phe Ile Ser Asn Glu Ser Pro Ile Ala Leu Asn
        35                  40                  45

Asn Leu Leu Cys Asn Val Gly Pro Asp Gly Cys Arg Ala Phe Gly Ala
    50                  55                  60

Ser Ala Gly Thr Val Ala Ala Ser Pro Ser Thr Thr Asp Pro Asp Tyr
65                  70                  75                  80

Tyr Tyr Met Trp Thr Arg Asp Ser Ala Leu Ile Phe Lys Thr Val Val
                85                  90                  95

Asp Arg Phe Thr Gln Asn Tyr Asp Ala Ser Leu Gln Lys Arg Ile Glu
            100                 105                 110

Gln Tyr Ile Ala Ala Gln Ala Thr Leu Gln Gly Ile Ser Asn Pro Ser
        115                 120                 125

Gly Ser Leu Ala Asp Gly Ser Gly Leu Gly Glu Pro Lys Phe Glu Leu
    130                 135                 140

Thr Leu Asn Gln Phe Thr Gly His Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asp Asn Asn Tyr Gln Ser Thr Val Ser Asp Ile Ile Trp Pro Ile Leu
            180                 185                 190

Arg Asn Asp Leu Asn Tyr Val Ala Gln Tyr Trp Asn Gln Thr Gly Phe
        195                 200                 205

Asp Leu Trp Glu Glu Val Glu Gly Ser Ser Phe Phe Thr Val Ala Asn
    210                 215                 220

Gln His Arg Ala Leu Val Glu Gly Ala Thr Leu Ala Ala Ile Leu Gly
225                 230                 235                 240

Gln Ser Gly Ser Ser Tyr Ser Ala Val Ala Pro Gln Ile Leu Cys Phe
                245                 250                 255

Leu Gln Lys Phe Trp Val Ser Ser Gly Gly Tyr Val Asn Ser Asn Ile
            260                 265                 270

Asn Ser Asp Ile Asn Arg Thr Gly Lys Asp Ala Asn Ser Leu Leu Ala
        275                 280                 285

Ser Ile His Thr Phe Asp Pro Ser Ile Gly Cys Asp Pro Ala Thr Phe
    290                 295                 300

Gln Pro Cys Ser Asp Lys Ala Leu Ser Asn Leu Lys Ser Val Val Asp
305                 310                 315                 320
```

Ser Phe Arg Ser Ile Tyr Gly Val Asn Gln Gly Ile Ser Ala Gly Ser
            325                 330                 335

Ala Val Ala Ile Gly Arg Tyr Ser Glu Asp Val Tyr Phe Asn Gly Asn
            340                 345                 350

Pro Trp Tyr Leu Ala Thr Phe Ala Ala Glu Gln Leu Tyr Asp Ser
            355                 360                 365

Leu Tyr Val Trp Lys Gln Thr Gly Ser Ile Thr Val Thr Ala Ile Pro
        370                 375                 380

Leu Ala Phe Phe Gln Glu Leu Val Pro Gly Val Ala Ala Gly Thr Tyr
385                 390                 395                 400

Leu Ser Ser Gln Ser Thr Phe Thr Ser Ile Val Asn Ala Val Ser Ala
            405                 410                 415

Tyr Ala Asp Gly Phe Leu Asn Glu Ala Ala Lys Tyr Val Pro Ser Asp
            420                 425                 430

Gly Ser Leu Ala Glu Gln Phe Asp Lys Asn Asn Gly Thr Pro Leu Ser
            435                 440                 445

Ala Val His Leu Thr Trp Ser Tyr Ala Ser Phe Leu Thr Ala Thr Ala
            450                 455                 460

Arg Arg Ala Gly Ser Val Pro Pro Ser Trp Ala Asn Ser Asn Ala Thr
465                 470                 475                 480

Ser Ile Pro Thr Ala Cys Ser Gly Thr Ser Val Val Gly Ser Tyr Ser
            485                 490                 495

Ser Pro Thr Ala Thr Ser Phe Pro Pro Ser Gln Thr Pro Lys Val Gly
            500                 505                 510

Lys Pro Thr Gly Thr Pro Phe Thr Pro Ile Pro Cys Ala Thr Pro Thr
            515                 520                 525

Ser Val Ala Val Thr Phe His Glu Leu Pro Thr Thr Gln Phe Gly Gln
            530                 535                 540

Thr Ile Lys Leu Ala Gly Ser Ala Glu Ala Leu Gly Asn Trp Ser Thr
545                 550                 555                 560

Gly Ala Ala Val Gly Leu Asp Ala Ala Asn Tyr Ala Ser Asn His Pro
            565                 570                 575

Leu Trp Phe Gly Thr Leu Asn Leu Gln Ala Gly Asp Val Ile Glu Tyr
            580                 585                 590

Lys Tyr Ile Asn Val Gly Lys Asp Gly Ser Val Thr Trp Glu Ser Asp
            595                 600                 605

Pro Asn His Thr Tyr Thr Val Pro Ala Val Ala Cys Val Thr Glu Val
            610                 615                 620

Val Lys Glu Asp Thr Trp Gln Ser
625                 630

<210> SEQ ID NO 7
<211> LENGTH: 2152
<212> TYPE: DNA
<213> ORGANISM: Hypocrea vinosa

<400> SEQUENCE: 7
atgcacgtgc tgtcgactgc tgtgctactt ggctcagttg ccgtccaaaa ggttctggga      60
agaccaggat caaacggtct atccggcgtc acaaaacgat ctgtggatga ctttatcaac     120
acacagactc ccattgcact aaacaacctt ctttgcaatg ttggccctga tggatgccgt     180
gcctttggta catcggccgg tgccgtgatt gcatctccga gcacaactga cccagactgt     240
aagtttgact tatacgggct tatctcctga tatgtcaagt tcatatgct aacacgaggg      300

```
taattaatca gactactaca tgtggacgcg agatagtgct cttgtcttca agaacattgt    360
agaccgcttc actcagcagt atgatgccgg cctgcagcgc cgcatcgagc agtacatttc    420
tgcccaggtc actcttcagg gcatctcaaa cccctctggc tctctctcgg acgggtccgg    480
tcttggtgaa cccaagtttg agttgacctt gagccagttc actggcaact ggggtcgccc    540
gcagcgcgac ggcccagctc tccgagccat tgccttgatt ggttattcga agtggctcat    600
caacaacaac taccagtcaa cggtgtcaaa tatcatctgg cccatcgtac ggaatgacct    660
caactatgtt gcccaatact ggtaagtaca agctcgccgt cttttcgtct tgttatgact    720
aattccaaca ccttcacttt aggaaccaaa ccggtttcga cctgtgggag gaagtcaatg    780
gtagctcgtt ctttaccgtt gccaaccagc accgaggtat gtatcaacat ctcatgtgca    840
attttagtt ggaaataaac aatgctgacg agttctccag ctcttgttga gggcgccaca    900
cttgctgcta ccctcggcca gtcgggaagc acctattcct cagttgcgcc tcagatcctg    960
tgcttcctcc aaagattctg ggtgtcgggt ggatatattg actctaatag taagtctact   1020
agtaccatat gctttgatga agggcgatac taaacagctt gccatagtca ataccaacga   1080
aggcaggact ggaaaagatg ccaactctct tctcgcatct atccacacgt tcgatcctag   1140
cctcggctgt gacgcctcta ccttccagcc ttgcagtgac aaagctctct ccaacctcaa   1200
ggttgttgta gactccttcc gctccatcta cggtgtcaac aagggcattc tgctggctc    1260
tgctgtcgcc atcggcagat accccgaaga tgtgtacttt aacggaaacc cttggtacct   1320
cgccacgttc gctgctgccg agcaacttta cgactccgtc tatgtctgga agaagacagg   1380
ctccatcaca gtgacttcca cttcttcggc cttcttccag gagctcgttc ccggcgtcgc   1440
agctgggact tactccagca gccagtctac cttcacaagc atcatcaacg ccatctcgac   1500
atatgctgat ggattcctca gcgaggctgc caagtacgtc cccgctgatg gttcgctcgc   1560
cgagcagttt gatcgcaaca ccggcacacc tctgtcagcc gttcacctga cctggtctta   1620
cgcctcgttt ctcaccgccg cggcccgtcg ggctggcgtt gtccccccct cgtgggccag   1680
cagcggcgct aatacagttc cttcaagctg ctcgggagct ctgtggttg atcctactc    1740
gcgtcctaca gccacgtcat tcccaccatc gcagaccccc aagcctggcg ttccttctgg   1800
tactcccttc actcccattc cctgtgctac cccgacttcc gttgccgtca ctttccacga   1860
gcttgccaca acccagtttg gtcagactat caaggtcgct ggtagcgctc ccgagctggg   1920
caactggagc acgagcgcgg ccattgctct ggatgccgtc aactatgcca ctaaccaccc   1980
cttgtggatt ggatcggtca atctggaagc cggagatgtt atcgagtaca agtacattaa   2040
cgtgggccag gatggttccg tcacctggga gagcgatcct aaccacacct acactgttcc   2100
tgcggtggca tgtgttaccg aggtggttaa ggaggacacc tggcagtcgt aa            2152
```

<210> SEQ ID NO 8
<211> LENGTH: 631
<212> TYPE: PRT
<213> ORGANISM: Hypocrea vinosa

<400> SEQUENCE: 8

```
Met His Val Leu Ser Thr Ala Val Leu Leu Gly Ser Val Ala Val Gln
1               5                   10                  15

Lys Val Leu Gly Arg Pro Gly Ser Asn Gly Leu Ser Gly Val Thr Lys
            20                  25                  30

Arg Ser Val Asp Asp Phe Ile Asn Thr Gln Thr Pro Ile Ala Leu Asn
        35                  40                  45
```

```
Asn Leu Leu Cys Asn Val Gly Pro Asp Gly Cys Arg Ala Phe Gly Thr
 50                  55                  60

Ser Ala Gly Ala Val Ile Ala Ser Pro Ser Thr Asp Pro Asp Tyr
 65                   70                  75                  80

Tyr Tyr Met Trp Thr Arg Asp Ser Ala Leu Val Phe Lys Asn Ile Val
                 85                  90                  95

Asp Arg Phe Thr Gln Gln Tyr Asp Ala Gly Leu Gln Arg Arg Ile Glu
             100                 105                 110

Gln Tyr Ile Ser Ala Gln Val Thr Leu Gln Gly Ile Ser Asn Pro Ser
         115                 120                 125

Gly Ser Leu Ser Asp Gly Ser Gly Leu Gly Glu Pro Lys Phe Glu Leu
     130                 135                 140

Thr Leu Ser Gln Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Ile Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Asn Gly Ser Ser Phe Phe Thr Val Ala Asn
    210                 215                 220

Gln His Arg Ala Leu Val Glu Gly Ala Thr Leu Ala Ala Thr Leu Gly
225                 230                 235                 240

Gln Ser Gly Ser Thr Tyr Ser Val Ala Pro Gln Ile Leu Cys Phe
                245                 250                 255

Leu Gln Arg Phe Trp Val Ser Gly Gly Tyr Ile Asp Ser Asn Ile Asn
            260                 265                 270

Thr Asn Glu Gly Arg Thr Gly Lys Asp Ala Asn Ser Leu Leu Ala Ser
        275                 280                 285

Ile His Thr Phe Asp Pro Ser Leu Gly Cys Asp Ala Ser Thr Phe Gln
    290                 295                 300

Pro Cys Ser Asp Lys Ala Leu Ser Asn Leu Lys Val Val Val Asp Ser
305                 310                 315                 320

Phe Arg Ser Ile Tyr Gly Val Asn Lys Gly Ile Pro Ala Gly Ser Ala
                325                 330                 335

Val Ala Ile Gly Arg Tyr Pro Glu Asp Val Tyr Phe Asn Gly Asn Pro
            340                 345                 350

Trp Tyr Leu Ala Thr Phe Ala Ala Glu Gln Leu Tyr Asp Ser Val
        355                 360                 365

Tyr Val Trp Lys Lys Thr Gly Ser Ile Thr Val Thr Ser Thr Ser Ser
    370                 375                 380

Ala Phe Phe Gln Glu Leu Val Pro Gly Val Ala Ala Gly Thr Tyr Ser
385                 390                 395                 400

Ser Ser Gln Ser Thr Phe Thr Ser Ile Ile Asn Ala Ile Ser Thr Tyr
                405                 410                 415

Ala Asp Gly Phe Leu Ser Glu Ala Ala Lys Tyr Val Pro Ala Asp Gly
            420                 425                 430

Ser Leu Ala Glu Gln Phe Asp Arg Asn Thr Gly Thr Pro Leu Ser Ala
        435                 440                 445

Val His Leu Thr Trp Ser Tyr Ala Ser Phe Leu Thr Ala Ala Ala Arg
    450                 455                 460

Arg Ala Gly Val Val Pro Pro Ser Trp Ala Ser Ser Gly Ala Asn Thr
```

-continued

```
            465                 470                 475                 480
Val Pro Ser Ser Cys Ser Gly Ala Ser Val Gly Ser Tyr Ser Arg
                    485                 490                 495

Pro Thr Ala Thr Ser Phe Pro Pro Ser Gln Thr Pro Lys Pro Gly Val
                500                 505                 510

Pro Ser Gly Thr Pro Phe Thr Pro Ile Pro Cys Ala Thr Pro Thr Ser
            515                 520                 525

Val Ala Val Thr Phe His Glu Leu Ala Thr Thr Gln Phe Gly Gln Thr
        530                 535                 540

Ile Lys Val Ala Gly Ser Ala Pro Glu Leu Gly Asn Trp Ser Thr Ser
545                 550                 555                 560

Ala Ala Ile Ala Leu Asp Ala Val Asn Tyr Ala Thr Asn His Pro Leu
                565                 570                 575

Trp Ile Gly Ser Val Asn Leu Glu Ala Gly Asp Val Ile Glu Tyr Lys
                580                 585                 590

Tyr Ile Asn Val Gly Gln Asp Gly Ser Val Thr Trp Glu Ser Asp Pro
            595                 600                 605

Asn His Thr Tyr Thr Val Pro Ala Val Ala Cys Val Thr Glu Val Val
        610                 615                 620

Lys Glu Asp Thr Trp Gln Ser
625                 630

<210> SEQ ID NO 9
<211> LENGTH: 2158
<212> TYPE: DNA
<213> ORGANISM: Trichoderma sp.

<400> SEQUENCE: 9
atgcacgtcc tgtcgactgc ggtgctgctt ggctccgttg ccgttcaaaa ggtcctggga      60
agaccaggat caagcgggct atatgacgtc accaagagat ccgtcgacga cttcatcagc     120
accgaaactc ctattgcact gaacaacctt ctctgcaatg ttggtcctga tggatgtcgt     180
gcatttggca cgtcagctgg tgcggtgatt gcatctccca gcacgaccga cccagactgt     240
aagttgaaat ccagcgcta catctcacat atcgccgagc agtcgacagc gtgctaatat      300
cgagacagac tattacatgt ggacgcggga tagtgctctt gtcttcaaaa accttgtcga     360
ccgcttcacc gaagagtacg atgctggcct gcagcgccgc attgagcagt acatcactgc     420
ccaggtcact ctccagggcc tcaccaaccc atcgggttcc ctctcggacg ggtctggtct     480
gggcgagccc aagtttgagt tgaccctgca gccattcact ggcaactggg tcggccgca     540 gcgggatggc ccagctctgc gagccattgc cttgattggc tatgcgaagt ggcttatcaa     600
caacaactat cagtccactg tgtccagcgt catctggccc attgtgcgca acgacctcaa     660
ctacgttgct caatactggt tagtgacggc ttgccctcga atcacatctt gcttgtgtg     720 tctaacgtct tcacttcagg aaccaaaccg gctttgacct ctgggaggaa gtcgatggaa     780
gctcattctt cactgttgcc aaccagcacc gaggtatgaa gcaaccgtc cacactcgct      840 gttactgtat gtgaccattg ttactgacca gctctccagc acttgttgag ggtgccacgc     900
ttgttgccac gcttggccag tcgggagaca catattcatc cgttgctccc caagtcttgt     960
gcttccttca gcgattctgg gtgtcgtccg gtggatacat cgactccaac agtatgtttt    1020
gcactggtca tgaatgttga taacgacaat ggctaatcgc tctcctttag tcaacaccaa    1080
cgagggcagg actggaaagg atgccaactc gattctcact ccatccaca cctttgaccc     1140 caatcttggc tgcgatgcag gcaccttcca gccatgcagt gacaaagcgc tctccaacct    1200
```

-continued

```
caaggtcgtt gtcgactcct tccgctccat ctacagcttg aacaagggca ttcccgctgg    1260
tgctgccgtc gccattggca gatatccaga ggatgtgtac ttcaacggaa acccttggta    1320
ccttgccacg tttgctgctg ctgagcagct gtacgatgcc gtctacgtct ggaaggagac    1380
gggctccatc acggtgaccg ccacctccct ggccttcttc caggagcttg ttcccggcgt    1440
gacagctggg acctactcca gcagctcgtc gtcgaccttt accaccatca tcaacgccgt    1500
ctcgacgtac gccgatggct tcctcagcga ggctgccaag tacgtccccg ccgacggttc    1560
gctggcagag cagttcgacc gcaacaacgg cactgcgctg tccgcccgtc acctgacgtg    1620
gtcgtacgcc tccttcttga cagccacggc ccgtcgtgct ggcgtcgtgc cccttcgtg     1680 ggcaaacagc agcgccagca cgattccctc gacgtgctcc ggcgcgtccg tggtcggctc    1740
ctactcgcgt cccacagcca cgtcattccc tccgtcgcag acgcccaagc tggcgttcc     1800 gtccggcact ccctacacgc ccctgccctg cgctacccca cgtccgtgg ccgtcacctt     1860 ccacgagctc gtgtcgacac agtttggcca gacggtcaag gtcgcgggca cgctcaggc    1920 cctgggcaac tggagcacga cgccgcctgt ggctctggat gccgtcaact acgccgataa    1980
ccatcccctg tggatcggaa cggttaacct cgaggccgga gacgttgtgg agtacaagta    2040
catcaatgtc ggtcaggatg gctccgtgac ctgggagagt gaccccaacc acacttacac    2100
ggttcctgcg gtggcttgtg tgacgcaggt tgtcaaggag gacacctggc agtcgtaa      2158
```

<210> SEQ ID NO 10
<211> LENGTH: 633
<212> TYPE: PRT
<213> ORGANISM: Trichoderma sp.

<400> SEQUENCE: 10

```
Met His Val Leu Ser Thr Ala Val Leu Leu Gly Ser Val Ala Val Gln
1               5                   10                  15

Lys Val Leu Gly Arg Pro Gly Ser Ser Gly Leu Tyr Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Asp Pro Asp Tyr
65                  70                  75                  80

Tyr Tyr Met Trp Thr Arg Asp Ser Ala Leu Val Phe Lys Asn Leu Val
                85                  90                  95

Asp Arg Phe Thr Glu Glu Tyr Asp Ala Gly Leu Gln Arg Arg Ile Glu
            100                 105                 110

Gln Tyr Ile Thr Ala Gln Val Thr Leu Gln Gly Leu Thr Asn Pro Ser
        115                 120                 125

Gly Ser Leu Ser Asp Gly Ser Gly Leu Gly Glu Pro Lys Phe Glu Leu
    130                 135                 140

Thr Leu Gln Pro Phe Thr Gly Asn Trp Gly Arg Pro Gln Arg Asp Gly
145                 150                 155                 160

Pro Ala Leu Arg Ala Ile Ala Leu Ile Gly Tyr Ala Lys Trp Leu Ile
                165                 170                 175

Asn Asn Asn Tyr Gln Ser Thr Val Ser Ser Val Ile Trp Pro Ile Val
            180                 185                 190

Arg Asn Asp Leu Asn Tyr Val Ala Gln Tyr Trp Asn Gln Thr Gly Phe
        195                 200                 205
```

```
Asp Leu Trp Glu Glu Val Asp Gly Ser Ser Phe Phe Thr Val Ala Asn
    210                 215                 220

Gln His Arg Ala Leu Val Glu Gly Ala Thr Leu Val Ala Thr Leu Gly
225                 230                 235                 240

Gln Ser Gly Asp Thr Tyr Ser Val Ala Pro Gln Val Leu Cys Phe
                245                 250                 255

Leu Gln Arg Phe Trp Val Ser Ser Gly Gly Tyr Ile Asp Ser Asn Ile
                260                 265                 270

Asn Thr Asn Glu Gly Arg Thr Gly Lys Asp Ala Asn Ser Ile Leu Thr
                275                 280                 285

Ser Ile His Thr Phe Asp Pro Asn Leu Gly Cys Asp Ala Gly Thr Phe
    290                 295                 300

Gln Pro Cys Ser Asp Lys Ala Leu Ser Asn Leu Lys Val Val Val Asp
305                 310                 315                 320

Ser Phe Arg Ser Ile Tyr Ser Leu Asn Lys Gly Ile Pro Ala Gly Ala
                325                 330                 335

Ala Val Ala Ile Gly Arg Tyr Pro Glu Asp Val Tyr Phe Asn Gly Asn
                340                 345                 350

Pro Trp Tyr Leu Ala Thr Phe Ala Ala Ala Glu Gln Leu Tyr Asp Ala
                355                 360                 365

Val Tyr Val Trp Lys Glu Thr Gly Ser Ile Thr Val Thr Ala Thr Ser
    370                 375                 380

Leu Ala Phe Phe Gln Glu Leu Val Pro Gly Val Thr Ala Gly Thr Tyr
385                 390                 395                 400

Ser Ser Ser Ser Ser Ser Thr Phe Thr Thr Ile Ile Asn Ala Val Ser
                    405                 410                 415

Thr Tyr Ala Asp Gly Phe Leu Ser Glu Ala Ala Lys Tyr Val Pro Ala
                420                 425                 430

Asp Gly Ser Leu Ala Glu Gln Phe Asp Arg Asn Asn Gly Thr Ala Leu
                435                 440                 445

Ser Ala Arg His Leu Thr Trp Ser Tyr Ala Ser Phe Leu Thr Ala Thr
    450                 455                 460

Ala Arg Arg Ala Gly Val Val Pro Pro Ser Trp Ala Asn Ser Ser Ala
465                 470                 475                 480

Ser Thr Ile Pro Ser Thr Cys Ser Gly Ala Ser Val Val Gly Ser Tyr
                485                 490                 495

Ser Arg Pro Thr Ala Thr Ser Phe Pro Pro Ser Gln Thr Pro Lys Pro
                500                 505                 510

Gly Val Pro Ser Gly Thr Pro Tyr Thr Pro Leu Pro Cys Ala Thr Pro
                515                 520                 525

Thr Ser Val Ala Val Thr Phe His Glu Leu Val Ser Thr Gln Phe Gly
    530                 535                 540

Gln Thr Val Lys Val Ala Gly Ser Ala Gln Ala Leu Gly Asn Trp Ser
545                 550                 555                 560

Thr Ser Ala Ala Val Ala Leu Asp Ala Val Asn Tyr Ala Asp Asn His
                565                 570                 575

Pro Leu Trp Ile Gly Thr Val Asn Leu Glu Ala Gly Asp Val Val Glu
                580                 585                 590

Tyr Lys Tyr Ile Asn Val Gly Gln Asp Gly Ser Val Thr Trp Glu Ser
                595                 600                 605

Asp Pro Asn His Thr Tyr Thr Val Pro Ala Val Ala Cys Val Thr Gln
    610                 615                 620
```

Val Val Lys Glu Asp Thr Trp Gln Ser
625                 630

<210> SEQ ID NO 11
<211> LENGTH: 2144
<212> TYPE: DNA
<213> ORGANISM: Hypocrea gelatinosa

<400> SEQUENCE: 11

| | | |
|---|---|---:|
| atgcacgtgc tgtcgactgc tgtgctactc ggctcagttg ccgtccagaa ggtcctggga | | 60 |
| agaccaggat caaacggcct ttccggcgtc acaaaacgat ctgtggatga cttcatcaac | | 120 |
| acacagactc ccattgcgct aaacaacctc ctttgcaatg ttggccctga tggatgccgt | | 180 |
| gcctttggca catcggccgg tgctgtgatt gcatctccga gcacaactga cccagattgt | | 240 |
| aagtttgact tataccggca tattcttgag atgtcaagtt tcacatacta acacggggt | | 300 |
| aattgatcag actactacat gtggacgcga gacagtgctc ttgtcttcaa gaacattgtc | | 360 |
| gaccgtttca ctcaacagta cgatgccggc ctgcagcgcc gcatcgagca gtacatttct | | 420 |
| gcccaggtca ctctccaggg gccctcaaac ccctctggct ctctctcgga cgggtccggt | | 480 |
| cttggtgaac ccaagtttga gctgactttg agtcagttca ctggaaactg gggtcgtccg | | 540 |
| cagcgcgatg gcccagctct tcgagctatt gccttaatag ctattcgaa gtggctcatc | | 600 |
| aacaacaact accagtcaac tgtatcaagt atcatctggc ccattgtacg aaatgatctc | | 660 |
| aactatgttg cccagtactg gttagtacca actcgctgtc tcttcgtctt gtttaagact | | 720 |
| atctctaata cattcacttc aggaaccaaa ctggtttcga cctgtgggag aagtcaatg | | 780 |
| gtagctcgtt ctttactgtt gccaaccagc atcgaggtat gtatcaacaa ctcatacatt | | 840 |
| aattggaaat aaaaaatgct gacaagttcc ttagctcttg ttgagggtgc cacacttgcc | | 900 |
| gctaccctcg gccagtcagg aagcacctat tcctctgttg ctcctcaaat cctgtgcttc | | 960 |
| ctccagagat tttgggtgtc gggaggatac attgactcca acagtaagtc tatcagcact | | 1020 |
| atgcctggat gaagaccaat actaaacagc tcgttatagt caacagcaac gatggcagga | | 1080 |
| ctggcaaaga tgccaactct cttctcgcat ctatccacac cttcgatcct agcctgggct | | 1140 |
| gcgacgcctc caccttccag ccttgcagtg acaaagctct ctccaatctc aaggttgttg | | 1200 |
| tagactcctt ccgctccatc tacggcgtca caaaggtat ttctgctggc tctgctgttg | | 1260 |
| ccatcggcag atacccgaa gatgtgtact ttaacggaaa cccctggtat cttgccacgt | | 1320 |
| tcgctgctgc tgagcaactt tacgactccg tctatgtctg gaagaagaca ggctccatca | | 1380 |
| cggtgacttc cacctctttg gccttcttcc aggagcttgt ccccggtgtc gcggctggaa | | 1440 |
| cttactccag cagccagtct accttcacga gcatcgtcaa cgccgtctcg acatatgctg | | 1500 |
| atggattcct cagcgaggct gccaagtacg tccctgctga tggttcgctc gccgagcagt | | 1560 |
| tcgatcgaaa caccggaacg cctctgtcag ccgttcacct gacctggtca tacgcctcgt | | 1620 |
| ttttcaccgc tgcggcccgt cggtctggcg ttgtcccccc atcgtgggcc agcagcggcg | | 1680 |
| ctaactcaat ccctgcaacc tgctccggag cgtctgtggt tggatcctac tcgagtccta | | 1740 |
| cagccacgtc attcccacca tcgcagaccc caagcctgg cgttccttct ggtactccct | | 1800 |
| tcactcccct tccctgcgct accccgactt ccgttgccgt cactttccat gagcttgcca | | 1860 |
| caacccagtt tggccagaat atcaaggtcg ccggcagcgc tcccgagctg gcaactgga | | 1920 |
| gcacgagcgc ggccattgct ctggatgccg tcaactatgc cactaaccat ccctgtggaa | | 1980 |
| ttggatcggt caatctggaa gccggagacg tcattgagta caagtacatc aacgtgggtc | | 2040 |

-continued

```
aggatggttc cgtcacctgg gagagcgacc ccaaccacac ctacactgtt ccagcggttg    2100
cctgtgtcac tgaggtggtt aaggaggaca cctggcagtc gtaa                    2144
```

<210> SEQ ID NO 12
<211> LENGTH: 631
<212> TYPE: PRT
<213> ORGANISM: Hypocrea gelatinosa

<400> SEQUENCE: 12

| | | | | | | | | | | | | | | | |
|---|---|---|---|---|---|---|---|---|---|---|---|---|---|---|---|
| Met | His | Val | Leu | Ser | Thr | Ala | Val | Leu | Leu | Gly | Ser | Val | Ala | Val | Gln |
| 1 | | | | 5 | | | | | 10 | | | | | 15 | |
| Lys | Val | Leu | Gly | Arg | Pro | Gly | Ser | Asn | Gly | Leu | Ser | Gly | Val | Thr | Lys |
| | | | 20 | | | | | 25 | | | | | 30 | | |
| Arg | Ser | Val | Asp | Asp | Phe | Ile | Asn | Thr | Gln | Thr | Pro | Ile | Ala | Leu | Asn |
| | | 35 | | | | | 40 | | | | | 45 | | | |
| Asn | Leu | Leu | Cys | Asn | Val | Gly | Pro | Asp | Gly | Cys | Arg | Ala | Phe | Gly | Thr |
| | 50 | | | | | 55 | | | | | 60 | | | | |
| Ser | Ala | Gly | Ala | Val | Ile | Ala | Ser | Pro | Ser | Thr | Thr | Asp | Pro | Asp | Tyr |
| 65 | | | | | 70 | | | | | 75 | | | | | 80 |
| Tyr | Tyr | Met | Trp | Thr | Arg | Asp | Ser | Ala | Leu | Val | Phe | Lys | Asn | Ile | Val |
| | | | | 85 | | | | | 90 | | | | | 95 | |
| Asp | Arg | Phe | Thr | Gln | Gln | Tyr | Asp | Ala | Gly | Leu | Gln | Arg | Arg | Ile | Glu |
| | | | 100 | | | | | 105 | | | | | 110 | | |
| Gln | Tyr | Ile | Ser | Ala | Gln | Val | Thr | Leu | Gln | Gly | Pro | Ser | Asn | Pro | Ser |
| | | | 115 | | | | | 120 | | | | | 125 | | |
| Gly | Ser | Leu | Ser | Asp | Gly | Ser | Gly | Leu | Gly | Glu | Pro | Lys | Phe | Glu | Leu |
| | 130 | | | | | 135 | | | | | 140 | | | | |
| Thr | Leu | Ser | Gln | Phe | Thr | Gly | Asn | Trp | Gly | Arg | Pro | Gln | Arg | Asp | Gly |
| 145 | | | | | 150 | | | | | 155 | | | | | 160 |
| Pro | Ala | Leu | Arg | Ala | Ile | Ala | Leu | Ile | Gly | Tyr | Ser | Lys | Trp | Leu | Ile |
| | | | | 165 | | | | | 170 | | | | | 175 | |
| Asn | Asn | Asn | Tyr | Gln | Ser | Thr | Val | Ser | Ser | Ile | Ile | Trp | Pro | Ile | Val |
| | | | 180 | | | | | 185 | | | | | 190 | | |
| Arg | Asn | Asp | Leu | Asn | Tyr | Val | Ala | Gln | Tyr | Trp | Asn | Gln | Thr | Gly | Phe |
| | | | 195 | | | | | 200 | | | | | 205 | | |
| Asp | Leu | Trp | Glu | Glu | Val | Asn | Gly | Ser | Ser | Phe | Phe | Thr | Val | Ala | Asn |
| | 210 | | | | | 215 | | | | | 220 | | | | |
| Gln | His | Arg | Ala | Leu | Val | Glu | Gly | Ala | Thr | Leu | Ala | Ala | Thr | Leu | Gly |
| 225 | | | | | 230 | | | | | 235 | | | | | 240 |
| Gln | Ser | Gly | Ser | Thr | Tyr | Ser | Ser | Val | Ala | Pro | Gln | Ile | Leu | Cys | Phe |
| | | | | 245 | | | | | 250 | | | | | 255 | |
| Leu | Gln | Arg | Phe | Trp | Val | Ser | Gly | Gly | Tyr | Ile | Asp | Ser | Asn | Ile | Asn |
| | | | 260 | | | | | 265 | | | | | 270 | | |
| Ser | Asn | Asp | Gly | Arg | Thr | Gly | Lys | Asp | Ala | Asn | Ser | Leu | Leu | Ala | Ser |
| | | | 275 | | | | | 280 | | | | | 285 | | |
| Ile | His | Thr | Phe | Asp | Pro | Ser | Leu | Gly | Cys | Asp | Ala | Ser | Thr | Phe | Gln |
| | 290 | | | | | 295 | | | | | 300 | | | | |
| Pro | Cys | Ser | Asp | Lys | Ala | Leu | Ser | Asn | Leu | Lys | Val | Val | Val | Asp | Ser |
| 305 | | | | | 310 | | | | | 315 | | | | | 320 |
| Phe | Arg | Ser | Ile | Tyr | Gly | Val | Asn | Lys | Gly | Ile | Ser | Ala | Gly | Ser | Ala |
| | | | | 325 | | | | | 330 | | | | | 335 | |
| Val | Ala | Ile | Gly | Arg | Tyr | Pro | Glu | Asp | Val | Tyr | Phe | Asn | Gly | Asn | Pro |
| | | | 340 | | | | | 345 | | | | | 350 | | |
| Trp | Tyr | Leu | Ala | Thr | Phe | Ala | Ala | Ala | Glu | Gln | Leu | Tyr | Asp | Ser | Val |

```
                355                 360                 365
Tyr Val Trp Lys Lys Thr Gly Ser Ile Thr Val Thr Ser Thr Ser Leu
    370                 375                 380
Ala Phe Phe Gln Glu Leu Val Pro Gly Val Ala Ala Gly Thr Tyr Ser
385                 390                 395                 400
Ser Ser Gln Ser Thr Phe Thr Ser Ile Val Asn Ala Val Ser Thr Tyr
                405                 410                 415
Ala Asp Gly Phe Leu Ser Glu Ala Ala Lys Tyr Val Pro Ala Asp Gly
            420                 425                 430
Ser Leu Ala Glu Gln Phe Asp Arg Asn Thr Gly Thr Pro Leu Ser Ala
        435                 440                 445
Val His Leu Thr Trp Ser Tyr Ala Ser Phe Phe Thr Ala Ala Ala Arg
    450                 455                 460
Arg Ser Gly Val Val Pro Pro Ser Trp Ala Ser Ser Gly Ala Asn Ser
465                 470                 475                 480
Ile Pro Ala Thr Cys Ser Gly Ala Ser Val Val Gly Ser Tyr Ser Ser
                485                 490                 495
Pro Thr Ala Thr Ser Phe Pro Pro Ser Gln Thr Pro Lys Pro Gly Val
            500                 505                 510
Pro Ser Gly Thr Pro Phe Thr Pro Leu Pro Cys Ala Thr Pro Thr Ser
        515                 520                 525
Val Ala Val Thr Phe His Glu Leu Ala Thr Thr Gln Phe Gly Gln Asn
    530                 535                 540
Ile Lys Val Ala Gly Ser Ala Pro Glu Leu Gly Asn Trp Ser Thr Ser
545                 550                 555                 560
Ala Ala Ile Ala Leu Asp Ala Val Asn Tyr Ala Thr Asn His Pro Leu
                565                 570                 575
Trp Ile Gly Ser Val Asn Leu Glu Ala Gly Asp Val Ile Glu Tyr Lys
            580                 585                 590
Tyr Ile Asn Val Gly Gln Asp Gly Ser Val Thr Trp Glu Ser Asp Pro
        595                 600                 605
Asn His Thr Tyr Thr Val Pro Ala Val Ala Cys Val Thr Glu Val Val
    610                 615                 620
Lys Glu Asp Thr Trp Gln Ser
625                 630

<210> SEQ ID NO 13
<211> LENGTH: 2127
<212> TYPE: DNA
<213> ORGANISM: Hypocrea orientalis

<400> SEQUENCE: 13
atgcacgtcc tgtcgactgc ggtgctgctc ggctccgttg ccgttcagaa ggtcctggga      60
agaccaggat caagcggtct ttctgacgta accaagagat ccgttgacga cttcatcagc     120
accgagaccc ccattgcact gaacaacctt ctctgcaatg ttggtcctga tggatgtcgt     180
gcatttggca catcagccgg tgcggtgatt gcatctccca gcacaattga cccggactgt     240
aagttggatc aataccgttg atctatgttt accgcatact gagacggaaa cagactatta     300
catgtggacg cgagacagcg ctcttgtttt caagaacctc gtcgaccgct tcaccgaaac     360
gtacgatgct ggcctgcagc gccgcattga gcagtacatc actgcccagg tcactctcca     420
gggcctctcc aacccatcgg gatcccttac ggacgggtct ggtctgggcg agcccaagtt     480
tgagctgacc ctgcagccct tcaccggcaa ctggggtcga ccgcagcgcg atggcccagc     540
```

-continued

```
tctgcgagcc attgccttga ttggatactc caagtggctc atcaacaaca actatcagtc    600
aactgtgtcc aacgtcatct ggccgattgt gcgcaacgac ctcaactacg ttgctcaata    660
ctggttagtg acacttgccc tcgaactact gcttgcgtct aacctcttca tcgtaggaac    720
cagactggct ttgacctgtg ggaggaagtg aaaggtagct cgttctttac cattgccaac    780
cagcaccgag gtatgaagca caacgtccat actcgccgtc attactttga gcattactga    840
ccacctctcc agcacttgtc gagggtgcta ctcttgccgc tactcttggc cagtcgggaa    900
gcacttattc atctgttgct ccccagatct tgtgcttcct ccaacgattc tgggtgtcgt    960
cgggcggata tgtcgactcc aatagtatgt cttccaaggc tcgtatgatt gttaaagaca   1020
agtactaaca gctggcctct agtcaacacc aacgagggca ggactggcaa ggatgtcaac   1080
tccatcctga cctccatcca caccttggat cccaaccttg gctgtgatgc aggcaccttc   1140
cagccatgca gtgacaaggc gctctccaat ctcaaggttg ttgtcgactc cttccgctcc   1200
atctacggtg tgaacaaggg cattcctgcc ggtgctgccg tcgccattgg ccgatatgca   1260
gaggatgtct acttcaacgg taaccttgg tatcttgcca cgtttgctgc cgccgaacag   1320
ctgtacgatg ccgtctatgt ctggaagaag acgggctcca tcacggttac tgccaccctcc   1380
ctggccttct tccaggagct tgttcccggc gtggcggccg ggacctacgc cagcagctcg   1440
tcgacccttta cgaacatcat caacgccgtc tcaacatacg ccgatggctt ccttagcgag   1500
gctgccaagt acgttcccgc cgacggttcg ctggccgagc agtttgaccg caacagcggc   1560
actccgctgt ccgcccttca cctgacgtgg tcgtacgcct cgttcctgac agccacggcc   1620
cgtcgggctg gcatcgtgcc cccatcgtgg gcaaacagca gcgccagcac gattccctcg   1680
acgtgctccg gcgcgtccgt ggtcggatcc tactcgcgtc ccacagccac gtcattccct   1740
ccgtcgcaga cgcccaagcc tggcgttccc tccggtacgc cctacactcc cctgccctgc   1800
gccactccaa cgtccgtggc cgtcaccttc cacgagctcg tgtcgacgca gcttggccag   1860
acggtcaagg tcgcgggcaa cgctccggcc ctgggcaact ggagcacgag cgccgccgtg   1920
gctctcgatg ccgtcaacta tgccgacaac caccgctgt ggatcggaac ggttgacctc   1980
gaggctggag atgtcgtcga gtacaagtac atcaatgtcg gccaggatgg ctccgtgacc   2040
tgggagagtg atcccaatca cacttacacg gttcctgcgg tggcttgtgt gacgcaggtt   2100
gtcaaggagg acacctggca gtcgtaa                                       2127
```

<210> SEQ ID NO 14
<211> LENGTH: 632
<212> TYPE: PRT
<213> ORGANISM: Hypocrea orientalis

<400> SEQUENCE: 14

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Ile Asp Pro Asp Tyr
65                  70                  75                  80

Tyr Tyr Met Trp Thr Arg Asp Ser Ala Leu Val Phe Lys Asn Leu Val
                85                  90                  95

-continued

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
        115                 120                 125

Gly Ser Leu Thr Asp Gly Ser Gly Leu Gly Glu Pro Lys Phe Glu Leu
    130                 135                 140

Thr Leu Gln Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Lys Gly Ser Ser Phe Phe Thr Ile Ala Asn
    210                 215                 220

Gln His Arg Ala Leu Val Glu Gly Ala Thr Leu Ala Ala Thr Leu Gly
225                 230                 235                 240

Gln Ser Gly Ser Thr Tyr Ser Ser Val Ala Pro Gln Ile Leu Cys Phe
                245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Ile Leu Thr
        275                 280                 285

Ser Ile His Thr Leu Asp Pro Asn Leu Gly Cys Asp Ala Gly Thr Phe
    290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
                325                 330                 335

Ala Val Ala Ile Gly Arg Tyr Ala Glu Asp Val Tyr Phe Asn Gly Asn
            340                 345                 350

Pro Trp Tyr Leu Ala Thr Phe Ala Ala Ala Glu Gln Leu Tyr Asp Ala
        355                 360                 365

Val Tyr Val Trp Lys Lys Thr Gly Ser Ile Thr Val Thr Ala Thr Ser
    370                 375                 380

Leu Ala Phe Phe Gln Glu Leu Val Pro Gly Val Ala Ala Gly Thr Tyr
385                 390                 395                 400

Ala Ser Ser Ser Thr Phe Thr Asn Ile Ile Asn Ala Val Ser Thr
                405                 410                 415

Tyr Ala Asp Gly Phe Leu Ser Glu Ala Ala Lys Tyr Val Pro Ala Asp
        420                 425                 430

Gly Ser Leu Ala Glu Gln Phe Asp Arg Asn Ser Gly Thr Pro Leu Ser
    435                 440                 445

Ala Leu His Leu Thr Trp Ser Tyr Ala Ser Phe Leu Thr Ala Thr Ala
    450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
                485                 490                 495

Arg Pro Thr Ala Thr Ser Phe Pro Pro Ser Gln Thr Pro Lys Pro Gly
            500                 505                 510

-continued

```
Val Pro Ser Gly Thr Pro Tyr Thr Pro Leu Pro Cys Ala Thr Pro Thr
            515                 520                 525

Ser Val Ala Val Thr Phe His Glu Leu Val Ser Thr Gln Leu Gly Gln
        530                 535                 540

Thr Val Lys Val Ala Gly Asn Ala Pro Ala Leu Gly Asn Trp Ser Thr
545                 550                 555                 560

Ser Ala Ala Val Ala Leu Asp Ala Val Asn Tyr Ala Asp Asn His Pro
                565                 570                 575

Leu Trp Ile Gly Thr Val Asp Leu Glu Ala Gly Asp Val Val Glu Tyr
            580                 585                 590

Lys Tyr Ile Asn Val Gly Gln Asp Gly Ser Val Thr Trp Glu Ser Asp
        595                 600                 605

Pro Asn His Thr Tyr Thr Val Pro Ala Val Ala Cys Val Thr Gln Val
    610                 615                 620

Val Lys Glu Asp Thr Trp Gln Ser
625                 630
```

<210> SEQ ID NO 15
<211> LENGTH: 2139
<212> TYPE: DNA
<213> ORGANISM: Trichoderma konilangbra

<400> SEQUENCE: 15

```
atgcacgtcc tgtcgactgc ggtgctgctc ggctccgttg ccgtccagaa ggttctggga      60
agaccggggt caagcggcct ctccgacgtc accaagagat ctgtcgacga tttcatcagc     120
acccagacgc ccatcgcact gaacaacctc ctctgcaatg ttggccctga cggatgccgt     180
gcatttggca catcagctgg tgcggttatt gcatcgccca gcacaactga cccagactgt     240
aagttgggct tgtaccagta tatctacgag agttgtactg cataggtact gatatcgata     300
cagattatta catgtggacg cgagacagtg ctccttgtct tcaagaacctt gtcgaccgct     360
tcactgaaac gtacgatgcg ggcctgcagc gccgcatcga gcagtacatt gctgcccagg     420
tcactctcca gggcctcacc aatccatctg gttctctctc agacgggtct ggtcttggcg     480
agcccaagtt tgagttaacc ctgaagccct tcactggcaa ctggggtcga ccgcagcggg     540
atggcccagc tctgcgggcc attgccttga ttggctactc aaagtggctc atcaacaaca     600
actatcagtc aaccgtgtcc agcctcatct ggcctattgt gcgcaacgac ctcaactatg     660
ttgcgcagta ctggtcagtg gttgcttgct cttgttaaca cttgtgtcta acgtcttcac     720
ttcaggaacc aaaccggctt tgacctgtgg gaggaagtta atggaagctc attctttacc     780
actgccaacc agcaccgagg tatgaagccc gacggctaaa cttgccatcg ctgtatatga     840
gaattacgga ctagctctcc agcacttgtt gagggcgcca cccttgctgc cactctcagc     900
cagccggcaa gcacttattc ttctgttgct ccccaaatct tgtgcttcct ccagcgatat     960
tgggtgtcgt ccggtggata cgtcgactcc aacagtatgt ctcttcatgc tcgtgggttt    1020
tcgagaaaga caatcactaa tagcttgcgc ctagtcaaca ccaacgaggg taggactgga    1080
aaggatgcca actccattct cgctgctatc cacaccttgg atcccaatct tggccgtgat    1140
gcaggcacct tccagccatg cagcgacaaa gctctctcca acctcaaggt cgttgtcgac    1200
tccttccgct ccatctacgg cgtgaacaag ggcattcccg ctggtgctgc cgccgccgtt    1260
ggcagatatc cagaggacgt gtacttcaac ggaaacccctt ggtaccttgc aacttttgct    1320
gctgctgagc agttgtacga tgccatctac gtctggaaga agacaggctc catcacagtg    1380
actgccatct ctctggcctt cttccaggag cttgttcccg gtgtggcagc tgggacctac    1440
```

-continued

```
tccagcagcc agtcgacctt tacgaacatc atcaacgccg tgtccactta cgccgatggc    1500
ttcatcagcg aggccgccaa gtacgtcccc gccgacggtt cgctggccga gcagttcgac    1560
cgcaacaacg gcactcctct gtccgccctc cacctgacgt ggtcgtacgc ctcgttcttg    1620
acagccacgg cccgccgggc tggcatcgtg cccccctcgt gggcaaacag cagcgccagc    1680
tcgattcctt cgacatgctc cggcgcgtcc gtggtcggat cctattcacg tcccacagcc    1740
acgtcattcc ctccctcgca aacgcccaag cccggcgttc cttccggtac tccctacacg    1800
cccctgccct gcgctacccc agcgtccgtg ccgtcacct tccacgagct cgtgtcgacg    1860
cagcttggcc agacggtcaa agttgcgggc agcgccccgg ccctgggcaa ctggagcacg    1920
agcgccgctg tcgctctgga cgccgtcaac tacgccgata accatcccct gtggattggg    1980
tcggtcgaac ttgaggctgg agatgtcgtt gaatacaagt acatcaatgt gggtcaggat    2040
ggttccgtga cctgggagag tgaccccaac cacacttaca cggttcctgc ggtggcttgt    2100
gtgacgcagg tcgtcaagga ggacacctgg cagtcgtaa                          2139
```

<210> SEQ ID NO 16
<211> LENGTH: 632
<212> TYPE: PRT
<213> ORGANISM: Trichoderma konilangbra

<400> SEQUENCE: 16

```
Met His Val Leu Ser Thr Ala Val Leu Leu Gly Ser Val Ala Val Gln
 1               5                  10                  15

Lys Val Leu Gly Arg Pro Gly Ser Ser Gly Leu Ser Asp Val Thr Lys
            20                  25                  30

Arg Ser Val Asp Asp Phe Ile Ser Thr Gln Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Thr Asp Pro Asp Tyr
65                  70                  75                  80

Tyr Tyr Met Trp Thr Arg Asp Ser Ala Leu Val Phe Lys Asn Leu Val
                85                  90                  95

Asp Arg Phe Thr Glu Thr Tyr Asp Ala Gly Leu Gln Arg Arg Ile Glu
           100                 105                 110

Gln Tyr Ile Ala Ala Gln Val Thr Leu Gln Gly Leu Thr Asn Pro Ser
       115                 120                 125

Gly Ser Leu Ser Asp Gly Ser Gly Leu Gly Glu Pro Lys Phe Glu Leu
   130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Ser Leu Ile Trp Pro Ile Val
           180                 185                 190

Arg Asn Asp Leu Asn Tyr Val Ala Gln Tyr Trp Asn Gln Thr Gly Phe
       195                 200                 205

Asp Leu Trp Glu Glu Val Asn Gly Ser Ser Phe Phe Thr Thr Ala Asn
   210                 215                 220

Gln His Arg Ala Leu Val Glu Gly Ala Thr Leu Ala Ala Thr Leu Ser
225                 230                 235                 240

Gln Pro Ala Ser Thr Tyr Ser Ser Val Ala Pro Gln Ile Leu Cys Phe
```

```
                    245                 250                 255
Leu Gln Arg Tyr Trp Val Ser Ser Gly Gly Tyr Val Asp Ser Asn Ile
        260                 265                 270
Asn Thr Asn Glu Gly Arg Thr Gly Lys Asp Ala Asn Ser Ile Leu Ala
            275                 280                 285
Ala Ile His Thr Phe Asp Pro Asn Leu Gly Arg Asp Ala Gly Thr Phe
        290                 295                 300
Gln Pro Cys Ser Asp Lys Ala Leu Ser Asn Leu Lys Val Val Val Asp
305                 310                 315                 320
Ser Phe Arg Ser Ile Tyr Gly Val Asn Lys Gly Ile Pro Ala Gly Ala
                325                 330                 335
Ala Ala Ala Val Gly Arg Tyr Pro Glu Asp Val Tyr Phe Asn Gly Asn
            340                 345                 350
Pro Trp Tyr Leu Ala Thr Phe Ala Ala Glu Gln Leu Tyr Asp Ala
        355                 360                 365
Ile Tyr Val Trp Lys Lys Thr Gly Ser Ile Thr Val Thr Ala Ile Ser
    370                 375                 380
Leu Ala Phe Phe Gln Glu Leu Val Pro Gly Val Ala Ala Gly Thr Tyr
385                 390                 395                 400
Ser Ser Ser Gln Ser Thr Phe Thr Asn Ile Ile Asn Ala Val Ser Thr
                405                 410                 415
Tyr Ala Asp Gly Phe Ile Ser Glu Ala Ala Lys Tyr Val Pro Ala Asp
            420                 425                 430
Gly Ser Leu Ala Glu Gln Phe Asp Arg Asn Asn Gly Thr Pro Leu Ser
        435                 440                 445
Ala Leu His Leu Thr Trp Ser Tyr Ala Ser Phe Leu Thr Ala Thr Ala
    450                 455                 460
Arg Arg Ala Gly Ile Val Pro Pro Ser Trp Ala Asn Ser Ser Ala Ser
465                 470                 475                 480
Ser Ile Pro Ser Thr Cys Ser Gly Ala Ser Val Val Gly Ser Tyr Ser
                485                 490                 495
Arg Pro Thr Ala Thr Ser Phe Pro Pro Ser Gln Thr Pro Lys Pro Gly
            500                 505                 510
Val Pro Ser Gly Thr Pro Tyr Thr Pro Leu Pro Cys Ala Thr Pro Ala
        515                 520                 525
Ser Val Ala Val Thr Phe His Glu Leu Val Ser Thr Gln Leu Gly Gln
    530                 535                 540
Thr Val Lys Val Ala Gly Ser Pro Ala Leu Gly Asn Trp Ser Thr
545                 550                 555                 560
Ser Ala Ala Val Ala Leu Asp Ala Val Asn Tyr Ala Asp Asn His Pro
                565                 570                 575
Leu Trp Ile Gly Ser Val Glu Leu Glu Ala Gly Asp Val Val Glu Tyr
            580                 585                 590
Lys Tyr Ile Asn Val Gly Gln Asp Gly Ser Val Thr Trp Glu Ser Asp
        595                 600                 605
Pro Asn His Thr Tyr Thr Val Pro Ala Val Ala Cys Val Thr Gln Val
    610                 615                 620
Val Lys Glu Asp Thr Trp Gln Ser
625                 630

<210> SEQ ID NO 17
<211> LENGTH: 599
<212> TYPE: PRT
<213> ORGANISM: Hypocrea citrina var. americana
```

<400> SEQUENCE: 17

```
Ser Val Asp Asp Phe Ile Ser Asn Glu Ser Pro Ile Ala Leu Asn Asn
  1               5                  10                  15

Leu Leu Cys Asn Val Gly Pro Asp Gly Cys Arg Ala Phe Gly Ala Ser
             20                  25                  30

Ala Gly Thr Val Ala Ala Ser Pro Ser Thr Thr Asp Pro Asp Tyr Tyr
         35                  40                  45

Tyr Met Trp Thr Arg Asp Ser Ala Leu Ile Phe Lys Thr Val Val Asp
 50                  55                  60

Arg Phe Thr Gln Asn Tyr Asp Ala Ser Leu Gln Lys Arg Ile Glu Gln
 65                  70                  75                  80

Tyr Ile Ala Ala Gln Ala Thr Leu Gln Gly Ile Ser Asn Pro Ser Gly
                 85                  90                  95

Ser Leu Ala Asp Gly Ser Gly Leu Gly Glu Pro Lys Phe Glu Leu Thr
            100                 105                 110

Leu Asn Gln Phe Thr Gly His Trp Gly Arg Pro Gln Arg Asp Gly Pro
            115                 120                 125

Ala Leu Arg Ala Ile Ala Leu Ile Gly Tyr Ser Lys Trp Leu Ile Asp
        130                 135                 140

Asn Asn Tyr Gln Ser Thr Val Ser Asp Ile Ile Trp Pro Ile Leu Arg
145                 150                 155                 160

Asn Asp Leu Asn Tyr Val Ala Gln Tyr Trp Asn Gln Thr Gly Phe Asp
                165                 170                 175

Leu Trp Glu Glu Val Glu Gly Ser Ser Phe Phe Thr Val Ala Asn Gln
            180                 185                 190

His Arg Ala Leu Val Glu Gly Ala Thr Leu Ala Ala Ile Leu Gly Gln
        195                 200                 205

Ser Gly Ser Ser Tyr Ser Ala Val Ala Pro Gln Ile Leu Cys Phe Leu
    210                 215                 220

Gln Lys Phe Trp Val Ser Ser Gly Gly Tyr Val Asn Ser Asn Ile Asn
225                 230                 235                 240

Ser Asp Ile Asn Arg Thr Gly Lys Asp Ala Asn Ser Leu Leu Ala Ser
                245                 250                 255

Ile His Thr Phe Asp Pro Ser Ile Gly Cys Asp Pro Ala Thr Phe Gln
            260                 265                 270

Pro Cys Ser Asp Lys Ala Leu Ser Asn Leu Lys Ser Val Val Asp Ser
        275                 280                 285

Phe Arg Ser Ile Tyr Gly Val Asn Gln Gly Ile Ser Ala Gly Ser Ala
    290                 295                 300

Val Ala Ile Gly Arg Tyr Ser Glu Asp Val Tyr Phe Asn Gly Asn Pro
305                 310                 315                 320

Trp Tyr Leu Ala Thr Phe Ala Ala Ala Glu Gln Leu Tyr Asp Ser Leu
                325                 330                 335

Tyr Val Trp Lys Gln Thr Gly Ser Ile Thr Val Thr Ala Ile Pro Leu
            340                 345                 350

Ala Phe Phe Gln Glu Leu Val Pro Gly Val Ala Ala Gly Thr Tyr Leu
        355                 360                 365

Ser Ser Gln Ser Thr Phe Thr Ser Ile Val Asn Ala Val Ser Ala Tyr
    370                 375                 380

Ala Asp Gly Phe Leu Asn Glu Ala Ala Lys Tyr Val Pro Ser Asp Gly
385                 390                 395                 400

Ser Leu Ala Glu Gln Phe Asp Lys Asn Asn Gly Thr Pro Leu Ser Ala
```

-continued

Val His Leu Thr Trp Ser Tyr Ala Ser Phe Leu Thr Ala Thr Ala Arg
            405                 410                 415
Arg Ala Gly Ser Val Pro Pro Ser Trp Ala Asn Ser Asn Ala Thr Ser
        420                 425                 430
Ile Pro Thr Ala Cys Ser Gly Thr Ser Val Val Gly Ser Tyr Ser Ser
    435                 440                 445
Pro Thr Ala Thr Ser Phe Pro Pro Ser Gln Thr Pro Lys Val Gly Lys
450                 455                 460
Pro Thr Gly Thr Pro Phe Thr Pro Ile Pro Cys Ala Thr Pro Thr Ser
465                 470                 475                 480
Val Ala Val Thr Phe His Glu Leu Pro Thr Thr Gln Phe Gly Gln Thr
            485                 490                 495
Ile Lys Leu Ala Gly Ser Ala Glu Ala Leu Gly Asn Trp Ser Thr Gly
        500                 505                 510
Ala Ala Val Gly Leu Asp Ala Ala Asn Tyr Ala Ser Asn His Pro Leu
    515                 520                 525
Trp Phe Gly Thr Leu Asn Leu Gln Ala Gly Asp Val Ile Glu Tyr Lys
530                 535                 540
Tyr Ile Asn Val Gly Lys Asp Gly Ser Val Thr Trp Glu Ser Asp Pro
545                 550                 555                 560
Asn His Thr Tyr Thr Val Pro Ala Val Ala Cys Val Thr Glu Val Val
            565                 570                 575
Lys Glu Asp Thr Trp Gln Ser
        580                 585                 590

595

<210> SEQ ID NO 18
<211> LENGTH: 598
<212> TYPE: PRT
<213> ORGANISM: Hypocrea vinosa

<400> SEQUENCE: 18

Ser Val Asp Asp Phe Ile Asn Thr Gln Thr Pro Ile Ala Leu Asn Asn
1               5                   10                  15
Leu Leu Cys Asn Val Gly Pro Asp Gly Cys Arg Ala Phe Gly Thr Ser
            20                  25                  30
Ala Gly Ala Val Ile Ala Ser Pro Ser Thr Thr Asp Pro Asp Tyr Tyr
        35                  40                  45
Tyr Met Trp Thr Arg Asp Ser Ala Leu Val Phe Lys Asn Ile Val Asp
    50                  55                  60
Arg Phe Thr Gln Gln Tyr Asp Ala Gly Leu Gln Arg Ile Glu Gln
65                  70                  75                  80
Tyr Ile Ser Ala Gln Val Thr Leu Gln Gly Ile Ser Asn Pro Ser Gly
            85                  90                  95
Ser Leu Ser Asp Gly Ser Gly Leu Gly Glu Pro Lys Phe Glu Leu Thr
        100                 105                 110
Leu Ser Gln Phe Thr Gly Asn Trp Gly Arg Pro Gln Arg Asp Gly Pro
    115                 120                 125
Ala Leu Arg Ala Ile Ala Leu Ile Gly Tyr Ser Lys Trp Leu Ile Asn
130                 135                 140
Asn Asn Tyr Gln Ser Thr Val Ser Asn Ile Ile Trp Pro Ile Val Arg
145                 150                 155                 160
Asn Asp Leu Asn Tyr Val Ala Gln Tyr Trp Asn Gln Thr Gly Phe Asp
            165                 170                 175

-continued

```
Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Thr Tyr Ser Val Ala Pro Gln Ile Leu Cys Phe Leu
    210                 215                 220

Gln Arg Phe Trp Val Ser Gly Gly Tyr Ile Asp Ser Asn Ile Asn Thr
225                 230                 235                 240

Asn Glu Gly Arg Thr Gly Lys Asp Ala Asn Ser Leu Leu Ala Ser Ile
                245                 250                 255

His Thr Phe Asp Pro Ser Leu Gly Cys Asp Ala Ser Thr Phe Gln Pro
            260                 265                 270

Cys Ser Asp Lys Ala Leu Ser Asn Leu Lys Val Val Asp Ser Phe
        275                 280                 285

Arg Ser Ile Tyr Gly Val Asn Lys Gly Ile Pro Ala Gly Ser Ala Val
    290                 295                 300

Ala Ile Gly Arg Tyr Pro Glu Asp Val Tyr Phe Asn Gly Asn Pro Trp
305                 310                 315                 320

Tyr Leu Ala Thr Phe Ala Ala Ala Glu Gln Leu Tyr Asp Ser Val Tyr
                325                 330                 335

Val Trp Lys Lys Thr Gly Ser Ile Thr Val Thr Ser Thr Ser Ser Ala
            340                 345                 350

Phe Phe Gln Glu Leu Val Pro Gly Val Ala Ala Gly Thr Tyr Ser Ser
        355                 360                 365

Ser Gln Ser Thr Phe Thr Ser Ile Ile Asn Ala Ile Ser Thr Tyr Ala
    370                 375                 380

Asp Gly Phe Leu Ser Glu Ala Ala Lys Tyr Val Pro Ala Asp Gly Ser
385                 390                 395                 400

Leu Ala Glu Gln Phe Asp Arg Asn Thr Gly Thr Pro Leu Ser Ala Val
                405                 410                 415

His Leu Thr Trp Ser Tyr Ala Ser Phe Leu Thr Ala Ala Ala Arg Arg
            420                 425                 430

Ala Gly Val Val Pro Pro Ser Trp Ala Ser Ser Gly Ala Asn Thr Val
        435                 440                 445

Pro Ser Ser Cys Ser Gly Ala Ser Val Val Gly Ser Tyr Ser Arg Pro
    450                 455                 460

Thr Ala Thr Ser Phe Pro Pro Ser Gln Thr Pro Lys Pro Gly Val Pro
465                 470                 475                 480

Ser Gly Thr Pro Phe Thr Pro Ile Pro Cys Ala Thr Pro Thr Ser Val
                485                 490                 495

Ala Val Thr Phe His Glu Leu Ala Thr Thr Gln Phe Gly Gln Thr Ile
            500                 505                 510

Lys Val Ala Gly Ser Ala Pro Glu Leu Gly Asn Trp Ser Thr Ser Ala
        515                 520                 525

Ala Ile Ala Leu Asp Ala Val Asn Tyr Ala Thr Asn His Pro Leu Trp
    530                 535                 540

Ile Gly Ser Val Asn Leu Glu Ala Gly Asp Val Ile Glu Tyr Lys Tyr
545                 550                 555                 560

Ile Asn Val Gly Gln Asp Gly Ser Val Thr Trp Glu Ser Asp Pro Asn
                565                 570                 575

His Thr Tyr Thr Val Pro Ala Val Ala Cys Val Thr Glu Val Val Lys
            580                 585                 590

Glu Asp Thr Trp Gln Ser
```

-continued

595

<210> SEQ ID NO 19
<211> LENGTH: 600
<212> TYPE: PRT
<213> ORGANISM: Trichoderma sp.

<400> SEQUENCE: 19

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Thr Asp Pro Asp Tyr Tyr
        35                  40                  45

Tyr Met Trp Thr Arg Asp Ser Ala Leu Val Phe Lys Asn Leu Val Asp
    50                  55                  60

Arg Phe Thr Glu Glu Tyr Asp Ala Gly Leu Gln Arg Arg Ile Glu Gln
65                  70                  75                  80

Tyr Ile Thr Ala Gln Val Thr Leu Gln Gly Leu Thr Asn Pro Ser Gly
                85                  90                  95

Ser Leu Ser Asp Gly Ser Gly Leu Gly Glu Pro Lys Phe Glu Leu Thr
            100                 105                 110

Leu Gln Pro Phe Thr Gly Asn Trp Gly Arg Pro Gln Arg Asp Gly Pro
        115                 120                 125

Ala Leu Arg Ala Ile Ala Leu Ile Gly Tyr Ala Lys Trp Leu Ile Asn
    130                 135                 140

Asn Asn Tyr Gln Ser Thr Val Ser Ser Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asp Gly Ser Ser Phe Phe Thr Val Ala Asn Gln
            180                 185                 190

His Arg Ala Leu Val Glu Gly Ala Thr Leu Val Ala Thr Leu Gly Gln
        195                 200                 205

Ser Gly Asp Thr Tyr Ser Ser Val Ala Pro Gln Val Leu Cys Phe Leu
    210                 215                 220

Gln Arg Phe Trp Val Ser Ser Gly Gly Tyr Ile Asp Ser Asn Ile Asn
225                 230                 235                 240

Thr Asn Glu Gly Arg Thr Gly Lys Asp Ala Asn Ser Ile Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Asp Ser
    275                 280                 285

Phe Arg Ser Ile Tyr Ser Leu Asn Lys Gly Ile Pro Ala Gly Ala Ala
    290                 295                 300

Val Ala Ile Gly Arg Tyr Pro Glu Asp Val Tyr Phe Asn Gly Asn Pro
305                 310                 315                 320

Trp Tyr Leu Ala Thr Phe Ala Ala Ala Glu Gln Leu Tyr Asp Ala Val
                325                 330                 335

Tyr Val Trp Lys Glu Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
        355                 360                 365

```
Ser Ser Ser Ser Ser Thr Phe Thr Thr Ile Ile Asn Ala Val Ser Thr
    370                 375                 380
Tyr Ala Asp Gly Phe Leu Ser Glu Ala Ala Lys Tyr Val Pro Ala Asp
385                 390                 395                 400
Gly Ser Leu Ala Glu Gln Phe Asp Arg Asn Asn Gly Thr Ala Leu Ser
                405                 410                 415
Ala Arg His Leu Thr Trp Ser Tyr Ala Ser Phe Leu Thr Ala Thr Ala
            420                 425                 430
Arg Arg Ala Gly Val Val Pro Pro Ser Trp Ala Asn Ser Ser Ala Ser
    435                 440                 445
Thr Ile Pro Ser Thr Cys Ser Gly Ala Ser Val Val Gly Ser Tyr Ser
    450                 455                 460
Arg Pro Thr Ala Thr Ser Phe Pro Pro Ser Gln Thr Pro Lys Pro Gly
465                 470                 475                 480
Val Pro Ser Gly Thr Pro Tyr Thr Pro Leu Pro Cys Ala Thr Pro Thr
                485                 490                 495
Ser Val Ala Val Thr Phe His Glu Leu Val Ser Thr Gln Phe Gly Gln
            500                 505                 510
Thr Val Lys Val Ala Gly Ser Ala Gln Ala Leu Gly Asn Trp Ser Thr
    515                 520                 525
Ser Ala Ala Val Ala Leu Asp Ala Val Asn Tyr Ala Asp Asn His Pro
    530                 535                 540
Leu Trp Ile Gly Thr Val Asn Leu Glu Ala Gly Asp Val Val Glu Tyr
545                 550                 555                 560
Lys Tyr Ile Asn Val Gly Gln Asp Gly Ser Val Thr Trp Glu Ser Asp
                565                 570                 575
Pro Asn His Thr Tyr Thr Val Pro Ala Val Ala Cys Val Thr Gln Val
            580                 585                 590
Val Lys Glu Asp Thr Trp Gln Ser
    595                 600

<210> SEQ ID NO 20
<211> LENGTH: 598
<212> TYPE: PRT
<213> ORGANISM: Hypocrea gelatinosa

<400> SEQUENCE: 20

Ser Val Asp Asp Phe Ile Asn Thr Gln Thr Pro Ile Ala Leu Asn Asn
1               5                   10                  15
Leu Leu Cys Asn Val Gly Pro Asp Gly Cys Arg Ala Phe Gly Thr Ser
                20                  25                  30
Ala Gly Ala Val Ile Ala Ser Pro Ser Thr Thr Asp Pro Asp Tyr Tyr
            35                  40                  45
Tyr Met Trp Thr Arg Asp Ser Ala Leu Val Phe Lys Asn Ile Val Asp
    50                  55                  60
Arg Phe Thr Gln Gln Tyr Asp Ala Gly Leu Gln Arg Ile Glu Gln
65                  70                  75                  80
Tyr Ile Ser Ala Gln Val Thr Leu Gln Gly Pro Ser Asn Pro Ser Gly
                85                  90                  95
Ser Leu Ser Asp Gly Ser Gly Leu Gly Glu Pro Lys Phe Glu Leu Thr
            100                 105                 110
Leu Ser Gln Phe Thr Gly Asn Trp Gly Arg Pro Gln Arg Asp Gly Pro
    115                 120                 125
Ala Leu Arg Ala Ile Ala Leu Ile Gly Tyr Ser Lys Trp Leu Ile Asn
    130                 135                 140
```

```
Asn Asn Tyr Gln Ser Thr Val Ser Ser Ile Ile Trp Pro Ile Val Arg
145                 150                 155                 160

Asn Asp Leu Asn Tyr Val Ala Gln Tyr Trp Asn Gln Thr Gly Phe Asp
            165                 170                 175

Leu Trp Glu Glu Val Asn Gly Ser Ser Phe Phe Thr Val Ala Asn Gln
        180                 185                 190

His Arg Ala Leu Val Glu Gly Ala Thr Leu Ala Ala Thr Leu Gly Gln
    195                 200                 205

Ser Gly Ser Thr Tyr Ser Ser Val Ala Pro Gln Ile Leu Cys Phe Leu
210                 215                 220

Gln Arg Phe Trp Val Ser Gly Tyr Ile Asp Ser Asn Ile Asn Ser
225                 230                 235                 240

Asn Asp Gly Arg Thr Gly Lys Asp Ala Asn Ser Leu Leu Ala Ser Ile
                245                 250                 255

His Thr Phe Asp Pro Ser Leu Gly Cys Asp Ala Ser Thr Phe Gln Pro
            260                 265                 270

Cys Ser Asp Lys Ala Leu Ser Asn Leu Lys Val Val Asp Ser Phe
275                 280                 285

Arg Ser Ile Tyr Gly Val Asn Lys Gly Ile Ser Ala Gly Ser Ala Val
        290                 295                 300

Ala Ile Gly Arg Tyr Pro Glu Asp Val Tyr Phe Asn Gly Asn Pro Trp
305                 310                 315                 320

Tyr Leu Ala Thr Phe Ala Ala Ala Glu Gln Leu Tyr Asp Ser Val Tyr
                325                 330                 335

Val Trp Lys Lys Thr Gly Ser Ile Thr Val Thr Ser Thr Ser Leu Ala
            340                 345                 350

Phe Phe Gln Glu Leu Val Pro Gly Val Ala Ala Gly Thr Tyr Ser Ser
        355                 360                 365

Ser Gln Ser Thr Phe Thr Ser Ile Val Asn Ala Val Ser Thr Tyr Ala
    370                 375                 380

Asp Gly Phe Leu Ser Glu Ala Ala Lys Tyr Val Pro Ala Asp Gly Ser
385                 390                 395                 400

Leu Ala Glu Gln Phe Asp Arg Asn Thr Gly Thr Pro Leu Ser Ala Val
                405                 410                 415

His Leu Thr Trp Ser Tyr Ala Ser Phe Phe Thr Ala Ala Ala Arg Arg
            420                 425                 430

Ser Gly Val Val Pro Pro Ser Trp Ala Ser Ser Gly Ala Asn Ser Ile
        435                 440                 445

Pro Ala Thr Cys Ser Gly Ala Ser Val Val Gly Ser Tyr Ser Ser Pro
    450                 455                 460

Thr Ala Thr Ser Phe Pro Pro Ser Gln Thr Pro Lys Pro Gly Val Pro
465                 470                 475                 480

Ser Gly Thr Pro Phe Thr Pro Leu Pro Cys Ala Thr Pro Thr Ser Val
                485                 490                 495

Ala Val Thr Phe His Glu Leu Ala Thr Thr Gln Phe Gly Gln Asn Ile
            500                 505                 510

Lys Val Ala Gly Ser Ala Pro Glu Leu Gly Asn Trp Ser Thr Ser Ala
        515                 520                 525

Ala Ile Ala Leu Asp Ala Val Asn Tyr Ala Thr Asn His Pro Leu Trp
    530                 535                 540

Ile Gly Ser Val Asn Leu Glu Ala Gly Asp Val Ile Glu Tyr Lys Tyr
545                 550                 555                 560
```

```
Ile Asn Val Gly Gln Asp Gly Ser Val Thr Trp Glu Ser Asp Pro Asn
            565                 570                 575

His Thr Tyr Thr Val Pro Ala Val Ala Cys Val Thr Glu Val Val Lys
            580                 585                 590

Glu Asp Thr Trp Gln Ser
            595

<210> SEQ ID NO 21
<211> LENGTH: 599
<212> TYPE: PRT
<213> ORGANISM: Hypocrea orientalis

<400> SEQUENCE: 21

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Ile Asp Pro Asp Tyr Tyr
            35                  40                  45

Tyr Met Trp Thr Arg Asp Ser Ala Leu Val Phe Lys Asn Leu Val Asp
50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Thr Asp Gly Ser Gly Leu Gly Glu Pro Lys Phe Glu Leu Thr
            100                 105                 110

Leu Gln Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Lys Gly Ser Ser Phe Phe Thr Ile Ala Asn Gln
            180                 185                 190

His Arg Ala Leu Val Glu Gly Ala Thr Leu Ala Ala Thr Leu Gly Gln
        195                 200                 205

Ser Gly Ser Thr Tyr Ser Ser Val Ala Pro Gln Ile Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Ile Leu Thr Ser
                245                 250                 255

Ile His Thr Leu Asp Pro Asn Leu Gly Cys Asp Ala Gly Thr Phe Gln
            260                 265                 270

Pro Cys Ser Asp Lys Ala Leu Ser Asn Leu Lys Val Val Val Asp Ser
        275                 280                 285

Phe Arg Ser Ile Tyr Gly Val Asn Lys Gly Ile Pro Ala Gly Ala Ala
    290                 295                 300

Val Ala Ile Gly Arg Tyr Ala Glu Asp Val Tyr Phe Asn Gly Asn Pro
305                 310                 315                 320

Trp Tyr Leu Ala Thr Phe Ala Ala Ala Glu Gln Leu Tyr Asp Ala Val
                325                 330                 335
```

```
Tyr Val Trp Lys Lys Thr Gly Ser Ile Thr Val Thr Ala Thr Ser Leu
                340                 345                 350

Ala Phe Phe Gln Glu Leu Val Pro Gly Val Ala Gly Thr Tyr Ala
            355                 360                 365

Ser Ser Ser Ser Thr Phe Thr Asn Ile Ile Asn Ala Val Ser Thr Tyr
370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
            435                 440                 445

Ile Pro Ser Thr Cys Ser Gly Ala Ser Val Val Gly Ser Tyr Ser Arg
450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
                485                 490                 495

Val Ala Val Thr Phe His Glu Leu Val Ser Thr Gln Leu Gly Gln Thr
            500                 505                 510

Val Lys Val Ala Gly Asn Ala Pro Ala Leu Gly Asn Trp Ser Thr Ser
            515                 520                 525

Ala Ala Val Ala Leu Asp Ala Val Asn Tyr Ala Asp Asn His Pro Leu
530                 535                 540

Trp Ile Gly Thr Val Asp Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
            580                 585                 590

Lys Glu Asp Thr Trp Gln Ser
            595

<210> SEQ ID NO 22
<211> LENGTH: 599
<212> TYPE: PRT
<213> ORGANISM: Trichoderma konilangbra

<400> SEQUENCE: 22

Ser Val Asp Asp Phe Ile Ser Thr Gln Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Thr Thr Asp Pro Asp Tyr Tyr
            35                  40                  45

Tyr Met Trp Thr Arg Asp Ser Ala Leu Val Phe Lys Asn Leu Val Asp
50                  55                  60

Arg Phe Thr Glu Thr Tyr Asp Ala Gly Leu Gln Arg Arg Ile Glu Gln
65                  70                  75                  80

Tyr Ile Ala Ala Gln Val Thr Leu Gln Gly Leu Thr Asn Pro Ser Gly
                85                  90                  95

Ser Leu Ser Asp Gly Ser Gly Leu Gly Glu Pro Lys Phe Glu Leu Thr
```

-continued

```
                100                 105                 110
Leu Lys Pro Phe Thr Gly Asn Trp Gly Arg Pro Gln Arg Asp Gly Pro
            115                 120                 125
Ala Leu Arg Ala Ile Ala Leu Ile Gly Tyr Ser Lys Trp Leu Ile Asn
        130                 135                 140
Asn Asn Tyr Gln Ser Thr Val Ser Ser Leu Ile Trp Pro Ile Val Arg
145                 150                 155                 160
Asn Asp Leu Asn Tyr Val Ala Gln Tyr Trp Asn Gln Thr Gly Phe Asp
                165                 170                 175
Leu Trp Glu Glu Val Asn Gly Ser Ser Phe Phe Thr Thr Ala Asn Gln
            180                 185                 190
His Arg Ala Leu Val Glu Gly Ala Thr Leu Ala Ala Thr Leu Ser Gln
        195                 200                 205
Pro Ala Ser Thr Tyr Ser Ser Val Ala Pro Gln Ile Leu Cys Phe Leu
    210                 215                 220
Gln Arg Tyr Trp Val Ser Ser Gly Gly Tyr Val Asp Ser Asn Ile Asn
225                 230                 235                 240
Thr Asn Glu Gly Arg Thr Gly Lys Asp Ala Asn Ser Ile Leu Ala Ala
                245                 250                 255
Ile His Thr Phe Asp Pro Asn Leu Gly Arg Asp Ala Gly Thr Phe Gln
            260                 265                 270
Pro Cys Ser Asp Lys Ala Leu Ser Asn Leu Lys Val Val Asp Ser
        275                 280                 285
Phe Arg Ser Ile Tyr Gly Val Asn Lys Gly Ile Pro Ala Gly Ala Ala
    290                 295                 300
Ala Ala Val Gly Arg Tyr Pro Glu Asp Val Tyr Phe Asn Gly Asn Pro
305                 310                 315                 320
Trp Tyr Leu Ala Thr Phe Ala Ala Glu Gln Leu Tyr Asp Ala Ile
                325                 330                 335
Tyr Val Trp Lys Lys Thr Gly Ser Ile Thr Val Thr Ala Ile Ser Leu
            340                 345                 350
Ala Phe Phe Gln Glu Leu Val Pro Gly Val Ala Ala Gly Thr Tyr Ser
        355                 360                 365
Ser Ser Gln Ser Thr Phe Thr Asn Ile Ile Asn Ala Val Ser Thr Tyr
    370                 375                 380
Ala Asp Gly Phe Ile Ser Glu Ala Ala Lys Tyr Val Pro Ala Asp Gly
385                 390                 395                 400
Ser Leu Ala Glu Gln Phe Asp Arg Asn Asn Gly Thr Pro Leu Ser Ala
                405                 410                 415
Leu His Leu Thr Trp Ser Tyr Ala Ser Phe Leu Thr Ala Thr Ala Arg
            420                 425                 430
Arg Ala Gly Ile Val Pro Pro Ser Trp Ala Asn Ser Ser Ala Ser Ser
        435                 440                 445
Ile Pro Ser Thr Cys Ser Gly Ala Ser Val Val Gly Ser Tyr Ser Arg
    450                 455                 460
Pro Thr Ala Thr Ser Phe Pro Ser Gln Thr Pro Lys Pro Gly Val
465                 470                 475                 480
Pro Ser Gly Thr Pro Tyr Thr Pro Leu Pro Cys Ala Thr Pro Ala Ser
                485                 490                 495
Val Ala Val Thr Phe His Glu Leu Val Ser Thr Gln Leu Gly Gln Thr
            500                 505                 510
Val Lys Val Ala Gly Ser Ala Pro Ala Leu Gly Asn Trp Ser Thr Ser
        515                 520                 525
```

```
Ala Ala Val Ala Leu Asp Ala Val Asn Tyr Ala Asp Asn His Pro Leu
        530                 535                 540

Trp Ile Gly Ser Val Glu Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
            580                 585                 590

Lys Glu Asp Thr Trp Gln Ser
        595

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
atgcccgcct cgccatgga cc                                              22

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
ttacgactgc caggtgtcct cc                                             22

<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
atgcacgtcc tgtcgactgc gg                                             22

<210> SEQ ID NO 26
<211> LENGTH: 640
<212> TYPE: PRT
<213> ORGANISM: Aspergillus niger

<400> SEQUENCE: 26

Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
```

-continued

```
            100                 105                 110
Gln Gly Ile Ser Asn Pro Ser Gly Asp Leu Ser Ser Gly Ala Gly Leu
            115                 120                 125

Gly Glu Pro Lys Phe Asn Val Asp Glu Thr Ala Tyr Thr Gly Ser Trp
        130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
        210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
        290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
370                 375                 380

Gly Thr Tyr Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
        450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Thr Ser Thr Ser Thr
        515                 520                 525
```

```
Ser Ser Thr Ser Cys Thr Thr Pro Thr Ala Val Ala Val Thr Phe Asp
        530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Asp Pro Leu Trp Tyr Val Thr Val Thr
            580                 585                 590

Leu Pro Ala Gly Glu Ser Phe Glu Tyr Lys Phe Ile Arg Ile Glu Ser
            595                 600                 605

Asp Asp Ser Val Glu Trp Glu Ser Asp Pro Asn Arg Glu Tyr Thr Val
        610                 615                 620

Pro Gln Ala Cys Gly Thr Ser Thr Ala Thr Val Thr Asp Thr Trp Arg
625                 630                 635                 640

<210> SEQ ID NO 27
<211> LENGTH: 640
<212> TYPE: PRT
<213> ORGANISM: Aspergillus kawachi

<400> SEQUENCE: 27

Met Arg Val Ser Thr Ser Ser Ile Ala Leu Ala Val Ser Leu Phe Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asn Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ser Asp
                85                  90                  95

Gly Glu Ala Tyr His Gly Tyr Trp Gln Gln Lys Ile Tyr Asn Val Asn
            100                 105                 110

Ser Asn Phe Gly Thr Ala Asp Asp Leu Lys Ser Leu Ser Asp Ala Leu
        115                 120                 125

His Ala Arg Gly Met Tyr Leu Met Val Asp Val Val Pro Asn His Met
    130                 135                 140

Gly Tyr Ala Gly Asn Gly Asn Asp Val Asp Tyr Ser Val Phe Asp Pro
145                 150                 155                 160

Phe Asp Ser Ser Tyr Phe His Pro Tyr Cys Leu Ile Thr Asp Trp
                165                 170                 175

Asp Asn Leu Thr Met Val Gln Asp Cys Trp Glu Gly Asp Thr Ile Val
            180                 185                 190

Ser Leu Pro Asp Leu Asn Thr Thr Glu Thr Ala Val Arg Thr Ile Trp
        195                 200                 205

Tyr Asp Trp Val Ala Asp Leu Val Ser Asn Tyr Ser Val Asp Gly Leu
    210                 215                 220

Arg Ile Asp Ser Val Glu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
                245                 250                 255

Pro Ala Leu Asp Cys Pro Tyr Gln Lys Tyr Leu Asp Gly Val Leu Asn
```

```
                260                 265                 270
Tyr Pro Ile Tyr Trp Gln Leu Leu Tyr Ala Phe Glu Ser Ser Ser Gly
            275                 280                 285
Ser Ile Ser Asn Leu Tyr Asn Met Ile Lys Ser Val Ala Ser Asp Cys
        290                 295                 300
Ser Asp Pro Thr Leu Leu Gly Asn Phe Ile Glu Asn His Asp Asn Pro
305                 310                 315                 320
Arg Phe Ala Ser Tyr Thr Ser Asp Tyr Ser Gln Ala Lys Asn Val Leu
                325                 330                 335
Ser Tyr Ile Phe Leu Ser Asp Gly Ile Pro Ile Val Tyr Ala Gly Glu
            340                 345                 350
Glu Gln His Tyr Ser Gly Gly Asp Val Pro Tyr Asn Arg Glu Ala Thr
        355                 360                 365
Trp Leu Ser Gly Tyr Asp Thr Ser Ala Glu Leu Tyr Thr Trp Ile Ala
370                 375                 380
Thr Thr Asn Ala Ile Arg Lys Leu Ala Ile Ser Ala Asp Ser Asp Tyr
385                 390                 395                 400
Ile Thr Tyr Ala Asn Asp Pro Ile Tyr Thr Asp Ser Asn Thr Ile Ala
                405                 410                 415
Met Arg Lys Gly Thr Ser Gly Ser Gln Ile Ile Thr Val Leu Ser Asn
            420                 425                 430
Lys Gly Ser Ser Gly Ser Ser Tyr Thr Leu Thr Leu Ser Gly Ser Gly
        435                 440                 445
Tyr Thr Ser Gly Thr Lys Leu Ile Glu Ala Tyr Thr Cys Thr Ser Val
    450                 455                 460
Thr Val Asp Ser Asn Gly Asp Ile Pro Val Pro Met Ala Ser Gly Leu
465                 470                 475                 480
Pro Arg Val Leu Leu Pro Ala Ser Val Val Asp Ser Ser Leu Cys
                485                 490                 495
Gly Gly Ser Gly Asn Thr Thr Thr Thr Thr Ala Ala Thr Ser Thr
            500                 505                 510
Ser Lys Ala Thr Thr Ser Ser Ser Ser Ser Ala Ala Ala Thr Thr
        515                 520                 525
Ser Ser Ser Cys Thr Ala Thr Ser Thr Thr Leu Pro Ile Thr Phe Glu
    530                 535                 540
Glu Leu Val Thr Thr Thr Tyr Gly Glu Glu Val Tyr Leu Ser Gly Ser
545                 550                 555                 560
Ile Ser Gln Leu Gly Glu Trp Asp Thr Ser Asp Ala Val Lys Leu Ser
                565                 570                 575
Ala Asp Asp Tyr Thr Ser Ser Asn Pro Glu Trp Ser Val Thr Val Ser
            580                 585                 590
Leu Pro Val Gly Thr Thr Phe Glu Tyr Lys Phe Ile Lys Val Asp Glu
        595                 600                 605
Gly Gly Ser Val Thr Trp Glu Ser Asp Pro Asn Arg Glu Tyr Thr Val
    610                 615                 620
Pro Glu Cys Gly Ser Gly Ser Gly Glu Thr Val Val Asp Thr Trp Arg
625                 630                 635                 640

<210> SEQ ID NO 28
<211> LENGTH: 2088
<212> TYPE: DNA
<213> ORGANISM: Trichoderma sp.

<400> SEQUENCE: 28
```

```
atgcatgtct tgtcaacggc cgtcctgctc ggctcggttg ccgtccaaaa ggtcctggga    60
agacctggcg catccgacat tacaaaacga gccgttactg acttcatcaa ctcggaaact   120
cccattgccc tgaacaatct gatttgcaat gttggtcctg acggatgccg tgcttttggc   180
acatcgatcg gcgctgtagt tgcgtcgcca agcacaactg acccagactg taagctagtt   240
tttgcattat acttccacta tcgtatatac aatctatata tacagtgcgc taacacgaat   300
ctaaacaaag acttttacat gtggactcga atagtgctc ttgttttcaa gacgcttgtt   360
gatcggttca cacagaacta cgatgcaggc ctgcagcgcc gcatcgagca gtacattgct   420
gctcaggtca ctcttcaggg catctcaaac ccatctggtt ccctctcaga cgggtctggc   480
cttggcgagc ccaagttcga gcttaccttg agccagttca ctggcaactg ggccgcccg   540
cagcgtgatg gtccagctct tcgagccatt gccttgattg ctattcaaa gtggctcatt   600
agcaacaact accagtcgac agtgtcgaac atcatttggc ccattgtgcg aaatgatctc   660
aactacgttg cccagtactg gtcagtgatt gcttgttttc ttgcccgcta ttcactggtt   720
ctttgctaac cttgactttt aggaaccaaa ctggatttga cctgtgggag gaggtcaacg   780
gcagctcatt cttcgctgta gccaaccagc accgagcact tgttgagggt gctacccttg   840
ccactactct tggccagtcg ggaagcagct attccactgt tgctcctcag attctctgct   900
tccttcaaaa gttctggtcg ccatccggat atgtcatctc caacagtaag ctatcaatgc   960
agaccaattt tgtagatgaa tgcgtatgct aacactagtc ggcgcagtca acagcaacga  1020
cggcaggact ggaaaggatt ccaactccat tcttacatct attcacactt tcgatcccag  1080
cattggctgc gatgccgcca ctttccagcc ttgcagtgac aaggctcttt caaacctcaa  1140
ggtctacgtc gactccttcc gctccatcta tggcgtcaac tcgggcattc ctgctggcac  1200
tgctgttgcc gttggtagat acccagagga cgtctacttt aacggaaacc cctggtatct  1260
ttctaccttt gctgttgctg agcagctgta cgacgccctg tatgtctgga agaagactgg  1320
ctccatcacc gtcacttcca cctctctggc ttcttccaag agctcgtccc cagcgtgaca  1380
gccggaacct acgccagcag ctcgtctacc ttcaccagca tcgtcaacgc cgtatccacc  1440
tacgccgatg gattcgtcag cgaggcggcc aagtacgtcc cctctgatgg ttctctctcc  1500
gagcagttcg acaagaacac cggcactcct ctctccgccg ttcacctgac ctggtcgtat  1560
gcctccttcc tgactgccac gacccgtcgc gctggcattg tccctccttc atggattagc  1620
agcggcgcca acaccgttcc ctcgtcctgc tccggcacga cagtggctgg ttcctactca  1680
agtcccacag ccacgtcatt ccctccgtca cagactccca agactgcggc tactggtacc  1740
agcttcactc ccattgcctg cgctacccca acttccgtgg ctgtgacctt ccacgagctt  1800
gctacgaccg tccccggcca gacaatcaag gtcgttggca atgcccaggc cctgggcaac  1860
tggagcacca cgcgccggtgt tgccctgaac gccgtcaact gtgcttccaa ccaccctctg  1920
tggatcggac ccgtcaatct caaggccgga gacgtcgtcg agtacaagta tatcaacgtg  1980
ggctcagacg gctccgtgac ttgggaggcc gaccccaacc acacttacac tgtccctgca  2040
gtggcctgtg ttaccgcagt tgttaaggag gacacctggc agtcgtaa             2088
```

<210> SEQ ID NO 29
<211> LENGTH: 627
<212> TYPE: PRT
<213> ORGANISM: Trichoderma sp.

<400> SEQUENCE: 29

Met His Val Leu Ser Thr Ala Val Leu Leu Gly Ser Val Ala Val Gln

-continued

```
1               5                   10                  15
Lys Val Leu Gly Arg Pro Gly Ala Ser Asp Ile Thr Lys Arg Ala Val
                20                  25                  30

Thr Asp Phe Ile Asn Ser Glu Thr Pro Ile Ala Leu Asn Asn Leu Ile
            35                  40                  45

Cys Asn Val Gly Pro Asp Gly Cys Arg Ala Phe Gly Thr Ser Ile Gly
        50                  55                  60

Ala Val Val Ala Ser Pro Ser Thr Thr Asp Pro Asp Tyr Phe Tyr Met
65                  70                  75                  80

Trp Thr Arg Asp Ser Ala Leu Val Phe Lys Thr Leu Val Asp Arg Phe
                85                  90                  95

Thr Gln Lys Tyr Asp Ala Gly Leu Gln Arg Arg Ile Glu Gln Tyr Ile
            100                 105                 110

Ala Ala Gln Val Thr Leu Gln Gly Ile Ser Asn Pro Ser Gly Ser Leu
        115                 120                 125

Ser Asp Gly Ser Gly Leu Gly Glu Pro Lys Phe Glu Leu Thr Leu Ser
130                 135                 140

Gln Phe Thr Gly Asn Trp Gly Arg Pro Gln Arg Asp Gly Pro Ala Leu
145                 150                 155                 160

Arg Ala Ile Ala Leu Ile Gly Tyr Ser Lys Trp Leu Ile Ser Asn Asn
                165                 170                 175

Tyr Gln Ser Thr Val Ser Asn Ile Ile Trp Pro Ile Val Arg Asn Asp
            180                 185                 190

Leu Asn Tyr Val Ala Gln Tyr Trp Asn Gln Thr Gly Phe Asp Leu Trp
        195                 200                 205

Glu Glu Val Asn Gly Ser Ser Phe Phe Ala Val Ala Asn Gln His Arg
210                 215                 220

Ala Leu Val Glu Gly Ala Thr Leu Ala Thr Thr Leu Gly Gln Ser Gly
225                 230                 235                 240

Ser Ser Tyr Ser Thr Val Ala Pro Gln Ile Leu Cys Phe Leu Gln Lys
                245                 250                 255

Phe Trp Ser Pro Ser Gly Tyr Val Ile Ser Asn Ile Asn Ser Asn Asp
            260                 265                 270

Gly Arg Thr Gly Lys Asp Ser Asn Ser Ile Leu Thr Ser Ile His Thr
        275                 280                 285

Phe Asp Pro Ser Ile Gly Cys Asp Ala Ala Thr Phe Gln Pro Cys Ser
290                 295                 300

Asp Lys Ala Leu Ser Asn Leu Lys Val Tyr Val Asp Ser Phe Arg Ser
305                 310                 315                 320

Ile Tyr Gly Val Asn Ser Gly Ile Pro Ala Gly Thr Ala Val Ala Val
                325                 330                 335

Gly Arg Tyr Pro Glu Asp Val Tyr Phe Asn Gly Asn Pro Trp Tyr Leu
            340                 345                 350

Ser Thr Phe Ala Val Ala Glu Gln Leu Tyr Asp Ala Leu Tyr Val Trp
        355                 360                 365

Lys Lys Thr Gly Ser Ile Thr Val Thr Ser Ser Leu Ala Phe Phe
370                 375                 380

Gln Glu Leu Val Pro Ser Val Thr Ala Gly Thr Tyr Ala Ser Ser Ser
385                 390                 395                 400

Ser Thr Phe Thr Ser Ile Val Asn Ala Val Ser Thr Tyr Ala Asp Gly
                405                 410                 415

Phe Val Ser Glu Ala Ala Lys Tyr Val Pro Ser Asp Gly Ser Leu Ser
            420                 425                 430
```

-continued

```
Glu Gln Phe Asp Lys Asn Thr Gly Thr Pro Leu Ser Ala Val His Leu
        435                 440                 445
Thr Trp Ser Tyr Ala Ser Phe Leu Thr Ala Thr Thr Arg Arg Ala Gly
    450                 455                 460
Ile Val Pro Pro Ser Trp Ile Ser Ser Gly Ala Asn Thr Val Pro Ser
465                 470                 475                 480
Ser Cys Ser Gly Thr Thr Val Ala Gly Ser Tyr Ser Ser Pro Thr Ala
                485                 490                 495
Thr Ser Phe Pro Pro Ser Gln Thr Pro Lys Thr Ala Ala Thr Gly Thr
            500                 505                 510
Ser Phe Thr Pro Ile Ala Cys Ala Thr Pro Thr Ser Val Ala Val Thr
        515                 520                 525
Phe His Glu Leu Ala Thr Thr Val Pro Gly Gln Thr Ile Lys Val Val
    530                 535                 540
Gly Asn Ala Gln Ala Leu Gly Asn Trp Ser Thr Ser Ala Gly Val Ala
545                 550                 555                 560
Leu Asn Ala Val Asn Cys Ala Ser Asn His Pro Leu Trp Ile Gly Pro
                565                 570                 575
Val Asn Leu Lys Ala Gly Asp Val Val Glu Tyr Lys Tyr Ile Asn Val
            580                 585                 590
Gly Ser Asp Gly Ser Val Thr Trp Glu Ala Asp Pro Asn His Thr Tyr
        595                 600                 605
Thr Val Pro Ala Val Ala Cys Val Thr Ala Val Val Lys Glu Asp Thr
    610                 615                 620
Trp Gln Ser
625
```

<210> SEQ ID NO 30
<211> LENGTH: 2141
<212> TYPE: DNA
<213> ORGANISM: Trichoderma harzianum

<400> SEQUENCE: 30

```
atgcatgtgc tgtcgactgc tgtgctgctt ggctcagttg ccgtccaaaa ggttctggga      60
aggccaggat cgaacggcct gtccggcgtc acaaaacgat ccgtggatga ctccatcaac     120
acacagactc ccattgcact aaacaacctc ctttgcaatg ttggccctga tgggtgccgt     180
gcctttggta tcggccgg tgctgtgatt gcatctccga gcacaactga cccagactgt      240
aagtttgact tatagcggca tattcctgac atgtcaaatt tcacatacta atacgagggt     300
aattgatcag actactacat gtggacgcga cagtgctc ttgtcttcaa gaacattgta      360
gaccgcttca ctgagcagta tgatgctggc tgcagcgcc gcatcgagca gtatatttct     420
gcccaggtca ctcttcaggg gatctcaaac ccctctggtt ctctctcgga tgggtctggt     480
cttggtgaac ccaagtttga gttgaccttg agccagttca ctggcaactg gggtcgcccg     540
cagcgcgatg gcccagctct ccgagccatt gccttgattg ctattcaaa gtggctcatc     600
aacaacaact accagtcaac ggtgtcaaac atcatctggc ccattgtgcg aatgatctc      660
aactatgttg cccagtactg gttagtacaa gctcgctgtc tcttcgtctt gtttatgact     720
aattctaaca ccttcacctt aggaatcaaa ccggtttcga cctgtgggag gaagtcaatg     780
gtagttcgtt cttaccgtt gccaaccagc accgaggtat gtatcaatat ctcatgtgtt     840
tttagttgtc aatgctgacg agtccccag ctcttgttga gggcgccaca cttgccgcta     900
ccctcggcca gtcgggaagc accattcct ctgttgctcc tcagatcctg tgcttcctcc     960
```

-continued

```
aaagattctg ggtgtcgggt ggatacattg actccaacag taagtacacc agcaccacat    1020
gctttgatga agagcgatac taaacagctt gtcatagtca acaccaacga gggcaggact    1080
ggaaaagatg ccaactctct tctcgcatct atccacacgt tcgatcccag ccttggctgt    1140
gacgcctcta ccttccagcc ttgcagtgac aaggctctct ccaacctcaa ggttgttgtg    1200
gactccttcc gctccatcta cagtgtcaac aagggcattc ccgctggcgc tgctgttgcc    1260
gtcggcagat accccgaaga cgtgtacttt aacggaaacc cctggtatct cgccacgttc    1320
gctgctgccg agcaattgta cgactccgtc tatgtctgga agaagacagg ctccatcacg    1380
gtgacttcca cttctttggc cttcttccag gagctcgttc ccggcgtcgc ggctggaact    1440
tactccagca gccagtctac ctttacgagc atcatcaacg ccgtctcgac atatgctgat    1500
ggattcctca gcgaggctgc caagtacgtc cccgctgatg gttcgctcgc cgagcagttc    1560
gatcgcaaca ccggcacgcc tctgtcagcc gttcacctga cctggtcgta cgcctcgttt    1620
ctcaccgccg cggcccgtcg ggctggcgtt gtgcccccct cgtgggccag cagcggcgct    1680
aactcagtcc cttcaagctg ctcgggagct tctgtggttg gatcctactc gcgtcctaca    1740
gccacgtcat tcccaccgtc gcagacccccc aagcctggcg ctccttctgg tgctcccttc    1800
actcccattc cctgtgctac cccggcctcc gttgccgtta ccttccacga gcttgccaca    1860
acccaatttg gccagacaat caaggtcgct ggtagcgccc ccgagctggg caactggagc    1920
acgagcgcgg ccattgctct ggatgccgtc aactatgcca ctaaccatcc cctgtggatt    1980
ggatcggtca atctggaggc cggagacgtc atcgagtaca agtacatcag cgtgggccag    2040
gatggttccg tcacctggga gagcgacccc aaccacacct acactgttcc tgcggtggcc    2100
tgtgtcaccg aggtggttaa ggaggacacc tggcagtcgt a                        2141
```

<210> SEQ ID NO 31
<211> LENGTH: 631
<212> TYPE: PRT
<213> ORGANISM: Trichoderma harzianum

<400> SEQUENCE: 31

```
Met His Val Leu Ser Thr Ala Val Leu Leu Gly Ser Val Ala Val Gln
1               5                   10                  15

Lys Val Leu Gly Arg Pro Gly Ser Asn Gly Leu Ser Gly Val Thr Lys
            20                  25                  30

Arg Ser Val Asp Asp Ser Ile Asn Thr Gln Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Thr Asp Pro Asp Tyr
65                  70                  75                  80

Tyr Tyr Met Trp Thr Arg Asp Ser Ala Leu Val Phe Lys Asn Ile Val
                85                  90                  95

Asp Arg Phe Thr Glu Gln Tyr Asp Ala Gly Leu Gln Arg Arg Ile Glu
            100                 105                 110

Gln Tyr Ile Ser Ala Gln Val Thr Leu Gln Gly Ile Ser Asn Pro Ser
        115                 120                 125

Gly Ser Leu Ser Asp Gly Ser Gly Leu Gly Glu Pro Lys Phe Glu Leu
    130                 135                 140

Thr Leu Ser Gln Phe Thr Gly Asn Trp Gly Arg Pro Gln Arg Asp Gly
145                 150                 155                 160
```

```
Pro Ala Leu Arg Ala Ile Ala Leu Ile Gly Tyr Ser Lys Trp Leu Ile
            165                 170                 175

Asn Asn Asn Tyr Gln Ser Thr Val Ser Asn Ile Ile Trp Pro Ile Val
            180                 185                 190

Arg Asn Asp Leu Asn Tyr Val Ala Gln Tyr Trp Asn Gln Thr Gly Phe
            195                 200                 205

Asp Leu Trp Glu Glu Val Asn Gly Ser Ser Phe Phe Thr Val Ala Asn
            210                 215                 220

Gln His Arg Ala Leu Val Glu Gly Ala Thr Leu Ala Ala Thr Leu Gly
225                 230                 235                 240

Gln Ser Gly Ser Thr Tyr Ser Ser Val Ala Pro Gln Ile Leu Cys Phe
                245                 250                 255

Leu Gln Arg Phe Trp Val Ser Gly Gly Tyr Ile Asp Ser Asn Ile Asn
                260                 265                 270

Thr Asn Glu Gly Arg Thr Gly Lys Asp Ala Asn Ser Leu Leu Ala Ser
                275                 280                 285

Ile His Thr Phe Asp Pro Ser Leu Gly Cys Asp Ala Ser Thr Phe Gln
                290                 295                 300

Pro Cys Ser Asp Lys Ala Leu Ser Asn Leu Lys Val Val Val Asp Ser
305                 310                 315                 320

Phe Arg Ser Ile Tyr Ser Val Asn Lys Gly Ile Pro Ala Gly Ala Ala
                325                 330                 335

Val Ala Val Gly Arg Tyr Pro Glu Asp Val Tyr Phe Asn Gly Asn Pro
                340                 345                 350

Trp Tyr Leu Ala Thr Phe Ala Ala Glu Gln Leu Tyr Asp Ser Val
                355                 360                 365

Tyr Val Trp Lys Lys Thr Gly Ser Ile Thr Val Thr Ser Thr Ser Leu
            370                 375                 380

Ala Phe Phe Gln Glu Leu Val Pro Gly Val Ala Ala Gly Thr Tyr Ser
385                 390                 395                 400

Ser Ser Gln Ser Thr Phe Thr Ser Ile Ile Asn Ala Val Ser Thr Tyr
                405                 410                 415

Ala Asp Gly Phe Leu Ser Glu Ala Lys Tyr Val Pro Ala Asp Gly
                420                 425                 430

Ser Leu Ala Glu Gln Phe Asp Arg Asn Thr Gly Thr Pro Leu Ser Ala
            435                 440                 445

Val His Leu Thr Trp Ser Tyr Ala Ser Phe Leu Thr Ala Ala Ala Arg
            450                 455                 460

Arg Ala Gly Val Val Pro Pro Ser Trp Ala Ser Ser Gly Ala Asn Ser
465                 470                 475                 480

Val Pro Ser Ser Cys Ser Gly Ala Ser Val Val Gly Ser Tyr Ser Arg
                485                 490                 495

Pro Thr Ala Thr Ser Phe Pro Pro Ser Gln Thr Pro Lys Pro Gly Ala
                500                 505                 510

Pro Ser Gly Ala Pro Phe Thr Pro Ile Pro Cys Ala Thr Pro Ala Ser
                515                 520                 525

Val Ala Val Thr Phe His Glu Leu Ala Thr Thr Gln Phe Gly Gln Thr
                530                 535                 540

Ile Lys Val Ala Gly Ser Ala Pro Glu Leu Gly Asn Trp Ser Thr Ser
545                 550                 555                 560

Ala Ala Ile Ala Leu Asp Ala Val Asn Tyr Ala Thr Asn His Pro Leu
                565                 570                 575

Trp Ile Gly Ser Val Asn Leu Glu Ala Gly Asp Val Ile Glu Tyr Lys
```

```
            580                 585                 590
Tyr Ile Ser Val Gly Gln Asp Gly Ser Val Thr Trp Glu Ser Asp Pro
        595                 600                 605

Asn His Thr Tyr Thr Val Pro Ala Val Ala Cys Val Thr Glu Val Val
        610                 615                 620

Lys Glu Asp Thr Trp Gln Ser
625                 630

<210> SEQ ID NO 32
<211> LENGTH: 2131
<212> TYPE: DNA
<213> ORGANISM: Trichoderma longibrachiatum

<400> SEQUENCE: 32
```

| | | | | | |
|---|---|---|---|---|---|
| atgcacgtcc | tgtcgactgc | ggtgctgctc | ggttccgttg | ccgttcagaa | ggtcctggga | 60 |
| aggccaggat | caagcggtct | atctgacgta | accaagagat | ctgttgacga | cttcatcagc | 120 |
| accgagactc | ctattgcact | gaacaacctt | ctctgcaatg | ttggtcctga | tggatgtcgt | 180 |
| gcatttggca | catcagctgg | tgcggtgatt | gcatctccca | gcacaattga | cccggactgt | 240 |
| aagtgtatca | ataccgttga | tctatgttta | tcgcatgctg | agacggggac | agactattac | 300 |
| atgtggacgc | gagacagcgc | tcttgtcttc | aagaacctcg | tcgaccgctt | caccgaaacg | 360 |
| tacgatgctg | gcctgcagcg | ccgcattgag | cagtacatca | ctgcccaggt | cactctccag | 420 |
| ggcctctcca | acccatcggg | ttcccttacg | gacggatctg | gcctgggcga | gcccaagttt | 480 |
| gagctgaccc | tgaagccatt | caccggcaac | tgggtcgac | cgcagcgcga | cggcccagct | 540 |
| ctgcgagccg | ttgccttgat | tggatactcc | aagtggctca | tcaacaacaa | ctatcagtca | 600 |
| actgtgtcca | acgtcatctg | gccgattgtg | cgcaacgacc | tcaactacgt | tgctcagtac | 660 |
| tggttagtga | ttacttgctc | ttgaattact | gcttgcatct | gacctctta | tcgtaggaac | 720 |
| cagacyggct | tgacctgtg | ggaggaagtg | aatggaagct | cgttctttac | catggccaac | 780 |
| cagcaccgag | gtatgaagca | aacgtctat | actcgccgtc | attacatgtg | agcattactg | 840 |
| accggctatc | cagcacttgt | cgagggtgct | actcttgctg | ccactcttgg | ccagtcggga | 900 |
| agcacttatt | catctgttgc | tccccagatc | ttgtgcttcc | tccaacgatt | ctgggtgtcg | 960 |
| tcgggcggat | atgtcgactc | caacagtatg | tcttccacgg | ctcgtatgat | gttgacaat | 1020 |
| gacaagtact | aacagctcgc | ttctagtcaa | caccaacgag | ggcaggactg | caaggatgt | 1080 |
| caactccgtt | ctgacttcca | tccacacctt | tgatcccaac | cttggctgtg | atgcagccac | 1140 |
| cttccagcca | tgcagtgaca | aggcgctctc | caatctcaag | gttgttgtcg | actccttccg | 1200 |
| ctccatctac | ggcgtgaaca | agggcattcc | tgccggtgct | gccgtcgcca | ttggccgata | 1260 |
| tgcagaggat | gtgtacttca | acggtaaccc | ttggtatctt | gccacgtttg | ctgccgccga | 1320 |
| acagctgtac | gatgccatct | atgtctggaa | gaagacgggc | tctatcacgg | ttactgccac | 1380 |
| ctccctggcc | ttcttccagg | agcttgttcc | cggcgtggcg | gccgggacct | acgccagcag | 1440 |
| ctcgtcgacc | tttacgaaca | tcatcaacgc | cgtctcgaca | tacgccgatg | gcttcctcag | 1500 |
| cgaggcagcc | aagtacgttc | cgccgacgg | ttcgctggcc | gagcagtttg | accgcaacag | 1560 |
| cggcactccg | ctgtccgccc | ttcacctgac | gtggtcgtac | gcctcgttcc | tgacagccac | 1620 |
| ggcccgtcgg | gctggcatcg | tgcccccctc | gtgggcaaac | agcagcgcca | gcacgatccc | 1680 |
| ctccacgtgc | tccggcgcgt | ccgtggtcgg | atcctactcg | cgtcccacag | ccacgtcatt | 1740 |
| ccctccgtcg | cagacgccca | agcctggcgt | tccctccggt | acgccctaca | ctcccctgcc | 1800 |

-continued

```
ctgcgccacc ccaacgtccg tggccgtcac cttccacgag ctcgtgtcga cacagtttgg    1860
ccagacggtc aaggtcgcgg gcaacgctcc ggccctcggc aactggagcg caagcgccgc    1920
cgtggctctc gatgccatca actatgccga caaccacccg ctgtggatcg aacggtcga    1980 cctcgaggct ggggatgtcg tcgagtacaa gtacatcaat gtcggccagg atggctccgt    2040
gacctgggag agtgacccca accacactta cacggttcct gcggtggcct gtgtgacgca    2100
ggttgtcaag gaggacacct ggcagtcgta a                                   2131
```

<210> SEQ ID NO 33
<211> LENGTH: 632
<212> TYPE: PRT
<213> ORGANISM: Trichoderma longibrachiatum

<400> SEQUENCE: 33

```
Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Ile Asp Pro Asp Tyr
65                  70                  75                  80

Tyr Tyr Met Trp Thr Arg Asp Ser Ala Leu Val Phe Lys Asn Leu Val
                85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
        115                 120                 125

Gly Ser Leu Thr Asp Gly Ser Gly Leu Gly Glu Pro Lys Phe Glu Leu
    130                 135                 140

Thr Leu Lys Pro Phe Thr Gly Asn Trp Gly Arg Pro Gln Arg Asp Gly
145                 150                 155                 160

Pro Ala Leu Arg Ala Val Ala Leu Ile Gly Tyr Ser Lys Trp Leu Ile
                165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Asn Gly Ser Ser Phe Phe Thr Met Ala Asn
    210                 215                 220

Gln His Arg Ala Leu Val Glu Gly Ala Thr Leu Ala Ala Thr Leu Gly
225                 230                 235                 240

Gln Ser Gly Ser Thr Tyr Ser Ser Val Ala Pro Gln Ile Leu Cys Phe
                245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Val Leu Thr
        275                 280                 285

Ser Ile His Thr Phe Asp Pro Asn Leu Gly Cys Asp Ala Ala Thr Phe
    290                 295                 300

Gln Pro Cys Ser Asp Lys Ala Leu Ser Asn Leu Lys Val Val Val Asp
305                 310                 315                 320
```

Ser Phe Arg Ser Ile Tyr Gly Val Asn Lys Gly Ile Pro Ala Gly Ala
            325                 330                 335

Ala Val Ala Ile Gly Arg Tyr Ala Glu Asp Val Tyr Phe Asn Gly Asn
            340                 345                 350

Pro Trp Tyr Leu Ala Thr Phe Ala Ala Glu Gln Leu Tyr Asp Ala
            355                 360                 365

Ile Tyr Val Trp Lys Lys Thr Gly Ser Ile Thr Val Thr Ala Thr Ser
        370                 375                 380

Leu Ala Phe Phe Gln Glu Leu Val Pro Gly Val Ala Ala Gly Thr Tyr
385                 390                 395                 400

Ala Ser Ser Ser Ser Thr Phe Thr Asn Ile Ile Asn Ala Val Ser Thr
            405                 410                 415

Tyr Ala Asp Gly Phe Leu Ser Glu Ala Ala Lys Tyr Val Pro Ala Asp
            420                 425                 430

Gly Ser Leu Ala Glu Gln Phe Asp Arg Asn Ser Gly Thr Pro Leu Ser
            435                 440                 445

Ala Leu His Leu Thr Trp Ser Tyr Ala Ser Phe Leu Thr Ala Thr Ala
        450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
            485                 490                 495

Arg Pro Thr Ala Thr Ser Phe Pro Pro Ser Gln Thr Pro Lys Pro Gly
            500                 505                 510

Val Pro Ser Gly Thr Pro Tyr Thr Pro Leu Pro Cys Ala Thr Pro Thr
            515                 520                 525

Ser Val Ala Val Thr Phe His Glu Leu Val Ser Thr Gln Phe Gly Gln
        530                 535                 540

Thr Val Lys Val Ala Gly Asn Ala Pro Ala Leu Gly Asn Trp Ser Ala
545                 550                 555                 560

Ser Ala Ala Val Ala Leu Asp Ala Ile Asn Tyr Ala Asp Asn His Pro
            565                 570                 575

Leu Trp Ile Gly Thr Val Asp Leu Glu Ala Gly Asp Val Val Glu Tyr
            580                 585                 590

Lys Tyr Ile Asn Val Gly Gln Asp Gly Ser Val Thr Trp Glu Ser Asp
        595                 600                 605

Pro Asn His Thr Tyr Thr Val Pro Ala Val Ala Cys Val Thr Gln Val
        610                 615                 620

Val Lys Glu Asp Thr Trp Gln Ser
625                 630

<210> SEQ ID NO 34
<211> LENGTH: 2151
<212> TYPE: DNA
<213> ORGANISM: Trichoderma asperellum

<400> SEQUENCE: 34
atgcacgtcc tgtcgactgc ggtgctactt ggctcagttg ccgtccaaaa ggttctggga      60
agaccaggat caaacggcct gtccggcgtc acaaaacgat ctgtggatga ctttatcaac     120
acacagactc ccattgcttt aaacaacctt ctttgcaatg ttggcccctga tggatgccgt     180 gcctttggta tcggccgg tgctgtgatt gcatctccga gcacaactga cccagactgt      240
aagtttgacc tatactggca tattcctgat atgtcaaagt tcatatacta acacgagggt     300

```
aattaatcag actactacat gtggacgcga gatagtgctc ttgtcttcaa gaacattgtc    360
gaccgcttca ctcagcagta tgatgccggc ctgcagcgcc gcatcgagca gtacatttct    420
gcccaggtca ctcttcaggg catctcaaac ccctctggct ctctctcgga cggatccggt    480
cttggtgaac ccaagtttga gttgaccttg agccagttca ctggcaactg gggtcgcccg    540
cagcgcgatg gcccagctct ccgagccatt gccttgattg ttattcgaa gtggctcatc     600
aacaacaact accagtcaac ggtgtcaaat atcatctggc ccattgtgcg gaatgacctc    660
aactatgttg ctcaatactg gttagtacaa gctcgctgtc ttttcgttcg tttatgattg    720
attctaacat cttcacttca ggaaccaaac cggattcgat ctgtgggagg aagttaatgg    780
tagctcgttc tttaccgttg ccaaccagca ccgaggtatg tatcaacatc tcatgtgcaa    840
ttttagttg gaaataaaca atactgacga gttctccagc tcttgttgag ggcgccacac     900
ttgctgccac cctcggccag tcgggaagca cctattcctc agttgcgcct cagatcctgt    960
gcttcctcca gaggttctgg gtgtcgggtg gatacattga ctccaacagt aagtccacca   1020
gcaccatatg ctttgatgaa gggcgatact aaacagcttg ctatagtcaa caccaacgag   1080
ggcaggactg gaaaagatgc caactctctt ctcgcatcta ccacacgtt cgatcctagc    1140
cttggctgtg acgcctccac cttccagcct tgcagtgaca aagccctctc caacctcaag   1200
gtcgttgtag actccttccg ctccatctac ggtgtcaaca agggcattcc cgctggctct   1260
gctgtcgcca tcggcagata ccccgaagac gtgtacttta acggaaaccc ctggtatctc   1320
gctacgttcg ctgctgccga gcaactttac gactccgtct atgtctggaa gaagacaggc   1380
tccatcacgg tgacttccac ttctttggcc ttcttccagg agctcgttcc cggcgtcgcg   1440
gctggaactt actccagcag ccagtctacc ttcacgagca tcatcaacgc cgtctcgaca   1500
tatgctgatg gattcctcag cgaggctgcc aagtacgtcc ccgctgatgg ttcgctcgcc   1560
gagcagttcg atcgcaacac cggcacacct ctgtcagccg ttcacctgac ctggtcgtac   1620
gcctcgtttc tcaccgccgc ggcccgtcgg gctggcgttg tcccccctc atgggccagc    1680
agcggcgcta actcagttcc ttcaagctgc tcgggagctt ctgtggttgg atcctactcg   1740
cgtcctacag ccacgtcatt cccaccatcg cagaccccca agcctggcgt tccttctggt   1800
actcccttca ctcccattcc ctgtgctacc ccgacttccg ttgctgtcac tttccacgag   1860
cttgccacaa cgcagtttgg tcagactatc aaggtcgctg gtagcgctcc cgagctgggc   1920
aactggagca cgagcgcggc cattgctctg gatgccgtca actatgccac taaccaccct   1980
ctgtggattg gatcagtcag tctggaggcc ggagacgtta tcgagtacaa gtacatcaac   2040
gtgggccagg atggttccgt cacctgggag agcgatccca accacaccta cactgtccct   2100
gcggtggcct gtgtcactga ggtggttaag gaggacacct ggcagtcgta a            2151
```

<210> SEQ ID NO 35
<211> LENGTH: 631
<212> TYPE: PRT
<213> ORGANISM: Trichoderma asperellum

<400> SEQUENCE: 35

Met His Val Leu Ser Thr Ala Val Leu Leu Gly Ser Val Ala Val Gln
1               5                   10                  15

Lys Val Leu Gly Arg Pro Gly Ser Asn Gly Leu Ser Gly Val Thr Lys
            20                  25                  30

Arg Ser Val Asp Asp Phe Ile Asn Thr Gln Thr Pro Ile Ala Leu Asn
        35                  40                  45

```
Asn Leu Leu Cys Asn Val Gly Pro Asp Gly Cys Arg Ala Phe Gly Thr
 50                  55                  60

Ser Ala Gly Ala Val Ile Ala Ser Pro Ser Thr Asp Pro Asp Tyr
 65                  70                  75                  80

Tyr Tyr Met Trp Thr Arg Asp Ser Ala Leu Val Phe Lys Asn Ile Val
                 85                  90                  95

Asp Arg Phe Thr Gln Gln Tyr Asp Ala Gly Leu Gln Arg Arg Ile Glu
            100                 105                 110

Gln Tyr Ile Ser Ala Gln Val Thr Leu Gln Gly Ile Ser Asn Pro Ser
            115                 120                 125

Gly Ser Leu Ser Asp Gly Ser Gly Leu Gly Glu Pro Lys Phe Glu Leu
130                 135                 140

Thr Leu Ser Gln Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Ile Ile Trp Pro Ile Val
            180                 185                 190

Arg Asn Asp Leu Asn Tyr Val Ala Gln Tyr Trp Asn Gln Thr Gly Phe
            195                 200                 205

Asp Leu Trp Glu Glu Val Asn Gly Ser Ser Phe Phe Thr Val Ala Asn
210                 215                 220

Gln His Arg Ala Leu Val Glu Gly Ala Thr Leu Ala Ala Thr Leu Gly
225                 230                 235                 240

Gln Ser Gly Ser Thr Tyr Ser Ser Val Ala Pro Gln Ile Leu Cys Phe
                245                 250                 255

Leu Gln Arg Phe Trp Val Ser Gly Gly Tyr Ile Asp Ser Asn Ile Asn
            260                 265                 270

Thr Asn Glu Gly Arg Thr Gly Lys Asp Ala Asn Ser Leu Leu Ala Ser
            275                 280                 285

Ile His Thr Phe Asp Pro Ser Leu Gly Cys Asp Ala Ser Thr Phe Gln
290                 295                 300

Pro Cys Ser Asp Lys Ala Leu Ser Asn Leu Lys Val Val Val Asp Ser
305                 310                 315                 320

Phe Arg Ser Ile Tyr Gly Val Asn Lys Gly Ile Pro Ala Gly Ser Ala
                325                 330                 335

Val Ala Ile Gly Arg Tyr Pro Glu Asp Val Tyr Phe Asn Gly Asn Pro
            340                 345                 350

Trp Tyr Leu Ala Thr Phe Ala Ala Glu Gln Leu Tyr Asp Ser Val
            355                 360                 365

Tyr Val Trp Lys Lys Thr Gly Ser Ile Thr Val Thr Ser Thr Ser Leu
    370                 375                 380

Ala Phe Phe Gln Glu Leu Val Pro Gly Val Ala Ala Gly Thr Tyr Ser
385                 390                 395                 400

Ser Ser Gln Ser Thr Phe Thr Ser Ile Ile Asn Ala Val Ser Thr Tyr
                405                 410                 415

Ala Asp Gly Phe Leu Ser Glu Ala Ala Lys Tyr Val Pro Ala Asp Gly
            420                 425                 430

Ser Leu Ala Glu Gln Phe Asp Arg Asn Thr Gly Thr Pro Leu Ser Ala
            435                 440                 445

Val His Leu Thr Trp Ser Tyr Ala Ser Phe Leu Thr Ala Ala Ala Arg
450                 455                 460

Arg Ala Gly Val Val Pro Pro Ser Trp Ala Ser Ser Gly Ala Asn Ser
```

-continued

```
              465                 470                 475                 480
          Val Pro Ser Ser Cys Ser Gly Ala Ser Val Gly Ser Tyr Ser Arg
                          485                 490                 495

Pro Thr Ala Thr Ser Phe Pro Pro Ser Gln Thr Pro Lys Pro Gly Val
                      500                 505                 510

Pro Ser Gly Thr Pro Phe Thr Pro Ile Pro Cys Ala Thr Pro Thr Ser
                      515                 520                 525

Val Ala Val Thr Phe His Glu Leu Ala Thr Thr Gln Phe Gly Gln Thr
                      530                 535                 540

Ile Lys Val Ala Gly Ser Ala Pro Glu Leu Gly Asn Trp Ser Thr Ser
          545                 550                 555                 560

Ala Ala Ile Ala Leu Asp Ala Val Asn Tyr Ala Thr Asn His Pro Leu
                          565                 570                 575

Trp Ile Gly Ser Val Ser Leu Glu Ala Gly Asp Val Ile Glu Tyr Lys
                          580                 585                 590

Tyr Ile Asn Val Gly Gln Asp Gly Ser Val Thr Trp Glu Ser Asp Pro
                          595                 600                 605

Asn His Thr Tyr Thr Val Pro Ala Val Ala Cys Val Thr Glu Val Val
                      610                 615                 620

Lys Glu Asp Thr Trp Gln Ser
          625                 630

<210> SEQ ID NO 36
<211> LENGTH: 2142
<212> TYPE: DNA
<213> ORGANISM: Trichoderma strictipilis

<400> SEQUENCE: 36
atgcacgtcc tgtcgactgc ggtgctgctc ggctccgttg ccgttcaaaa ggtcctggga      60
agaccgggat caagcggtct atctgacatc accaagagat ccgtcgacga cttcatcagc     120
acccagactc ctattgcact gaacaacctt ctctgcaatg ttggtcccga tggatgtcgt     180
gcatttggca catccgctgg tgcggttatt gcatccccca gcacaactga ccccgactgt     240
aagttggaac tgttaccggc ataaacccac aggatgtgta tcgcatactg agatcgagac     300
agactattac atgtggacgc gagacagcgc tcttgtcttc aagaaccttg tcgaccgctt     360
caccgaaacg tacgatgctg ccctgcagcg ccgcatcgag cagtacatta ctgcccaggt     420
cactctccag ggcctcacca acccatcagg ttccctcgcg gacgggtctg gccttggcga     480
gcccaagttt gagttgaccc tgagtccttt caccggcaac tggggtcgac cgcagcggga     540
tggcccagct ctgcgagcca ttgccttgat tggctattcg aaatggctta tcaacaacaa     600
ctatcagtca accgtgtcca acgtcatctg gcctattgtg cgcaacgacc tcagctacgc     660
tgctcagtac tggttagtga cagcttaccc tcgaattacg gctcgtgtct aacgtcttca     720
ctacaggaac cagaccggct tgatctgtgg aagaggtt agcggaagct ctttttttac      780
tgttgccaac cagcaccgag gtatgaagca aaacgtccac actcactgtc actgtatatg     840
aacgctactg accagctccc cagctcttgt tgagggtgcc acgcttgctg ccacgctcgg     900
ccagtcggga agcacttatt catctgttgc tccccaaatc ttgtgctttc tccaacgatt     960
ctgggtgtcg tccggtggat acgtcgactc aacagtatg tccttcgctg ctcatggatt    1020
tggaaagttt ctgttactaa tgccagctcg cctctagtca acacgaatga gggtaggact    1080
ggaaaggatg tcaactccat tctcacttcc atccacacct tcgatcccaa ccttggctgt    1140
gacgcaggca ccttccagcc atgcagtgac aaagccctct ccaacttcaa ggttgttgtc    1200
```

-continued

```
gactccttcc gctccatcta cggcgtgaac aacggcattc ctgctggtgc tgccgtcgcc   1260
attggcagat atccagagga tgtgtacttc aacgggaacc cttggtacct tgccacgttt   1320
gctgctgctg agcagctgta cgacgccatc tacgtctgga agaagacggg ctccatcaca   1380
gtgactgcca tctctctcgc cttcttccag gagcttgttc ccggcgtgac agctgggacc   1440
tactccagca gccagtcgac tttcaccaac atcatcaacg ctgcctcgac atacgccgat   1500
ggcttcgtca ccgaggctgc caagtacgtt cccaccgacg gttcgctggc cgagcagttc   1560
gaccgcaaca acggcactcc gctgtccgcc cttcacctga cgtggtcgta cgcctcgttc   1620
ttgactgctt cggcccgtcg ggctggcgtc gtgcccccct cgtgggcaaa cagcagtgcc   1680
agctcgattt cttcgacgtg ctccggcgcg tccgtggtcg gatcctactc gagtcccaca   1740
gccacgtcat tccctccgtc gcagacgccc aagcccggcg ttccttccgg tacccectac   1800 acgcccctgc cctgcgctac cccaacgtcc gtggccgtca ccttccacga gctcgtgtcg   1860
acacagtttg gccagacggt caaggccgcg ggcagcgctc cggccctggg caactggagc   1920
acgagcgcgg ctgtcggtct ggacgccgtc aactacgccg ataaccaccc cctgtggatt   1980
gggacggtcg agctggaggc tggagacgtc gttgagtaca agtacatcaa tgtgggtcag   2040
gatggctccg tgacctggga gagtgacccc aaccacactt acacggttcc tgcggtggct   2100
tgtgtgacgg aggtcgtcaa ggaggacacc tggcagtcgt aa                      2142
```

<210> SEQ ID NO 37
<211> LENGTH: 632
<212> TYPE: PRT
<213> ORGANISM: Trichoderma strictipilis

<400> SEQUENCE: 37

```
Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Ile Thr Lys
            20                  25                  30

Arg Ser Val Asp Asp Phe Ile Ser Thr Gln Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Asp Pro Asp Tyr
65                  70                  75                  80

Tyr Tyr Met Trp Thr Arg Asp Ser Ala Leu Val Phe Lys Asn Leu Val
                85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Thr Asn Pro Ser
        115                 120                 125

Gly Ser Leu Ala Asp Gly Ser Gly Leu Gly Glu Pro Lys Phe Glu Leu
    130                 135                 140

Thr Leu Ser Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
            180                 185                 190

Arg Asn Asp Leu Ser Tyr Ala Ala Gln Tyr Trp Asn Gln Thr Gly Phe
        195                 200                 205
```

-continued

```
Asp Leu Trp Glu Glu Val Ser Gly Ser Ser Phe Phe Thr Val Ala Asn
    210                 215                 220
Gln His Arg Ala Leu Val Glu Gly Ala Thr Leu Ala Ala Thr Leu Gly
225                 230                 235                 240
Gln Ser Gly Ser Thr Tyr Ser Ser Val Ala Pro Gln Ile Leu Cys Phe
                245                 250                 255
Leu Gln Arg Phe Trp Val Ser Ser Gly Gly Tyr Val Asp Ser Asn Ile
            260                 265                 270
Asn Thr Asn Glu Gly Arg Thr Gly Lys Asp Val Asn Ser Ile Leu Thr
        275                 280                 285
Ser Ile His Thr Phe Asp Pro Asn Leu Gly Cys Asp Ala Gly Thr Phe
    290                 295                 300
Gln Pro Cys Ser Asp Lys Ala Leu Ser Asn Phe Lys Val Val Val Asp
305                 310                 315                 320
Ser Phe Arg Ser Ile Tyr Gly Val Asn Asn Gly Ile Pro Ala Gly Ala
                325                 330                 335
Ala Val Ala Ile Gly Arg Tyr Pro Glu Asp Val Tyr Phe Asn Gly Asn
            340                 345                 350
Pro Trp Tyr Leu Ala Thr Phe Ala Ala Ala Glu Gln Leu Tyr Asp Ala
        355                 360                 365
Ile Tyr Val Trp Lys Lys Thr Gly Ser Ile Thr Val Thr Ala Ile Ser
    370                 375                 380
Leu Ala Phe Phe Gln Glu Leu Val Pro Gly Val Thr Ala Gly Thr Tyr
385                 390                 395                 400
Ser Ser Ser Gln Ser Thr Phe Thr Asn Ile Ile Asn Ala Ala Ser Thr
                405                 410                 415
Tyr Ala Asp Gly Phe Val Thr Glu Ala Ala Lys Tyr Val Pro Thr Asp
            420                 425                 430
Gly Ser Leu Ala Glu Gln Phe Asp Arg Asn Asn Gly Thr Pro Leu Ser
        435                 440                 445
Ala Leu His Leu Thr Trp Ser Tyr Ala Ser Phe Leu Thr Ala Ser Ala
    450                 455                 460
Arg Arg Ala Gly Val Val Pro Pro Ser Trp Ala Asn Ser Ser Ala Ser
465                 470                 475                 480
Ser Ile Ser Ser Thr Cys Ser Gly Ala Ser Val Val Gly Ser Tyr Ser
                485                 490                 495
Ser Pro Thr Ala Thr Ser Phe Pro Pro Ser Gln Thr Pro Lys Pro Gly
            500                 505                 510
Val Pro Ser Gly Thr Pro Tyr Thr Pro Leu Pro Cys Ala Thr Pro Thr
        515                 520                 525
Ser Val Ala Val Thr Phe His Glu Leu Val Ser Thr Gln Phe Gly Gln
    530                 535                 540
Thr Val Lys Ala Ala Gly Ser Ala Pro Ala Leu Gly Asn Trp Ser Thr
545                 550                 555                 560
Ser Ala Ala Val Gly Leu Asp Ala Val Asn Tyr Ala Asp Asn His Pro
                565                 570                 575
Leu Trp Ile Gly Thr Val Glu Leu Glu Ala Gly Asp Val Val Glu Tyr
            580                 585                 590
Lys Tyr Ile Asn Val Gly Gln Asp Gly Ser Val Thr Trp Glu Ser Asp
        595                 600                 605
Pro Asn His Thr Tyr Thr Val Pro Ala Val Ala Cys Val Thr Glu Val
    610                 615                 620
```

```
Val Lys Glu Asp Thr Trp Gln Ser
625                 630
```

```
<210> SEQ ID NO 38
<211> LENGTH: 20
<212> TYPE: PRT
<213> ORGANISM: Trichoderma reesei

<400> SEQUENCE: 38

Met His Val Leu Ser Thr Ala Val Leu Leu Gly Ser Val Ala Val Gln
1               5                   10                  15
Lys Val Leu Gly
            20
```

```
<210> SEQ ID NO 39
<211> LENGTH: 13
<212> TYPE: PRT
<213> ORGANISM: Trichoderma reesei

<400> SEQUENCE: 39

Arg Pro Gly Ser Ser Gly Leu Ser Asp Val Thr Lys Arg
1               5                   10
```

```
<210> SEQ ID NO 40
<211> LENGTH: 453
<212> TYPE: PRT
<213> ORGANISM: Trichoderma reesei

<400> SEQUENCE: 40

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
```

```
                 225                 230                 235                 240
Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
                260                 265                 270

Pro Cys Ser Asp Lys Ala Leu Ser Asn Leu Lys Val Val Asp Ser
                275                 280                 285

Phe Arg Ser Ile Tyr Gly Val Asn Lys Gly Ile Pro Ala Gly Ala Ala
                290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
                340                 345                 350

Ala Phe Phe Gln Glu Leu Val Pro Gly Val Thr Ala Gly Thr Tyr Ser
                355                 360                 365

Ser Ser Ser Ser Thr Phe Thr Asn Ile Ile Asn Ala Val Ser Thr Tyr
                370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
                420                 425                 430

Arg Ala Gly Ile Val Pro Pro Ser Trp Ala Asn Ser Ser Ala Ser Thr
                435                 440                 445

Ile Pro Ser Thr Cys
                450

<210> SEQ ID NO 41
<211> LENGTH: 37
<212> TYPE: PRT
<213> ORGANISM: Trichoderma reesei

<400> SEQUENCE: 41

Ser Gly Ala Ser Val Val Gly Tyr Ser Arg Pro Thr Ala Thr Ser
1               5                   10                  15

Phe Pro Pro Ser Gln Thr Pro Lys Pro Gly Val Pro Ser Gly Thr Pro
                20                  25                  30

Tyr Thr Pro Leu Pro
        35

<210> SEQ ID NO 42
<211> LENGTH: 109
<212> TYPE: PRT
<213> ORGANISM: Trichoderma reesei

<400> SEQUENCE: 42

Cys Ala Thr Pro Thr Ser Val Ala Val Thr Phe His Glu Leu Val Ser
1               5                   10                  15

Thr Gln Phe Gly Gln Thr Val Lys Val Ala Gly Asn Ala Ala Ala Leu
                20                  25                  30

Gly Asn Trp Ser Thr Ser Ala Ala Val Ala Leu Asp Ala Val Asn Tyr
                35                  40                  45

Ala Asp Asn His Pro Leu Trp Ile Gly Thr Val Asn Leu Glu Ala Gly
```

```
                50                  55                  60
Asp Val Val Glu Tyr Lys Tyr Ile Asn Val Gly Gln Asp Gly Ser Val
 65                  70                  75                  80

Thr Trp Glu Ser Asp Pro Asn His Thr Tyr Thr Val Pro Ala Val Ala
                 85                  90                  95

Cys Val Thr Gln Val Val Lys Glu Asp Thr Trp Gln Ser
                100                 105

<210> SEQ ID NO 43
<211> LENGTH: 597
<212> TYPE: PRT
<213> ORGANISM: Trichoderma sp.

<400> SEQUENCE: 43

Ala Val Thr Asp Phe Ile Asn Ser Glu Thr Pro Ile Ala Leu Asn Asn
 1               5                  10                  15

Leu Ile Cys Asn Val Gly Pro Asp Gly Cys Arg Ala Phe Gly Thr Ser
                20                  25                  30

Ile Gly Ala Val Val Ala Ser Pro Ser Thr Thr Asp Pro Asp Tyr Phe
                35                  40                  45

Tyr Met Trp Thr Arg Asp Ser Ala Leu Val Phe Lys Thr Leu Val Asp
 50                  55                  60

Arg Phe Thr Gln Lys Tyr Asp Ala Gly Leu Gln Arg Arg Ile Glu Gln
 65                  70                  75                  80

Tyr Ile Ala Ala Gln Val Thr Leu Gln Gly Ile Ser Asn Pro Ser Gly
                85                  90                  95

Ser Leu Ser Asp Gly Ser Gly Leu Gly Glu Pro Lys Phe Glu Leu Thr
                100                 105                 110

Leu Ser Gln Phe Thr Gly Asn Trp Gly Arg Pro Gln Arg Asp Gly Pro
                115                 120                 125

Ala Leu Arg Ala Ile Ala Leu Ile Gly Tyr Ser Lys Trp Leu Ile Ser
                130                 135                 140

Asn Asn Tyr Gln Ser Thr Val Ser Asn Ile Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Ala Val Ala Asn Gln
                180                 185                 190

His Arg Ala Leu Val Glu Gly Ala Thr Leu Ala Thr Thr Leu Gly Gln
                195                 200                 205

Ser Gly Ser Ser Tyr Ser Thr Val Ala Pro Gln Ile Leu Cys Phe Leu
                210                 215                 220

Gln Lys Phe Trp Ser Pro Ser Gly Tyr Val Ile Ser Asn Ile Asn Ser
225                 230                 235                 240

Asn Asp Gly Arg Thr Gly Lys Asp Ser Asn Ser Ile Leu Thr Ser Ile
                245                 250                 255

His Thr Phe Asp Pro Ser Ile Gly Cys Asp Ala Ala Thr Phe Gln Pro
                260                 265                 270

Cys Ser Asp Lys Ala Leu Ser Asn Leu Lys Val Tyr Val Asp Ser Phe
                275                 280                 285

Arg Ser Ile Tyr Gly Val Asn Ser Gly Ile Pro Ala Gly Thr Ala Val
                290                 295                 300

Ala Val Gly Arg Tyr Pro Glu Asp Val Tyr Phe Asn Gly Asn Pro Trp
305                 310                 315                 320
```

```
Tyr Leu Ser Thr Phe Ala Val Ala Glu Gln Leu Tyr Asp Ala Leu Tyr
                325                 330                 335

Val Trp Lys Lys Thr Gly Ser Ile Thr Val Ser Thr Ser Leu Ala
            340                 345                 350

Phe Phe Gln Glu Leu Val Pro Ser Val Thr Ala Gly Thr Tyr Ala Ser
                355                 360                 365

Ser Ser Ser Thr Phe Thr Ser Ile Val Asn Ala Val Ser Thr Tyr Ala
            370                 375                 380

Asp Gly Phe Val Ser Glu Ala Ala Lys Tyr Val Pro Ser Asp Gly Ser
385                 390                 395                 400

Leu Ser Glu Gln Phe Asp Lys Asn Thr Gly Thr Pro Leu Ser Ala Val
                405                 410                 415

His Leu Thr Trp Ser Tyr Ala Ser Phe Leu Ala Thr Thr Arg Arg
            420                 425                 430

Ala Gly Ile Val Pro Pro Ser Trp Ile Ser Gly Ala Asn Thr Val
            435                 440                 445

Pro Ser Ser Cys Ser Gly Thr Thr Val Ala Gly Ser Tyr Ser Ser Pro
            450                 455                 460

Thr Ala Thr Ser Phe Pro Pro Ser Gln Thr Pro Lys Thr Ala Ala Thr
465                 470                 475                 480

Gly Thr Ser Phe Thr Pro Ile Ala Cys Ala Thr Pro Thr Ser Val Ala
                485                 490                 495

Val Thr Phe His Glu Leu Ala Thr Thr Val Pro Gly Gln Thr Ile Lys
                500                 505                 510

Val Val Gly Asn Ala Gln Ala Leu Gly Asn Trp Ser Thr Ser Ala Gly
            515                 520                 525

Val Ala Leu Asn Ala Val Asn Cys Ala Ser Asn His Pro Leu Trp Ile
            530                 535                 540

Gly Pro Val Asn Leu Lys Ala Gly Asp Val Val Glu Tyr Lys Tyr Ile
545                 550                 555                 560

Asn Val Gly Ser Asp Gly Ser Val Thr Trp Glu Ala Asp Pro Asn His
                565                 570                 575

Thr Tyr Thr Val Pro Ala Val Ala Cys Val Thr Ala Val Val Lys Glu
                580                 585                 590

Asp Thr Trp Gln Ser
            595

<210> SEQ ID NO 44
<211> LENGTH: 598
<212> TYPE: PRT
<213> ORGANISM: Trichoderma harzianum

<400> SEQUENCE: 44

Ser Val Asp Asp Ser Ile Asn Thr Gln Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Thr Asp Pro Asp Tyr Tyr
            35                  40                  45

Tyr Met Trp Thr Arg Asp Ser Ala Leu Val Phe Lys Asn Ile Val Asp
        50                  55                  60

Arg Phe Thr Glu Gln Tyr Asp Ala Gly Leu Gln Arg Ile Glu Gln
65                  70                  75                  80

Tyr Ile Ser Ala Gln Val Thr Leu Gln Gly Ile Ser Asn Pro Ser Gly
                85                  90                  95
```

-continued

```
Ser Leu Ser Asp Gly Ser Gly Leu Gly Glu Pro Lys Phe Glu Leu Thr
            100                 105                 110
Leu Ser Gln Phe Thr Gly Asn Trp Gly Arg Pro Gln Arg Asp Gly Pro
        115                 120                 125
Ala Leu Arg Ala Ile Ala Leu Ile Gly Tyr Ser Lys Trp Leu Ile Asn
    130                 135                 140
Asn Asn Tyr Gln Ser Thr Val Ser Asn Ile Ile Trp Pro Ile Val Arg
145                 150                 155                 160
Asn Asp Leu Asn Tyr Val Ala Gln Tyr Trp Asn Gln Thr Gly Phe Asp
                165                 170                 175
Leu Trp Glu Glu Val Asn Gly Ser Ser Phe Phe Thr Val Ala Asn Gln
            180                 185                 190
His Arg Ala Leu Val Glu Gly Ala Thr Leu Ala Ala Thr Leu Gly Gln
        195                 200                 205
Ser Gly Ser Thr Tyr Ser Ser Val Ala Pro Gln Ile Leu Cys Phe Leu
    210                 215                 220
Gln Arg Phe Trp Val Ser Gly Tyr Ile Asp Ser Asn Ile Asn Thr
225                 230                 235                 240
Asn Glu Gly Arg Thr Gly Lys Asp Ala Asn Ser Leu Leu Ala Ser Ile
                245                 250                 255
His Thr Phe Asp Pro Ser Leu Gly Cys Asp Ala Ser Thr Phe Gln Pro
            260                 265                 270
Cys Ser Asp Lys Ala Leu Ser Asn Leu Lys Val Val Asp Ser Phe
        275                 280                 285
Arg Ser Ile Tyr Ser Val Asn Lys Gly Ile Pro Ala Gly Ala Ala Val
    290                 295                 300
Ala Val Gly Arg Tyr Pro Glu Asp Val Tyr Phe Asn Gly Asn Pro Trp
305                 310                 315                 320
Tyr Leu Ala Thr Phe Ala Ala Ala Glu Gln Leu Tyr Asp Ser Val Tyr
                325                 330                 335
Val Trp Lys Lys Thr Gly Ser Ile Thr Val Thr Ser Thr Ser Leu Ala
            340                 345                 350
Phe Phe Gln Glu Leu Val Pro Gly Val Ala Ala Gly Thr Tyr Ser Ser
        355                 360                 365
Ser Gln Ser Thr Phe Thr Ser Ile Ile Asn Ala Val Ser Thr Tyr Ala
    370                 375                 380
Asp Gly Phe Leu Ser Glu Ala Ala Lys Tyr Val Pro Ala Asp Gly Ser
385                 390                 395                 400
Leu Ala Glu Gln Phe Asp Arg Asn Thr Gly Thr Pro Leu Ser Ala Val
                405                 410                 415
His Leu Thr Trp Ser Tyr Ala Ser Phe Leu Thr Ala Ala Arg Arg
            420                 425                 430
Ala Gly Val Val Pro Pro Ser Trp Ala Ser Ser Gly Ala Asn Ser Val
        435                 440                 445
Pro Ser Ser Cys Ser Gly Ala Ser Val Val Gly Ser Tyr Ser Arg Pro
    450                 455                 460
Thr Ala Thr Ser Phe Pro Pro Ser Gln Thr Pro Lys Pro Gly Ala Pro
465                 470                 475                 480
Ser Gly Ala Pro Phe Thr Pro Ile Pro Cys Ala Thr Pro Ala Ser Val
                485                 490                 495
Ala Val Thr Phe His Glu Leu Ala Thr Thr Gln Phe Gly Gln Thr Ile
            500                 505                 510
```

```
Lys Val Ala Gly Ser Ala Pro Glu Leu Gly Asn Trp Ser Thr Ser Ala
                515                 520                 525

Ala Ile Ala Leu Asp Ala Val Asn Tyr Ala Thr Asn His Pro Leu Trp
            530                 535                 540

Ile Gly Ser Val Asn Leu Glu Ala Gly Asp Val Ile Glu Tyr Lys Tyr
545                 550                 555                 560

Ile Ser Val Gly Gln Asp Gly Ser Val Thr Trp Glu Ser Asp Pro Asn
                565                 570                 575

His Thr Tyr Thr Val Pro Ala Val Ala Cys Val Thr Glu Val Val Lys
            580                 585                 590

Glu Asp Thr Trp Gln Ser
            595

<210> SEQ ID NO 45
<211> LENGTH: 599
<212> TYPE: PRT
<213> ORGANISM: Trichoderma longibrachiatum

<400> SEQUENCE: 45

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Ile Asp Pro Asp Tyr Tyr
            35                  40                  45

Tyr Met Trp Thr Arg Asp Ser Ala Leu Val Phe Lys Asn Leu Val Asp
50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Thr Asp Gly Ser Gly Leu Gly Glu Pro Lys Phe Glu Leu Thr
                100                 105                 110

Leu Lys Pro Phe Thr Gly Asn Trp Gly Arg Pro Gln Arg Asp Gly Pro
            115                 120                 125

Ala Leu Arg Ala Val Ala Leu Ile Gly Tyr Ser Lys Trp Leu Ile Asn
130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Met Ala Asn Gln
            180                 185                 190

His Arg Ala Leu Val Glu Gly Ala Thr Leu Ala Ala Thr Leu Gly Gln
            195                 200                 205

Ser Gly Ser Thr Tyr Ser Ser Val Ala Pro Gln Ile Leu Cys Phe Leu
        210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Ala Thr Phe Gln
            260                 265                 270

Pro Cys Ser Asp Lys Ala Leu Ser Asn Leu Lys Val Val Val Asp Ser
        275                 280                 285
```

```
Phe Arg Ser Ile Tyr Gly Val Asn Lys Gly Ile Pro Ala Gly Ala Ala
    290                 295                 300

Val Ala Ile Gly Arg Tyr Ala Glu Asp Val Tyr Phe Asn Gly Asn Pro
305                 310                 315                 320

Trp Tyr Leu Ala Thr Phe Ala Ala Glu Gln Leu Tyr Asp Ala Ile
                325                 330                 335

Tyr Val Trp Lys Lys Thr Gly Ser Ile Thr Val Thr Ala Thr Ser Leu
                340                 345                 350

Ala Phe Phe Gln Glu Leu Val Pro Gly Val Ala Gly Thr Tyr Ala
            355                 360                 365

Ser Ser Ser Ser Thr Phe Thr Asn Ile Ile Asn Ala Val Ser Thr Tyr
    370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
                420                 425                 430

Arg Ala Gly Ile Val Pro Pro Ser Trp Ala Asn Ser Ser Ala Ser Thr
            435                 440                 445

Ile Pro Ser Thr Cys Ser Gly Ala Ser Val Val Gly Ser Tyr Ser Arg
    450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
                485                 490                 495

Val Ala Val Thr Phe His Glu Leu Val Ser Thr Gln Phe Gly Gln Thr
                500                 505                 510

Val Lys Val Ala Gly Asn Ala Pro Ala Leu Gly Asn Trp Ser Ala Ser
            515                 520                 525

Ala Ala Val Ala Leu Asp Ala Ile Asn Tyr Ala Asp Asn His Pro Leu
    530                 535                 540

Trp Ile Gly Thr Val Asp Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
            580                 585                 590

Lys Glu Asp Thr Trp Gln Ser
            595

<210> SEQ ID NO 46
<211> LENGTH: 598
<212> TYPE: PRT
<213> ORGANISM: Trichoderma asperellum

<400> SEQUENCE: 46

Ser Val Asp Asp Phe Ile Asn Thr Gln Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Thr Asp Pro Asp Tyr Tyr
        35                  40                  45

Tyr Met Trp Thr Arg Asp Ser Ala Leu Val Phe Lys Asn Ile Val Asp
```

-continued

```
            50                  55                  60
Arg Phe Thr Gln Gln Tyr Asp Ala Gly Leu Gln Arg Ile Glu Gln
 65                      70                  75                  80

Tyr Ile Ser Ala Gln Val Thr Leu Gln Gly Ile Ser Asn Pro Ser Gly
                     85                  90                  95

Ser Leu Ser Asp Gly Ser Gly Leu Gly Glu Pro Lys Phe Glu Leu Thr
                100                 105                 110

Leu Ser Gln Phe Thr Gly Asn Trp Gly Arg Pro Gln Arg Asp Gly Pro
                115                 120                 125

Ala Leu Arg Ala Ile Ala Leu Ile Gly Tyr Ser Lys Trp Leu Ile Asn
130                 135                 140

Asn Asn Tyr Gln Ser Thr Val Ser Asn Ile Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
                180                 185                 190

His Arg Ala Leu Val Glu Gly Ala Thr Leu Ala Ala Thr Leu Gly Gln
                195                 200                 205

Ser Gly Ser Thr Tyr Ser Ser Val Ala Pro Gln Ile Leu Cys Phe Leu
                210                 215                 220

Gln Arg Phe Trp Val Ser Gly Gly Tyr Ile Asp Ser Asn Ile Asn Thr
225                 230                 235                 240

Asn Glu Gly Arg Thr Gly Lys Asp Ala Asn Ser Leu Leu Ala Ser Ile
                245                 250                 255

His Thr Phe Asp Pro Ser Leu Gly Cys Asp Ala Ser Thr Phe Gln Pro
                260                 265                 270

Cys Ser Asp Lys Ala Leu Ser Asn Leu Lys Val Val Asp Ser Phe
                275                 280                 285

Arg Ser Ile Tyr Gly Val Asn Lys Gly Ile Pro Ala Gly Ser Ala Val
                290                 295                 300

Ala Ile Gly Arg Tyr Pro Glu Asp Val Tyr Phe Asn Gly Asn Pro Trp
305                 310                 315                 320

Tyr Leu Ala Thr Phe Ala Ala Ala Glu Gln Leu Tyr Asp Ser Val Tyr
                325                 330                 335

Val Trp Lys Lys Thr Gly Ser Ile Thr Val Thr Ser Thr Ser Leu Ala
                340                 345                 350

Phe Phe Gln Glu Leu Val Pro Gly Val Ala Ala Gly Thr Tyr Ser Ser
                355                 360                 365

Ser Gln Ser Thr Phe Thr Ser Ile Ile Asn Ala Val Ser Thr Tyr Ala
                370                 375                 380

Asp Gly Phe Leu Ser Glu Ala Ala Lys Tyr Val Pro Ala Asp Gly Ser
385                 390                 395                 400

Leu Ala Glu Gln Phe Asp Arg Asn Thr Gly Thr Pro Leu Ser Ala Val
                405                 410                 415

His Leu Thr Trp Ser Tyr Ala Ser Phe Leu Thr Ala Ala Ala Arg Arg
                420                 425                 430

Ala Gly Val Val Pro Pro Ser Trp Ala Ser Ser Gly Ala Asn Ser Val
                435                 440                 445

Pro Ser Ser Cys Ser Gly Ala Ser Val Val Gly Ser Tyr Ser Arg Pro
                450                 455                 460

Thr Ala Thr Ser Phe Pro Pro Ser Gln Thr Pro Lys Pro Gly Val Pro
465                 470                 475                 480
```

```
Ser Gly Thr Pro Phe Thr Pro Ile Pro Cys Ala Thr Pro Ser Val
                485                 490                 495

Ala Val Thr Phe His Glu Leu Ala Thr Thr Gln Phe Gly Gln Thr Ile
            500                 505                 510

Lys Val Ala Gly Ser Ala Pro Glu Leu Gly Asn Trp Ser Thr Ser Ala
            515                 520                 525

Ala Ile Ala Leu Asp Ala Val Asn Tyr Ala Thr Asn His Pro Leu Trp
            530                 535                 540

Ile Gly Ser Val Ser Leu Glu Ala Gly Asp Val Ile Glu Tyr Lys Tyr
545                 550                 555                 560

Ile Asn Val Gly Gln Asp Gly Ser Val Thr Trp Glu Ser Asp Pro Asn
                565                 570                 575

His Thr Tyr Thr Val Pro Ala Val Ala Cys Val Thr Glu Val Val Lys
                580                 585                 590

Glu Asp Thr Trp Gln Ser
            595
```

<210> SEQ ID NO 47
<211> LENGTH: 599
<212> TYPE: PRT
<213> ORGANISM: Trichoderma strictipilis

<400> SEQUENCE: 47

```
Ser Val Asp Asp Phe Ile Ser Thr Gln Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Thr Asp Pro Asp Tyr Tyr
            35                  40                  45

Tyr Met Trp Thr Arg Asp Ser Ala Leu Val Phe Lys Asn Leu Val Asp
        50                  55                  60

Arg Phe Thr Glu Thr Tyr Asp Ala Gly Leu Gln Arg Ile Glu Gln
65                  70                  75                  80

Tyr Ile Thr Ala Gln Val Thr Leu Gln Gly Leu Thr Asn Pro Ser Gly
                85                  90                  95

Ser Leu Ala Asp Gly Ser Gly Leu Gly Glu Pro Lys Phe Glu Leu Thr
            100                 105                 110

Leu Ser Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Val Ile Trp Pro Ile Val Arg
145                 150                 155                 160

Asn Asp Leu Ser Tyr Ala Ala Gln Tyr Trp Asn Gln Thr Gly Phe Asp
                165                 170                 175

Leu Trp Glu Glu Val Ser Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Thr Tyr Ser Ser Val Ala Pro Gln Ile Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Ile Leu Thr Ser
```

-continued

```
                245                 250                 255
Ile His Thr Phe Asp Pro Asn Leu Gly Cys Asp Ala Gly Thr Phe Gln
            260                 265                 270

Pro Cys Ser Asp Lys Ala Leu Ser Asn Phe Lys Val Val Asp Ser
        275                 280                 285

Phe Arg Ser Ile Tyr Gly Val Asn Asn Gly Ile Pro Ala Gly Ala Ala
        290                 295                 300

Val Ala Ile Gly Arg Tyr Pro Glu Asp Val Tyr Phe Asn Gly Asn Pro
305                 310                 315                 320

Trp Tyr Leu Ala Thr Phe Ala Ala Glu Gln Leu Tyr Asp Ala Ile
                325                 330                 335

Tyr Val Trp Lys Lys Thr Gly Ser Ile Thr Val Thr Ala Ile Ser Leu
                340                 345                 350

Ala Phe Phe Gln Glu Leu Val Pro Gly Val Thr Ala Gly Thr Tyr Ser
                355                 360                 365

Ser Ser Gln Ser Thr Phe Thr Asn Ile Ile Asn Ala Ala Ser Thr Tyr
        370                 375                 380

Ala Asp Gly Phe Val Thr Glu Ala Ala Lys Tyr Val Pro Thr Asp Gly
385                 390                 395                 400

Ser Leu Ala Glu Gln Phe Asp Arg Asn Asn Gly Thr Pro Leu Ser Ala
                405                 410                 415

Leu His Leu Thr Trp Ser Tyr Ala Ser Phe Leu Thr Ala Ser Ala Arg
                420                 425                 430

Arg Ala Gly Val Val Pro Pro Ser Trp Ala Asn Ser Ser Ala Ser Ser
                435                 440                 445

Ile Ser Ser Thr Cys Ser Gly Ala Ser Val Val Gly Ser Tyr Ser Ser
        450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
                485                 490                 495

Val Ala Val Thr Phe His Glu Leu Val Ser Thr Gln Phe Gly Gln Thr
                500                 505                 510

Val Lys Ala Ala Gly Ser Ala Pro Ala Leu Gly Asn Trp Ser Thr Ser
                515                 520                 525

Ala Ala Val Gly Leu Asp Ala Val Asn Tyr Ala Asp Asn His Pro Leu
                530                 535                 540

Trp Ile Gly Thr Val Glu Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575

Asn His Thr Tyr Thr Val Pro Ala Val Ala Cys Val Thr Glu Val Val
                580                 585                 590

Lys Glu Asp Thr Trp Gln Ser
                595
```